United States Patent [19]

Studnicka

[11] Patent Number: 5,869,619
[45] Date of Patent: Feb. 9, 1999

[54] MODIFIED ANTIBODY VARIABLE DOMAINS

[75] Inventor: Gary M. Studnicka, Santa Monica, Calif.

[73] Assignee: XOMA Corporation, Berkeley, Calif.

[21] Appl. No.: 82,842

[22] Filed: Jun. 23, 1993

Related U.S. Application Data

[63] Continuation-in-part of PCT/US92/10906, Dec. 14, 1992, which is a continuation-in-part of Ser. No. 808,464, Dec. 13, 1991, abandoned.

[30] Foreign Application Priority Data

Dec. 14, 1992 [WO] WIPO ............ PCT/US92/10906

[51] Int. Cl.⁶ ............................................. A61K 39/395
[52] U.S. Cl. ............................ 530/387.3; 435/172.3; 424/133.1
[58] Field of Search ............... 530/387.3; 424/133.1; 435/172.3

[56] References Cited

U.S. PATENT DOCUMENTS

| | | | |
|---|---|---|---|
| 3,376,110 | 4/1968 | Shiraeff et al. | 23/207.5 |
| 4,016,043 | 4/1977 | Schuurs et al. | 195/103.5 |
| 4,391,904 | 7/1983 | Litman et al. . | |
| 4,816,397 | 3/1989 | Boss et al. | 435/68 |
| 4,816,567 | 3/1989 | Cabilly et al. | 530/387 |
| 4,853,871 | 8/1989 | Pantoliano et al. . | |
| 4,888,415 | 12/1989 | Lambert et al. . | |
| 4,925,673 | 5/1990 | Steiner et al. . | |
| 4,946,778 | 8/1990 | Ladner et al. . | |
| 5,101,025 | 3/1992 | Piatak, Jr. et al. . | |
| 5,225,539 | 7/1993 | Winter . | |
| 5,585,089 | 12/1996 | Queen et al. . | |

FOREIGN PATENT DOCUMENTS

| | | |
|---|---|---|
| 0 120 694 A2 | 10/1984 | European Pat. Off. . |
| 0 125 023 A1 | 11/1984 | European Pat. Off. . |
| 0 173 494 A2 | 3/1986 | European Pat. Off. . |
| 0 239 400 A2 | 9/1987 | European Pat. Off. . |
| 0 125 023 B1 | 6/1991 | European Pat. Off. . |
| 0 440 351 A2 | 8/1991 | European Pat. Off. . |
| 0 519 596 A1 | 12/1992 | European Pat. Off. . |
| 0 592 106 A1 | 4/1994 | European Pat. Off. . |
| 0 451 216 B1 | 1/1996 | European Pat. Off. . |
| 2188638 B | 10/1987 | United Kingdom . |
| 2177096 B | 5/1989 | United Kingdom . |
| WO 86/01533 | 3/1986 | WIPO . |
| WO 89/00999 | 2/1989 | WIPO . |
| WO 89/01783 | 3/1989 | WIPO . |
| WO 89/09622 | 10/1989 | WIPO . |
| WO 90/07861 | 7/1990 | WIPO . |
| WO 92/04380 | 3/1992 | WIPO . |
| WO 92/07075 | 4/1992 | WIPO . |
| WO 92/15327 | 9/1992 | WIPO . |
| WO 92/22324 | 12/1992 | WIPO . |
| WO 92/22653 | 12/1992 | WIPO . |
| WO 93/05168 | 3/1993 | WIPO . |

OTHER PUBLICATIONS

Padlan, E.A. Molecular Immunology 28(4/5):489–498, Apr. 1991.
Byers, V.S. et al. Blood 75(7):1426–1432, Apr. 1990.
Schlom, J. Molecular Foundations of Oncology, Samuel Broder (Ed.), Williams and Wilkins, Baltimore, MD, Chapter 6 pp. 95–134, 1991.
Alegre et al., *J. Immunol.*, 148(11): 3461–3468 (1992) "Effect of a Single Amino Acid Mutation on the Activating and Immunosuppressive Properties of a Humanized OKT3 Monoclonal Antibody".
Barry, Dermatological Formulations p. 181 (1983) "Percutaneous Absorption".
Better et al., *J. Biol. Chem.*, 267(23): 16712–16718 (1992) "Activity of Recombinant Mitogillin and Mitogillin Immunoconjugates".
Better et al., *Proc Natl. Acad. Sci. USA*, 90: 457–461 (1993) "Potent Anti–CD5 Ricin A Chain Immunoconjugates from Bacterially Produced FAb' and F(ab')2".
Bird et al., *Science*, 242: 423–426 (1988) "Single–Chain Antigen–Binding Proteins".
Bolt et al., *Eur. J. Immunl*, 23(2): 403–411 (1993) "The Generation of a Humanized, Non–Mitogenic CD3 Monoclonal Antibody Which Retains In Vitro Immunosupressive Properties".
Borrebaeck e tal., *Bio/Technology*, "Kinetic Analysis of Recombinant Antibody–Antigen Interactions: Relation Between Structural Domains and Antigen Binding" vol. 10(6) 697–8 Jun. 10, 1992.
Boulianne et al., *Nature*, 312: 643–646 (1984) "Production of Functional Chimeric Mouse/Human Antibody".
Brady et al., *J. Mol. Biol.*, 227: 253–264 (1992) "Crystal Structure of a Chimeric Fab' Fragment of an Antibody Binding Tumour Cells".
Brown et al., *Proc. Natl. Acad. Sci. USA*, 88: 2663–2667 (1991) "Anti–Tac–H, a Humanizaed Antibody To The Interleukin 2 Receptor, Prolongs Primate Cardiac Allograft Survival".
Bruggemann et al., *J. Exp. Med.*, 170: 2153–2157 (1989) "The Immunogenicicty of Chimeric Antibodies".
Buchner et al., *Biotechnology*, 9: 157–162 (1991) "Renaturation, Purification and Charactrization of Recombinant $F_{ab}$–Fragments Produced in *Escherichia Coli*".
Byers et al. *Blood*, 75(7): 1426–1432 (1990) "Use of An Anti–Pan T–Lymphocyte Ricin A Chain Immunotoxin In Steroid–Resistant Acute Graft–Versus–Host Disease".

(List continued on next page.)

*Primary Examiner*—Sheela Huff
*Assistant Examiner*—Julie E. Reeves
*Attorney, Agent, or Firm*—McAndrews, Held & Malloy, Ltd.

[57] ABSTRACT

Methods are described for identifying the amino acid residues of an antibody variable domain which may be modified without diminishing the native affinity of the domain for antigen while reducing its immunogenicity with respect to a heterologous species and for preparing so modified antibody variable domains which are useful for administration to heterologous species. Antibody variable regions prepared by the methods of the invention are also described.

17 Claims, 26 Drawing Sheets

OTHER PUBLICATIONS

Caron et al., *Cancer Res.*, 52(24): 6761–6767 (1992) "Biological and Immunological Features of Humanized M195 (Anti–Cd33) Monoclonal Antibodies".

Carter et al., *Proc. Natl. Acad. Sci. USA*, 89: 4285–4289 (1992) "Humanization of Anti–p185$^{HER2}$ Antibody for Human Cancer Therapy".

Case et al., *Proc. Natl. Acad. Sci. USA*, 86: 287–291 (1989) "Chimieric Cytotoxin IL2–PE40 Delays and Mitigates Adjuvant–Induced Arthritis in Rats".

Cheadle et al., *Mol. Immunol.*, 29: 21–30 (1992) "Cloning and Expression of the Variable Regions of Mouse Myeloma Protein MOPC15 in *E. Coli*: Recovery of Active $F_v$ Fragments".

Chothia et al., *The EMBO Journal*, 7(12): 3745–3755 (1988) "The Outline Structure of the T–Cell αβ Receptor".

Chothia et al., *J. Mol. Biol.*, 196: 901–917 (1987) "Canonical Structures for the Hypervariable Regions of Immunoglobulins".

Chothia et al., *Nature*, 342: 877–883 (1989) "Conformations of Immunoglobulin Hypervariable Regions".

Chothia et al., *J. Mol. Biol.*, 186: 651–663 (1985) "Domain Association in Immunoglobulin Molecules, The Packing of Variable Domains".

Chothia and Lesk, *Cold Spring Harbor Symp. Quant. Biol.*, 52: 399–405 (1987) "The Evolution of Protein Structures".

Choy et al., *Scandinavian J. Immunol.*, 36: 291–298 (1992) "Treatment of Rheumatiod Arthritis With Single Dose or Weekly Pulses of Chimaeric Anti–CD4 Monoclonal Antibody".

Co et al., *Nature*, 351: 501–502 (1991) "Humanized Antibodies for Therapy".

Co et al., *Proc. Natl. Acad. Sci. USA*, 88: 2869–2873 (1991) "Humanized Antibodies for Antiviral Therapy".

Co et al., *J. Immunol.*, 148: 1149–1154 (1992) "Chimeric and Humanized Antibodies with Specificity for the CD33 Antigen".

Daugherty, et al., *Nucleic Acids Res.*, 19: 2471–2476 (1991) "Polymerase Chain Reaction Facilitates the Cloning, CDR–grafting, and Rapid Expression of a Murine Monoclonal Antibody Directed Against the CD18 Component of Leukocyte Integrins".

Davies & Metzger, *Ann. Rev. Immunol.*, 1: 87–117 (1983) "Structural Basis of Antibody Function".

Davies and Padlan, *Ann. Rev. Biochem.*, 59: 439–473 (1990) "Antibody–Antigen Complexes".

Derocq et al., *Transplantation*, 44(6): 763–769 (1987) "Rationale for the Selection of Ricin A–Chain Anti–T Immunitoxins for Mature T Cell Depletion".

Eigenbrot et al., *J. Mol. Biol.*, 229: 969–995 (1993) "X–ray Structures of the Antigen–binding Domains from Three Variants of Humanized Anti–p185$^{HER3}$ 4D5 and Comparison with Molecular Modeling".

Ey et al., *Immunochem.*, 15: 429–436 (1978) "Isolation of pure $IgG_1$, $IgG_{2a}$ and $IgG_{2b}$ Immunoglobulins from Mouse Serum using Protein A–Sepharose".

Fishwild et al., *Clin. Exp. Immunol.*, 86: 506–513 (1991) "Cytotoxicity Against Human Peripheral Blood Mononuclear Cells and T Cell Lines Mediated By Anti–T cell Immunotoxins in the Absence of Added Potentiator".

Fishwild et al., *Clin. Exp. Immunol.*, 7: 10–18 (1994) "Characterization of the Increased Cytotoxicity of Gelonin Anti–T Cell Immunoconjugates Compared with Ricin A Chain Immunoconjugates".

Foote et al., *J. Mol. Biol.*, 224: 487–499 (1992) "Antibody Framework Residues Affecting the Conformation of Hypervariable Loops".

Galfre et al., *Nture*, 226: 550–552 (1977) "Antibodies to Major Histocompatiblity Antigens Produced by Hybrid Cell Lines".

Glaser et al., *J. Immunol.*, 149(8): 2607–2614 (1992) "Dissection of the Combining Site in a Humanized Anti–Tac Antibody".

Glockshuber et al., *Biochemistry*, 29: 1362–1367 (1990) "A Comparison of Strategies to Stabilize Immunoglobulin in $F_v$–Fragments".

Goff et al., *Bioconjugates Chem.*, 1: 381–386 (1990) "Substituted 2–Iminothiolanes; Reagents for the Preparation of Disulfide Cross–Linked Conjugates With Increased Stability".

Goldberg et al., *J. Autoimmunity*, 4: 617–630 (1991) "Immunological Effects of High Dose Administration of Anti–CD4 Antibody In Rheumatoid Arthritis Patients".

Goldberg et al., *Arthritis and Rheumatism*, 33: S153, Abstract D115 (1990) "Preliminary Trial of an Anti–CD4 Monoclonal Antibody (MoAb) in Rheumatoid Arthritis (RA)".

Gorman et al., *Proc. Natl. Acad. Sci. USA*, 88: 4181–4185 (1991) "Reshaping a Therapeutic CD4 Antibody".

Hafler et al., *Neurology*, 36: 777–784 (1986) "Immunologic Responses of Progressive Multiple Sclerosis Patients Treated With an Anti–T–Cell Monoclonal Antibody, Anti–T12".

Hakimi et al., *J. Immunol.*, 147: 1352–1359 (1991) "Reduced Immunogenicity and Improved Pharmacokinetics Of Humanized Anti–Tac in Cynomolgus Monkeys".

Hakimi et al., *J. Immunol.*, 151: 1075 (1993) "Humanized Mikβ1, A Humanized Antibody to the Il–2 Receptor β–chain That Acts Synergistically With Humanized Anti–TAC".

Hale et al., *The Lancet*, 11: 1394–1399 (1988) "Remission Induction in Non–Hodgkin Lymphoma With Reshaped Human Monoclonal Antibody Campath–1H".

Hara et al., *Clinical Immunology and Immunopathology*, 49: 223–230 (1988 "Stimulatory Effect of CD5 Antibody on B Cells from Patients With Rheumatoid Arthritis".

Harlow et al., Eds., Antibodies: A Laboratory Manual, Chapter 14, "Immunoassays", Cold Spring Harbor Laboratory, Cold Spring Harbor (1988).

Hodgson, *Biotechnology*, 8: 1245–1247 (1990) "Protein Design: Rules, Empiricism, & Nature".

Horneff et al., *Arthritis and Rheumatism*, 34(2): 129–140 (1991) "Treatment of Rheumatoid Rheumatoid Arthritis With An Anti–CD4 Monoclonal Antibody".

Hsiao et al., Antibody Engineering Meeting, Dec. 14–16, 1992, Abstract "Humanization of Anti–CD18 mAb 60.3".

Huse et al., *Science*, 246: 1275–1281 (1989) "Generation of a Large Combinatorial Library of the Immunoglobulin Repertoire in Phage Lambda".

Huston et al., *Proc. Natl. Acad. Sci. USA*, 85: 5879–5883 (1988) "Protein Engineering of Antibody Binding Sites: Recovery of Specific Activity in an Anti–Digoxin Single–Chain Fv Analogue Produced in *Escherichia coli*".

Janin et al., *J. Biol. Chem.*, 265: 16027–16030 (1990) "The Structure of Protein–Protein Recognition Sites".

Jones et al., *Biotechnology*, 8: 88–89 (1991) "Rapid PCR Cloning of Full–Length Mouse Immunoglobulin Variable Regions".

Jones et al., *Nature*, 321: 522–525 (1986) "Replacing the Complementarity–Determining Regions in a Human Antibody with those from a Mouse".

Junghans et al., *Cancer Res.*, 50 (5): 1495–1502 (1990) "Anti–Tac–H, A Humanized Antibody to the Interleukin 2 Receptor with New Features for Immunotherapy in Malignant and Immune Disorders".

Kabat et al., *J. Biol. Chem.*, 252 (19): 6609–6616 (1977) "Unusual Distributions of Amino Acids in Complementarity–Determining (Hypervariable) Segments of Heavy and Light Chains of Immunoglobulins and their Possible Roles in Specificity of Antibody–Combining Sites".

Kelley et al., *Biochem.*, 32: 6828–6835 (1993) "Thermodynamic Analysis of an Antibody Functional Epitope".

Kelley et al., *Biochem.*, 31: 5434–5441 (1992) "Antigen Binding Thermodynamics and Antiproliferative Effects of Chimeric and Humanized Anti–p185$^{HER2}$ Antibody Fab Fragments".

Kernan et al., *J. Immunol.*, 133 (1): 137–146 (1984) Specific Inhibition of in vitro Lymphocyte Transformation by an Anti–Pan T Cell (gp67) Ricin A Chain Immunotoxin.

Kettleborough et al., *Protein Engineering*, 4: 773–783 (1991) "Humanization of a Mouse Monoclonal Antibody by CDR–Grafting: The Importance of Framework Residues on Loop Conformation".

Kirkham et al., *Brit. J. Rheumatology*, 30: 88 Abstract 16 (1991) "Chimeric (Human/Mouse) CD7 Monoclonal Antibody Treatment in Rheumatoid Arthritis".

Kirkham et al., *Brit. J. Rheumatology*, 30: 459–463 (1991) "Monoclonal Antibody Treatment in Rheumatoid Arthritis: The Clinical and Immunological Effects of a CD7 Monoclonal Antibody".

Kirkham et al., *J. Rheumatology*, 19: 1348–1352 (1992) "Chimeric CD7 Monoclonal Antibody Therapy in Rheumatoid Arthritis".

Knowles, Chapter 22 in Reinherz et al., Leukocyte Typing II, 1: 259–288 (Springer–Verlag, 1986) "Immunochemical Analysis of the T–Cell Specific Antigens".

Koda et al., *Hum. Antibody Hybridomas* 1(1): 15–22 (1990) Review "In Vitro Immunization for the Production of Human Monoclonal Antibody".

Kohler et al., *Eur. J. Immunol.*, 6: 292–295 (1976) "Fusion Between Immunoglobulin–Secreting and Nonsecreting Myeloma Cell Lines".

Kyle et al., *j. Rheumatol.*, 18: 1737–1738 "Humanized Monoclonal Antibody Treatment in Rheumatoid Arthritis" (1991).

Lambert et al., *J. Biol. Chem.*, 246: 12035–12041 (1985) "Purified Immunotoxins that are Reactive with Human Lymphoid Cells".

Kaurent et al., *Bone Marrow Transplantation.* 4; 367–371 (1989) "Donor Bone Marrow Treatment With T101 Fab Fragment–Ricin A–Chain Immunotoxin Prevents Graft–Versus–Host Disease".

Lazarovits et al., *J. Immunol.*, 150(11): 5163–5174 (1993) "Human Mouse Chimeric CD7 Monoclonal Antibody (SDZCHH380) for the Prophylaxis of Kidney Transplant Rejection".

Lesk et al., *Nature*, 335: 188–190 (1988) "Elbow Motion in the Immunoglobulins Involves a Molecular Ball–and–socket Joint".

Liu et al., *Gene*, 54: 33–40 (1987) "Expression of Mouse: Human Immunoglobulin Heavy–Chain cDNA in Lymphoid Cells".

LoBuglio et al., *Proc. Natl. Acad. Sci. USA*, 86: 4220–4224 (1989) "Mouse/Human Chimeric Monoclonal Antibody in Man: Kinetics and Immune Response".

Marks et al., *J. Mol. Biol.*, 222: 581–597 (1991) "By–Passing Immunization: Human Antibodies from V–Gene Libraries Displyed on Phage".

Marks et al., *J. Biol. Chem.*, 267(23): 16007–16010 (1992) "Molecular Evolution of Properties on Filamentous Phage".

Martin et al., *Proc. Natl. Acad. Sci. USA*, 86: 9268–9272 (1989) "Modeling Antibody Hypervariable Loops: A Combined Algorithm".

Mathieson et al., *New England J. Med.*, 323 (4): 250–254 (1990) "Monoclonal–Antibody Therapy in Systemic Vasculitis".

McCafferty et al., *Nature*, 348: 552–554 (1990) "Phage Antibodies: Filamentous Phage Displaying Antibody Variable Domains".

Miglietta, et al., *Antibody Engineering Meeting*, Dec. 14–16, 1992 Abstract "Alteration of Framework Residue Modulate Binding of a CDR–Grafted Anti–Human ICAM–1".

Morrison, *Science*, 229: 1202–1207 (1985) "Transfectomas Provide Novel Chimeric Antibodies".

Morrison et al., *Adv. in Immunol.*, 44: 65–92 (1989) "Genetically Engineered Antibody Molecules".

Morrison et al., *Proc. Natl. Acad. Sci.*, 81: 6851–6855 (1984) "Chimeric Human Antibody Molecules: Mouse Antigen–Binding Domains With Human Constant Region Domains".

Munson et al., *Anal. Biochem.*, 107: 220–239 (1980) "Ligand: A Versatile Computerized Approach for Characterization of Ligand–Binding Systems".

Near et al., *J. Immunol.*, 146 (2): 627–633 (1991) "The Specificity Properties that Distinguish Members of a Set of Homologous Anti–Digoxin Antibodies are Controlled by H Chain Mutations".

Nishimura et al., *Eur. J. Immunol.*, 18: 747–753 (1988) "Expression and Function of a CD5 cDNA in Human and Murine T Cells".

Nisonoff et al., *Archives of Biochem.*, 93 460–462 (1961) "Recombination of a Mixture of Univalent Antibody Fragments of Different Specificity".

Novotny et al., *Proc. Natl. Acad. Sci. USA*, 82: 4592–4596 (1985) "Structural Invariants of Antigen Binding: Comparison of Immunoglobulin $V_L$–$V_L$ Domain Dimers".

Novotny et al., *J. Mol. Biol.*, 189: 715–721 (1986) "Location of Antigenic Epitopes on Antibody Molecules".

Novotny et al., *Proc. Natl. Acad. Sci. USA*, 83: 226–230 (1986) "Antigenic Determinants in Proteins Coincide with Surface Region Accessible to Large Probes (Antibody Domains)".

Novotny et al., *Proc. Natl. Acad. Sci. USA*, 83: 742–746 (1986) "Secondary, Tertiary, and Quaternary structure of T–cell–specific Immunoglobulin–like Polypeptide Chains".

Padlan et al., *Proc. Natl. Acad. Sci. USA*, 86: 5938–5942 (1989) "Structure of an Antibody–Antigen Complex: Crystal Structure of the HyHEL–10 Fab–lysozyme Complex".

Padlan, E.A. *Molecular Immunology*, 28(4/5): 489–498 (1991) "A Possible Procedure For Reducing The Immunogenicity of Antibody Variable Domains While Preserving Their Ligand–Binding Properties".

Peacock et al., *Arthritis and Rheumatology*, 35 (Suppl.) Abstract No. B141 (1992) "An Angiogenesis Inhibitor in Combination with Anti–CD5 Mab Suppresses Established Collagen Induced Arthritis Significantly More Than Single Agent Therapy".

Pluckthun, *Biotechnology*, 9: 545–551 (1991) "Antibody Engineering: Advances From the Use of *Escherichia coli* Expression Systems".

Potter et al., *Proc. Natl. Acad. Sci. USA*, 81: 7161–7165 (1984) "Enhancer–dependent Expression of Human K Immunoglobulin Genes Introduced into Mouse pre–B Lymphocytes by Electroporation".

Presta et al., *J. Immun*, 151: 2623–2632 (1993) "Humanization of an Antibody Directed Against IgE".

Queen et al., *Proc. Natl. Acad. Sci. USA*, 86: 10029–10033 (1989) "An Humanized Antibody that Binds to the Interleukin 2 Receptor".

Racadot et al., *Brit. J. Rheumatology*, 30: 88 (1991) Abstract "Immunological Follow Up of 13 Patients With Rheumatoid Arthritis Treated by Anti0T CD4+ Monoclonal Antibodies".

Riechmann et al., *Nature*, 332: 323–327 (1988) "Reshaping Human Antibodies for Therapy".

Roberts et al., *Nature*, 328: 731–734 (1987) "Generation of an Antibody with Enhanced Affinity and Specificity for Its Antigen by Protein Engineering".

Robinson et al., *Hum. antib. Hybridomas*, 2: 84–93 (1991) "Chimeric Mouse–Human Anti–Carcinoma Antibodies that Mediate Different Anti–tumor Cell Biological Activities".

Rodwell, *Nature*, 342: 99–100 (1989) "Engineering Monoclonal Antibodies".

Roguska et al., *Proc. Natl. Acad. Sci. USA*, 91: 969–973 (1994) "Humanization of Murine Monoclonal Antibodies Through Variable Domain Resurfacing".

Rostaing–Capaillon et al., *Cancer Immunol. Immunother.*, 34: 24–30 (1991) "In Vivo Cytotoxic Efficacy of Immunotoxins Prepared From Anti–CD5 Antibody Linked to Ricin A–Chain".

Routledge et al., *Eur. J. Immonl.*, 21: 2717–2725 (1991) "A Humanized Monovalent CD3 Antibody which can Activate Homologous Complement".

Royston et al., *J. Immunol.* 125(2): 725–731 (1980) "Human T Cell Antigens Defined By Monoclonal Antibodies: The 65,000–Dalton Antigen of T Cells (T65) Is Also Found On Chronic Lymphocytic Leukemia Cells Bearing Surface Immunoglobulin".

Schlom, J. *Molecular Foundations of Oncology*, Samuel Broder (Ed.), Williams and Wilkins, Baltimore, MD Chapter 6 pp. 95–134 "Monoclonal Antibodies: They're More and Less Than You Think" (1991).

Sharon et al., *Nature*, 309: 364–367 (1984) "Expression of a $V_H C_K$ Chimeric Protein in Mouse Myeloma Cells".

Shearman et al., *Antibody Engineering Meeting*, Dec. 10–11, 1990 Abstract "Humanized Anitbodies with Specificity for the Human α/β T Cell Receptor".

Shearman et al., *J. Immunol.*, 147(12): 4366–4373 (1991) "Construction, Expression and Cahracterization of Humanized Antibodies Directed Against the Human α/β T Cell Receptor".

Sims et al., *J. Immunol.*, 151(4): 2296–2308 (1993) "A Humanized CD18 Antibody can Block Function Without Cell Destruction".

Singer et al., *J. Immunol.*, 150: 2844–2857 (1993) "Optimal Humanization of 1B4, An Anti–CD18 Murine Monoclonal Antibody, Is Achieved by Correct Choice of Human V–Region Framework Sequences".

Skerra et al., *Science*, 1038–1041 (1988) "Assembly of a Functional Immunoglobulin $F_V$ Fragment in *Escherichia coli*".

Strand et al., *Arthritis and Rheumatism*, 33 (9 Suppl.) (1990) p. S25 "Treatment of rheumatoid Arthritis With An Anti–CD5 Immunoconjugate: Clinical and Immunologic Findings and Preliminary Results of Re–Treatment".

Studnicka, G.M., *Biochem J.*, 252: 825–831 (1988) "*Escherichia coli* Promoter –10 and –35 Region Homologies Correlate with Binding and Isomerization Kinetics".

Takeda et al., *Nature*, 314: 452–454 (1985) "Construction of Chimaeric Processed Immunoglobulin Genes Containing Mouse Variable and Human Constant Region Sequences".

Tempest et al., *Biotechnology*, 9: 266–271 (1991) "Reshaping a Human monoclonal Antibody to Inhibit Human Respiratory Syncytial Virus Infection in vivo".

Thorton, *Nature*, 343: 411–412 (1990) "Tackling a Loopy Problem".

Tramontano et al., *J. Mol. Biol.*, 215: 175–182 (1990) "Framework Residues 71 is a Major Determinant of the Position and Conformation of the Second Hypervariable Region in the $V_H$ Domains of Immunoglobulins".

Tramontano et al., *Proteins: Structure, Function and Genetics*, 6: 382394 (1989) "Structural Determinants of the Conformation of Medium–Sized Loops in Proteins".

Verhoeyen et al., *Science*, 239: 1534–1536 (1988) "Reshaping Human Antibodies: Grafting an Antilysozyme Actvity".

Verhoeyen et al., *BioEssays*,8(2): 74–78 (1988) "Engineering of Antibodies".

Vitetta et al. *Science*, 238: 1098–1104 (1987) "Redesigning Nature's Poisons to Create Anti–Tumor Reagents".

Ward et al., *Nature*, 341: 544–546 (1989) "Binding Activities of a Repertoire of Single Immunoglobulin Variable Domains Secreted from *Escherichia coli*".

Winter et al., *Nature*, 349: 293–299 (1991) "Man–Made Antibodies".

Wofsky et al., *J. Immun.*, 134(2): 852–857 (1985) "Treatment of Murine Lupus with Monoclonal Anti–T Cell Antibody".

Woodle et al., *J. Immunol.*, 148: 2756–2763 (1992) "Humanized OKT3 Antibodies: Successful Transfer of Immune Modulating Properties and Idiotype Expression".

Wu et al., *J. Exp. Med.*, 132: 211–250 (1970) "An Analysis of the Sequences of the Variable Regions of Bence Jones Proteins and Myeloma Light Chains and Their Implications for Antibody Complementary".

Wu and Kabat., *Mol. Immunol.*, 29(9): 1141–1146 (1992) "Possible Use of Similar Framework Region Amino Acid Sequences Between Human and Mouse Immunoglobulins for Humanizing Mouse Antibodies".

Ahmed, *Bioessays*, "Structure and Function of Chimaeric Anitbodies," 6 (4):175–177, 1986.

Antin, et al., *Blood*, "Selective Depletion of Bone Marrow T Lymphocytes With Anti–CD5 Monoclonal Antibodies: Effective Prophylaxis for Graft–Versus–Host Disease in Patients With Hematologic Malignancies," 78: 2139–2149 (Oct. 15, 1991).

Better et al., *Science*, "*Escherichia coli* Secretion of an Active Chimeric Antibody Fragment," 240: 1041–1043 (May 20, 1988).

Gillam et al., *Gene*, "Site–Specific Mutagenesis Using Synthetic Oligodeoxyribonucleotide Primers: I. Optimum Conditions and Minimim Oligodeoxyribo–Nucleotide Length," 8: 81–97 (1979).

Kabat et al., *Sequences of Proteins of Immun. Interest*, Fourth Edition, US Dept. of Health and Human Services, Public Health Sevice, Nat. Inst. of Health (1987).

Sinha et al., *Nucleic Acids Res.*, "Polymer support oligonucleotide synthesis XVIII[1,2]: use of β–cyanoethyl–N, N–dialkylamino–/N–morpholino phosphoramidite of deoxynucleosides for the synthesis of DNA fragments simplifying deprotection and isolation of the final product," 12: 4539–4557 (1984).

Thorpe et al., Monoclonal Abs in Clinical Medicine Farbe JW Eds*, "Monoclonal Antibody–Toxin Conjugates: aiming the magic bullet," 168–201 Academic Press NY 1982.

Queen, C., et al. Proc. Natl. Acad. Sci., U.S.A. 86:10029–10033, Dec. 1989.

Shawler, D.L. e tal. J. Biological Response Modifers. 7:608–618, 1988.

FIG. 1A

LIGHT CHAIN

```
pos             10         20        x  30x       40                50
HYH    DIVLTQS PATLSVTPGNSVSLSCRASQS    IG NNLHWYQQKSHESPRLLIK       YAS
MCPC   DIVMTQS PSSLSVSAGERVTMSCKSSQS    LL!NFLAWYQQKPGQPPKLLIY       GAS
NEWM   XSVLTQ  PPSVSGAPGQRVTISCTGSSSN   IG!NHVKWYQQLPGTAPKLLIF
KOL    QSVLTQ  PPSASGTPGQRVTISCSGTSSN   IGSSTVNWYQQLPGMAPKLLIY       RAD
bind   +-+O++  O++O++++O+-+++++-+-O-  -----O-O+++O+-OO-              ---
bury   +-+-+-+ O++O+-++++-+-+-+-+++   -++++-!=-O=O=--O               +++
risk     ●■■   ▲●■▲●■▲■●●■●●■■●■■■■▲●  ▲▲●■●●■■▲●▲■■
mod           ●       ●●              ● pos            60          70         80          90       x      100
HYH    QSISGIPSRFSGSG SGT DFTLSINSVETEDFGMYFCQQS NS    WPYT FGGGTKLDIK
MCPC   TRESGVPDRFTGSG SGT DFTLTISSVQAEDLAVYYCQND HS    YPLT FGAGTKLEIK
NEWM   HNNA   RFSVSK SGS SATLAITGLQAEDEADYYCQSY DR     SLRV FGGGTKLTVL
KOL    MRPSGVPDRFSGSK SGA SASLAIGGLQSEDETDYYCAAW DV!   NAYV FGTGTKVTVL
bind   -+OO++O++-+-+- +O+ +--++++++++-O--         ---  ---O O+++++++++
bury   ++O++-O+O-+-+- +-+ +-++-+-+++-+----!=!=!   ++O  OO= =-+-+-+++
risk   ■●▲▲●▲●■▲●■●   ●■● ●●■■●●■■●●■■▲■●■■▲       ●■   ■●■ ■●■■■●●
mod    ●                  ●●●                                 ●   ●●
```

HEAVY CHAIN

```
pos            10              20        30        40        50 x
HYH   DVQLQESGPS LVKPSQTLSLTCSVTG DSITSDYWSWIRKFPGNRLEYMGYVS YSGST
MCPC  EVKLVESGGG LVQPGGSLRLSCATSG FTFSDFYMEWVRQPPGKRLEWIAASR!NKYTT
NEWM  QVQLEQSGPG LVRPSQTLSLTCTVSG TSFDDYYSTWVRQPPGRGLEWIGYVF YHGTS
KOL   EVQLVQSGGG VVQPGRSLRLSCSSSG FIFSSYAMYWVRQAPGKGLEWVAIIWDDGSDQ
bind  O-+O++++O+ +++O++++++++-+OO- ---------O-O+++O+++O+-OO---------
bury  +-+-+-+-O+ +O+++++-+-+-+-+- -+-++O+-=-=O=++++O=O=--O-O+++O++
risk  ▲■●■●■●■▲● ●▲●▲●●●■●■●■●■▲■ ■■■■■■■■■■■■▲■●▲●●▲■▲■■■■■■■■■■■■■
mod     ● ● ●  ● ●  ● ●●● ● ● ●                ● ●● pos     60         70        80 abc      90        x100a      110
HYH   YYNPSLKSRISITRDTSKNQYYLDLNSVTTEDTATYYCANWD     GDYWGQGTLVTVSA
MPCP  EYSASVKGRFIVSRDTSQSILYLQMNALRAEDTAIYYCARNYY ! WYFDVWGAGTTVTVSS
NEWM  DTDTPLRSRVTMLVNTSKNQFSLRLSSVTAADTAVYYCARNLIA  GCIDVWGQGSLVTVSS
KOL   HYADSVKGRFTISRNDSKNTLFLQMDSLRPEDTGVYFCARDGG ! FGPDYWGQGTPVTVSS
bind  -OOOO+O++++-+-+O++O+-+++++++++++++++-O------ -----O+++++++++
bury  +O-+O-++O-+-+-+O++O+-+-+-++-+++-+-O-=-=-=OO+O OO=OO=-+--+-+-++
risk  ■▲■▲▲■▲●▲■●■●■●▲●●▲●■●■●■●●■●●●■●■▲■■■■■■■■■■ ■■■■■■■●■■●■●■●●
mod          ●  ● ● ● ●● ● ● ● ●● ●●● ●                ●  ● ● ●●
```

FIG. 1B

LIGHT CHAIN

```
pos           10         20      x  30x         40              50
bind   +-+o+++ o+++++++o+++++++-+-o-- ------o-o+++++o+-oo- ---
bury   +-+-+-+ o++o+-+++++++-+-+++ -+++-=-=o=++++o=o=--o +++
risk   •••■• ▲•■■ ■•■■ ■■■■■■■■■■■■▲■•▲ ■
mod    •• •• •• •    •  ••▲•    •
hK1    DIQMTQS PSSLSASVGDRVTITCrASQx      Is xyLxWYQQKPGkAPkLLIY      aAS
hK3    EIVLTQS PgTLSlSPGERATLSCRASQS      vsssyLAWYQQKPGQAPRLLIY      gaS
hK2    DIVMTQS PLSLPVTPGEPASISCRSSQS      LlnnYLnWYLQKPGQSPqLLIY      lgS
hL1    xSVLTQP PS  aSgtPGQrVtISCsGssS     iGxnxVxWYQqlPGtAPKLLIY      n n
hL2    XSALTQP aS  VSGSPGQSiTISCtGtss     VgYnxVSWyQQhPGkAPK  LIY     dv
hL3    SYeLTQP PS  vSVsPGQTA  ITCsGdx     lxxxyvxWYQQkPgQaPvLVIy      d
hL6    nfmltqp hs  vsespgktvtisctxsxg     iasxyvqwyqqrpgsapttviy      edn
hK4    divmtqs pdslavslgeratinckssgs      vlknylawyqqkpgqppkllix      was
hL4    seltqp  ps  vsvapgqt ritcsgdx      lgxydaxwyqqkpgqaplIviy      grn
hL5    saltqp  ps  asgspggqsvtisctgtss    vgxxyvswyqqh g apk   i      ev
```

FIG. 5A

HEAVY CHAIN

```
pos              10              20              30              40              50    x
bind   o-+o++++o+    +++o++++++++too-   -----o-o-o++++++oo-    -+-+o++-=-=o=++++o+-oo-----    -o-o+++o++
bury   +-+-+-o+      +o++++++-+-+-+-    -+-+o++-=-=o=++++o+
risk   ▲■●▲          ●▲▲●●▲●            ■                                                                ■
mod                    ●                 ●                       ● ●●
hH3    EVQLvESGGG   LVqPGGSLRLSCAASG   FtFsxxxmxWRQApGKgLEWV xxixxxxxgx
hH1    QVqLvqSGaE   VkKPGxSvxvSCKxSG   YyFxxyxixWvRQaPGxGLEWvGxixpxxgxt
hH2    xvtlxesgpx   lvlptqtltlctvsg    xslsxxxvxwirqppgkxlewlaxix   xddd pos    60              70              80  abc         90              x100a           110
bind   -oooo+o+++-+--+o++o+o++++o+++    -+++++++++o+++++-o+++-o-++o     -----o-------  ----O++++++++
bury   +o-+o-++o+--+-+o++o+-+-+-+-     -+++-++-+-+-+--+-+--+++---=o     oo=oo=-+--+-+++
risk   ■▲■▲▲▲■▲●■     ▲▲■●▲●■         ▲ ●●●●●●●●●●●●●●■■●●■               ■■
mod          ●         ●                    ●                                         ●
hH3    xyadSVkGRFTISRddSKNtlyLqMnsLraeDTAvYYCarxxxxx   xxxxxWGqGTlVTvSS
hH1    xyapxfggRVTxtrdxSxntayMeLxsLrseDtAvYYCArxxxxx   xxxxxwggGtlvtvSS
hH2    xyxtslrsrltiskdtsknqvvlxxxxxdpxdtatyycarxxxxx   xxxdv

FIG. 6A

LIGHT CHAIN

```
pos           10         20        x  30x       Is  xyLxWYQQKPGkAPkllIY  50   aAS
hK1    DIQMTQS PSSLSASVGDRVTITCrASQx     IN  SYLSWFQQKPGKSPKTLIY       RAN
H65    DIKMTQS PSSMYASLGERVTITCKASQD
bind    ++-+o++   o++++++o++++++-+-o--   -+----o-o++++o++-oo-          ---
bury    -+-+-+    o++o+-++++++++-+-+-++   -+++++-==+o=o=--o             +++
risk   •▲•••▲•■■ •▲•••▲••■••••••••■■■■   •■■■■■■■■■■■•▲•■■■■■           ■■
mod        •                       •         ••
M/H         H      MH  M  H         h   M          M                M M
prop   DIQMTQS PSSMSASLGDRVTITCRASQD     IN  SYLSWFQQKPGKSPKTLIY      RAN pos              60          70           80          90       x       100
hK1      xLxsGVPSRFsGSG SGT xFTITlSsLQpeDfATYYCqqy    xx     xPxt  FGqGTkveik
H65      RLVDGVPSRFSGSGG SGQ DYSLTISSLDYEDMGIYYCQQY   DE     SPWT  FGGGTKLEIK
bind     -+oo+++o+-+-     +o+   +-++-++++++++++-o--   ---    ---o  o++++++++
bury     ++o++-o+o-+-+-   +-+  ++-+-+-+++++-+++-+-=   ==    oo=-   =-+-+-+++
risk    ■•▲▲•■■▲•••■•   •▲■  ■■■■■■■■■■■■■■■■■■■■   ■■    ■■■■   •■•■■■••
mod          •                               •                        ••    m
M/H     M  MM                H   mMH         Hm hMM    MM  M M           M
prop     RLVDGVPSRFSGSG SGT DYTLTISSLQYEDFGIYYCQQY    DE     SPWT  FGGGTKLEIK
```

HEAVY CHAIN

```
pos              10           20                30         40         50 x
hH3     EVQLvESGGG LVqPGGSLRLSCAASG FtFsxxxmxWVRQApGKgLEWVxxixxkxxgx
h65     QIQLVQSGPE LKKPGETVKISCKASG YTFTNYGMNWVKQAPGKGLRWMGWINTHTGEP
bind    o-+o++++o+ +++o++++++++-+oo- --------o-o+++o+++o+-oo---------
bury    +-+-+-+-o+ +o++++++-+-+-+-+- -+-++o+-=-=o=++++o=o=--o-o+++o++
risk    ▲■●■●■●■▲● ●▲●▲●●●■●■●■●■▲■ ■■■■■■■■■■■■▲■●▲●●▲■▲■■■■■■■■■■■■■
mod      ● ● ●  ● ● ● ●●● ● ● ●                      ● ●●
M/H     MM   M MH   Mm HHMHM  H    M  MMMM M  M         M MMM MMMMMMM
prop    QIQLVQSGPG LKKPGGSVRISCAASG YTFTNYGMNWVKQAPGKGLRWMGWINTHTGEP pos      60         70       80  abc      90      x100a       110
hH3     xyadSVkGRFTISRddSKNtlyLqMnsLraeDTAvYYCarxxxx xxxxxWGqGTlVTvSS
H65     TYADDFKGRFAFSLETSASTAYLQINNLKNEDTATYFCTRRGYD WYFDVWGAGTTVTVSS
bind    -oooo+-++++-+-+o++o+-+++++++++++++++-o------ -----o++++++++++
bury    +o-+o-++o-+-+-+o++o+-+-+-++-+++-+-o-=-=-=oo+o oo=oo=-+--+-+-++
risk    ■▲■▲▲■▲●▲■●■●■●▲●●▲●■●■●■●●■●●●■●■▲■■■■■■■■■■■ ■■■■■■●■■●■●■●●
mod         ●  ● ● ● ●● ● ● ● ●● ●●● ●                   ●  ● ● ●●
M/H     M  MM    HM MhM HM M   M h hh    M M M MMMM MMMMM  h  m
prop    TYADDFKGRFTFSLDTSKSTAYLQINSLRAEDTATYFCTRRGYD WYFDVWGQGTTVTVSS
```

FIG. 6B

```
SH65K-1
AGT CGT CGA CAC GAT GGA CAT GAG GAC CCC TGC TCA GTT TCT TGG CAT CCT CCT ACT
CTG GTT TCC AGG TAT CAA ATG TGA CAT CCA GAT GAC TCA GT

HUH-K1
TGA CTC GCC CGG CAA GTG ATA GTG ACT CTG TCT CCC AGA GAT GCA GAC ATG GAA GAT
GAG GAC TGA GTC ATC TGG ATG TC

HUH-K2
TCA CTT GCC GGG CGA GTC AGG ACA TTA ATA GCT ATT TAA GCT GGT TCC AGC AGA AAC
CAG GGA AAT CTC CTA AGA CCC T

HUH-K3
GAT CCA CTG AAC CTT GAT GGG ACC CCA TCT ACC AAT CTG TTT GCA CGA TAG
ATC AGG GTC TTA GGA GAT TTC C

HUH-K4
GGT TCA GTG GCA GTG GAT CTG GGA CAG ATT ATA CTC TCA CCA TCA GCA GCC TGC AAT
ATG AAG ATT TTG GAA TTT ATT G

HUH-K5
GTT TGA TTT CAA GCT TGG TGC CTC CAC CGA ACG TCC ACG GAG ACT CAT CAT ACT GTT
GAC AAT AAT AAA TTC CAA AAT CTT C

HUH-G1
TGT CGA CAT CAT GGC TTG GGT GTG GAC CTT GCT ATT CCT GAT GGC AGC TGC CCA AAG
TGC CCA AGC ACA GAT GTT GGT GCA G

HUH-G2
AAG GTA TAC CCA GAA GCT GCG CAG GAG ATT CTG ACG GAC CCT CCA GGC TTC TTC AGG
CCA GGT CCA GAC TGC ACC AAC TGG ATC T
```

FIG. 7A-1

HUH-G3
GCA GCT TCT GGG TAT ACC TTC ACA AAC TAT GGA ATG AAC TGG GTG AAG CAG GCT CCA
GGA AAG GGT TTA AGG TGG ATG GGC TGG

HUH-G4
AAA GAG AAG GTA AAC CGT CCC TTG AAG TC A TCA GCA TAT GTT GGC TCT CCA GTG TGG
GTG TTT ATC CAG CCC CAC CTT AAA C

HUH-G5
CAC GGT TTA CCT TCT CTT TGG ACA CGT CTA AGT GCA CTG CCT ATT TAC AGA TCA ACA
GCC TCA GAG CCG AGG ACA CGG CTA CAT

HUH-G6
AGG AGA CGG TGA CCG TGG TCC CTT GGC CCC AGA CAT CGA AGT ACC AGT CGT AAC CCC
GTC TTG TAC AGA AAT ATG TAG CCG TGT CCT CGG C

H65G-2S
ACT AGT GTC GAC ATC ATG GCT TGG GT

H65-G2
GAG GAG ACG GTG ACC GTG GT

H65K-2S
AGT CGT CGA CAC GAT GGA CAT GAG GAC

JK1-HindIII
GTT TGA TTT CAA GCT TGG TGC

HUH-G11
TGT CGA CAT CAT GGC TTG GGT GTG GAC CTT GCT ATT CCT GAT GGC AGC TGC CCA AAG
TGC CCA AGC AGA GAT CCA GTT GGT GCA G

HUH-G14
AAA GAG AAG GTA AAC CGT CCC TTG AAA GAA TCA GCA TAT GTT GGC TCT CCA GTG TGG
GTG TTT ATC CAG CCC CAC ATG TCT AAA C

HUH-G13
GCA GCT TCT GGG TAT ACC TTC ACA AAC TAT GGA ATG AAC TGG GTG CGC CAG GCT CCA
GGA AAG AAT TTA GAG TGG ATG GGC TGG

HUH-G16
GAG GAG ACG GTG ACC GTC CCT TGG CCC CAG ACA TCG AAG TAC CAG TCG TAA CCC
CGT CTT GTA CAG AAA TAC ACA GCC GTG TCC TCG GC

HUH-G15
GAC GGT TTA CCT TCT CTT TGG ACG ATT CTA AGA ACA CTG CCT ATT TAC AGA TCA ACA
GCC TCA GAG CCG AGG ACA CGG CTG TGT ATT

HUH-G12
AAG TAC CCA GAA GCT GCG CAG GAG ATT CTG ACG GAC CCT CCA GGC TTC ACC AGG
CCT CCT CCA GAC TGC ACC AAC TGG ATC TC

HUH-K6
TCA CTT GCC GGG CGA ATC AGG ACA TTA ATA GCT ATT TAA GCT GGT TCC AGC AGA AAC
CAG GGA AAG CTC CTA AGA CCC T

HUH-K8
GAT CCA CTG CCA AAC CTT GAT GGG ACC CCA GAT TCC AAT CTG TTT GCA CGA TAG
ATC AGG GTC TTA GGA GCT TTC C

HUH-K7
TGA CTC GCC CGG CAA GTG ATA GTG ACT CTG TCT CCT ACA GAT GCA GAC AGG GAA GAT
GGA GAC TGA GTC ATC TGG ATG TC

```
              10         20         30         40         50
              |          |          |          |          |
ACTAGTGTCG ACATCATGGC TTGGGTGTGG ACCTTGCTAT TCCTGATGGC

AGCTGCCCAA AGTGCCCAAG CACAGATCCA GTTGGTGCAG TCTGGACCTG

GCCTGAAGAA GCCTGGAGGG TCCGTCAGAA TCTCCCTGCGC AGCTTCTGGG

TATACCTTCA CAAACTATGG AATGAACTGG GTGAAGCAGG CTCCAGGAAA

GGGTTTAAGG TGGATGGGCT GGATAAACAC CCACACTGGA GAGCCAACAT

ATGCTGATGA CTTCAAGGGA CGGTTTACCT TCTCTTTGGA CACGTCTAAG

AGCACTGCCT ATTTACAGAT CAACAGCCTC AGAGCCGAGG ACACGGCTAC

ATATTTCTGT ACAAGACGGG GTTACGACTG GTACTTCGAT GTCTGGGGCC

AAGGGACCAC GGTCACCGTC TCCTC
```

FIG. 8A

```
            10          20          30          40          50
             |           |           |           |           |
AGTCGTCGAC ACGATGGACA TGAGGACCCC TGCTCAGTTT CTTGGCATCC
TCCTACTCTG GTTTCCAGGT ATCAAATGTG ACATCCAGAT GACTCAGTCT
CCATCTTCCA TGTCTGCATC TCTGGGAGAC AGAGTCACTA TCACTTGCCG
GGCGAGTCAG GACATTAATA GCTATTTAAG CTGGTTCCAG CAGAAACCAG
GGAAATCTCC TAAGACCCTG ATCTATCGTG CAAACAGATT GGTAGATGGG
GTCCCATCAA GGTTCAGTGG CAGTGGATCT GGGACAGATT ATACTCTCAC
CATCAGCAGC CTGCAATATG AAGATTTTGG AATTTATTAT TGTCAACAGT
ATGATGAGTC TCCGTGGACG TTCGGTGGAG GCACCAAGCT TGAAATCAAA
```

FIG. 8B

LIGHT CHAIN

```
pos                       10              x  30x       40                50
EU     DIQMTQS PSTLSASVGDRVTITCRASQS  IN TWLAWYQQKPGKAPKLLMY             KAS
hK1    DIQMTQS PSSLSASVGDRVTITCRASQx  Is syLxWYQQKPGKAPKILIY             aAS
TAC    QIVLTQS PAIMSASPGEKVTITCSASSS  IS YMHWFQQKPGKRGTSPKLWIY           TTS
bind   +-+0+++  0+++++++++-+-0--      ------0-0++0++++0+--00-            ---
bury   +-+-+-+  0++0+-+++++-+-++++-   -+++++=-==0=++++0=0=--0            +++
risk   ●●▲●■    ▲●●■        ●●       -++++■■■■■■■■■■▲▲▲●▲▲●■            ■■■
mod                                              ●●
M/H    H HM     HHM         M HH     h   M        hM                    MM
prop   DIQLTQS  PSSMSASPGDRVTITCRASSS IS YMHWFQQKPGKSPKLWIY             TTS
Que    DIQMTQS  PSTLSASVGDRVTITCSASSS IS YMHWYQQKPGKAPKLLIY             TTS pos           60                 70              80                   90       x    100
EU     SLESGVPSRFIGSG SGT EFTLTISSLQPDDFATYYCQQY NS DSKM FGQGTKVEVK
hK1    xLxsGVPSRFsGSG SGT xFTlTIsSLQpeDfATYYCqqy xx xPxt FGqGTkveik
TAC    NLASGVPARFSGSG SGT SYSLTIISRMEAEDAATYYCHQR ST YPLT FGSGTKLELK
bind   -+00++0++0-+-   +0+ +-+++++++-0--         ---  ---0 0++++++++++
bury   ++0++-0+0-+-+-  +-+ +-+-+-+++-+-==-==-=   ++0  00=- =-+-+-+++
risk   ■●▲▲■●▲●▲■●     ■●  ●●●●●■■■■■■■■■■■■■■■  ●●■  ●●■■ ■●●■■●●●
mod                                                      ●         ● ●●
M/H    M M   H         mMH              hMHm h   M M MM  M M        h  M  m
prop   NLASGVPSRFSGSG SGT SYTLTISSMQAEDFATYYCHQR ST YPLT FGQGTKLELK
Que    NLASGVPARFSGSG SGT EFTLTISSLQPDDFATYYCHQR ST YPLT FGQGTKVEVK
```

HEAVY CHAIN

```
pos                10                  20              30              40              50        x
EU         QVQLVQSGAE         VKKPGSSVKVSCKASG   GTFSRSAIIWVRQAPGQGLEWMGGIVPMFGPP
hH1        QVqLvqSGaE         VkKPGxSvxvSCKxSG   yyFxxyxixWvRQaPGxGLEWvGxixpxxgxt
TAC        QVQLQQSGAE         LAKPGASVKMSCKASG   YTFTSYRM FIG. 13A
FIG. 13B
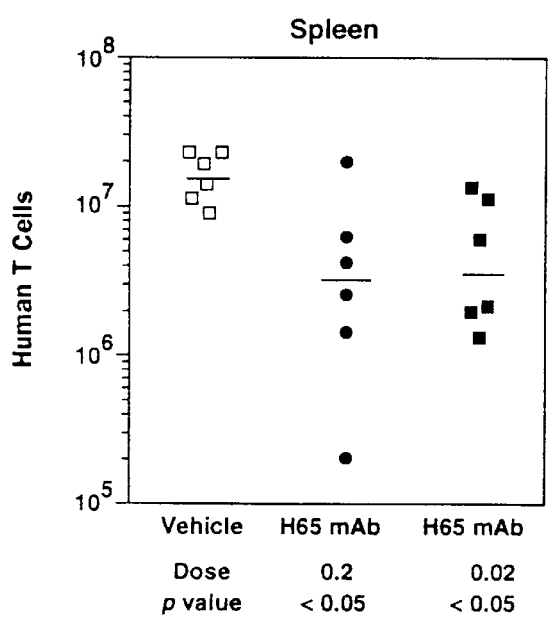
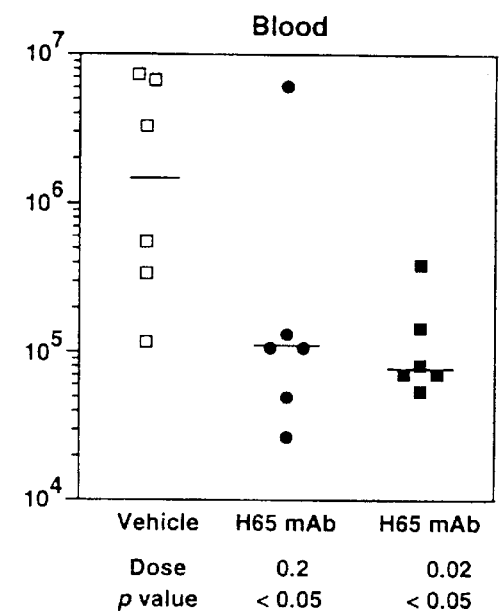

LIGHT CHAIN

```
pos              10         20        x  30x         40                50
H65    DIKMTQS PSSMYASLGERVTITCKASQD  IN SYLSWFQQKPGKSPKTLIY           RAN
bind   +-+o+++  o++++++++o++++++++-+-  ----o-o++++o+++o+-oo-           ---
bury   +-+-+-+  o++o+-+++++-+-+-+++-   -+++-+-=-=o=++++o=-o            +++
risk   ●■●■■    ▲●●▲●●●■●■■●■▲▲■■      ■■■■■■■■■■■▲■▲●●▲■▲■            ■
hK1    DIQMTQS PSSLSASVGDRVTITCRrASQx  Is  xyLxWYQQKPGkAPkLLIY          aAS
M/H       ^      H^ H^                      ^         H    M            M M
prop   DIQMTQS PSSLSASVGDRVTITCRASQD   IN SYLSWFQQKPGKAPKTLIY           RAN pos              60         70        80             90      x     100
H65    RLVDGVPSRFSGSG SGQ DYSLTITISSLDYEDMGIYYCQQY  DE        SPWT  FGGGTKLEIK
bind   -+oo++o++-+--  +o+ +-+++++-+++-++++++++-o-- --         --o  o++++++++-  ●
bury   ++o++--o+o-+-+- +-+ +-+-+-+++-+++●●+●++-+=-=  ++o      oo=  =-+-+-+++  ●
risk   ●▲▲▲■■▲●▲■■●■  ●■● ●■●■■■●■●■●●■●■●●■●■■■■■  ■         ■    ■●■■■■■■■  ●
hK1    xLxsGVPSRFsGSG SGT xFTlTISsLQpeDfATYYCqqy     xx       xPxt FGqGTkveik
M/H    M hh            ^    ^M^                 ^MM  MM            ^      M
prop   RLESGVPSRFSGSG SGT DYTLTISSLQYEDFGIYYCQQY   DE          SPWT FGGGTKLEIK
```

FIG. 16A

HEAVY CHAIN

```
pos              10         20         30         40         50      x
H65    QIGLVQSGPE LKKPGETVKISCKASG YTFTNYGMNWVKQAPGKGLRWMGWINTHTGEP
bind   o-+o+++o+  +++o++++++-+-++-  -------o-o+++o+++o+-oo-----
bury   +-+-+--o+  +o++++++-+-+-+-   -+--++o+--=-=o=++++o=o=--o-o+++o++
risk   ▲●■●■▲●    ●▲●▲●●▲■●▲●     ■■■■■■■■▲■●▲●▲■▲●●▲■▲●■■■■
hH3    EVQLvESGGG LVqPGGSLRLSCAASG FtFsxxxmxWVRQapGKgLEWVxxixkkxxgx
M/H    HM   M  H^ H^ ^M^M  ^       M  MMMM M  H      H  HmM MMMMMM
prop   EIQLVQSGGG LVKPGGSVRISCAASG YTFTNYGMNWVRQAPGKGLEWMGWINTHTGEP pos        60         70    abc   80         90    x100a      110
H65    TYADDFKGRFAFSLETSASTAYLQINNLKNEDTATYFCTRRGYD  WYFDVWGAGTTVTVSS
bind   -oooo+o+++++-+--+o++o+-++++++++++++++++-o-----  -----o++++++++++
bury   +o--+o-++o++o-+--+o++o+-+-+-+++++++++-+-o-=-==oo=oo+o  oo=oo=-+-+--++
risk   ■▲■▲▲▲▲■●▲▲●■▲■▲●■■■■■●●▲●▲●■▲■▲■●▲■■▲■  ■■■■■●■■●●
hH3    xyadSVkgRFTISRddSKNtlyLqMnsLraeDTAvYYCarxxxx  xxxxxWGqGTlVTvSS
M/H    M  HM  ^M M^h ^H M  M ^  ^^            h M  MMMM    MMMM  ^
prop   TYADSFKGTRTFSLDDSKNTAYLQINSLRAEDTAVYFCTRRGYD  WYFDVWGQGTTVTVSS
```

FIG. 16B

MODIFIED ANTIBODY VARIABLE DOMAINS

CROSS REFERENCE TO RELATED APPLICATIONS

This application is a continuation-in-part of international stage application PCT/US92/10906, filed Dec. 14, 1992 (abandoned), which is a continuation-in-part of U.S. application Ser. No. 07/808,464, filed Dec. 13, 1991 (abandoned).

FIELD OF THE INVENTION

The present invention generally relates to modified antibody variable domains and fragments thereof. More particularly, the invention relates to mouse antibody variable domains which are modified for administration to humans. For purposes of the present application, such modified antibody variable domains are termed "humanized antibodies" or "human-engineered antibodies." As taught herein, the humanized antibodies, or fragments thereof, according to the invention are useful, either alone or in conjugated form, in the treatment of various human diseases. The present application also teaches methods, termed "human-engineering," for preparing humanized antibodies, conjugation of humanized antibodies to various toxins, and therapeutic uses of the humanized antibodies of the invention.

BACKGROUND OF THE INVENTION

Application of unmodified mouse monoclonal antibodies in the treatment of human diseases may be problematic for several reasons. First, an immune response against the mouse antibodies may be mounted in the human body. Second, the mouse antibodies may have a reduced half-life in the human circulatory system. Third, the mouse antibody effector domains may not efficiently trigger the human immune system.

Several reports relate to eliminating the foregoing problems. For example, Junghans et al., *Cancer Res.*, 50:1495–1502 (1990), describe the utilization of genetic engineering techniques to link DNA encoding murine variable domains to DNA encoding human constant domains, creating constructs which, when expressed, generate a hybrid mouse/human chimeric antibody.

Also by genetic engineering techniques, the genetic information from murine hypervariable complementarity determining regions (hereinafter referred to as "CDRs") may be inserted in place of the DNA encoding the CDRs of a human monoclonal antibody to generate a construct encoding a human antibody with murine CDRs. This technique is known as "CDR grafting". See, e.g., Jones et al., *Nature*, 321, 522–525 (1986); Junghans et al., supra.

Protein structure analysis may be used to "add back" murine residues, again by genetic engineering, to first generation variable domains generated by CDR grafting in order to restore lost antigen binding capability. Queen et al., *Proc. Natl. Acad. Sci.* USA, 86, 10029–10033 (1989); Co, et al., *Proc. Natl. Acad. Sci.* USA, 88, 2869–2873 (1991) describe versions of this method. The foregoing methods represent techniques to "humanize" mouse monoclonal antibodies.

As a result of the humanization of mouse monoclonal antibodies, specific binding activity of the resulting humanized antibodies may be diminished or even completely abolished. For example, the binding affinity of the modified antibody described in Queen et al., supra, is reported to be reduced three-fold; in Co et al., supra, is reported to be reduced two-fold; and in Jones et al., supra, is reported to be reduced two- to three-fold. Other reports describe order-of-magnitude reductions in binding affinity. See, e.g., Tempest et al., *Bio/Technology*, 9:266–271 (1991); Verhoeyen et al., *Science*, 239:1534–1536 (1988).

Examples of therapeutic targets for antibody therapy in humans are T lymphocytes, or T cells. Various T cell-reactive antibodies have been described, primarily from murine hybridomas. The specific subsets of T cells recognized by these antibodies, and their cell surface targets, are differentiated by the Clusters of Differentiation System (hereinafter referred to as the "CD System"). The CD System represents standard nomenclature for molecular markers of leukocyte cell differentiation molecules. See Leukocyte Typing III White Cell Differentiation Antigens (Michael, ed. Oxford Press 1987), which is incorporated by reference herein.

So-called "pan T cell" markers (or antigens) are those markers which occur on T cells generally and are not specific to any particular T cell subset(s). Pan T cell markers include CD2, CD3, CD5, CD6, and CD7.

The CD5 cluster antigen, for example, is one of the pan T cell markers present on about 85–100% of the human mature T lymphocytes and a majority of human thymocytes. The CD5 marker is also present on a subset, about 20%, of B cells. Extensive studies using flow cytometry, immunoperoxidase staining, and red cell lysis have demonstrated that CD5 is not normally present on hematopoietic progenitor cells or on any other normal adult or fetal human tissue with the exception of the aforementioned subpopulation of B cells.

Further information regarding the CD5 marker is found in McMichael and Gotch, in *Leukocyte Typing III White Cell Differentiation Antigens* (Michael, ed. Oxford Press 1987). The CD5 molecule has also been described in the literature as reactive with immunoglobulins. See, e.g., Kernan et al., *J. Immunol.*, 33:137–146 (1984), which is incorporated by reference herein.

There are reports of attempted treatment of rheumatoid arthritis patients with monoclonal antibodies against CD4. See Horneff, et al. *Arthritis and Rheumatism* 34:2, 129–140 (February 1991); Goldberg, et al., *Arthritis and Rheumatism*, Abstract D115, 33:S153 (September 1990); Goldberg, *Journal of Autoimmunity*, 4:617–630 (1991); Choy, et al. *Scand. J. Immunol.* 36:291–298 (1992).

There are reports of attempted treatment of autoimmune disease, particularly rheumatoid arthritis, with an anti-CD7 monoclonal antibody. See Kirkham, et al., *British Journal of Rheumatology* 30:459–463 (1991); Kirkham, et al., *British Journal of Rheumatology* 30:88 (1991); Kirkham, et al., *Journal of Rheumatology* 19:1348–1352 (1992). Lazarovits, et al., *J. Immunology*, 150:5163–5174 (1993), describe attempted treatment of kidney transplant rejection with a chimeric anti-CD7 antibody. There is also a report of an attempt to treat multiple sclerosis with an anti-T12 antibody and a pan T- cell antibody (anti CD-6). Hafler, et al. , *Neurology* 36:777–784 (1986).

None of the above attempts for therapy of human autoimmune diseases involve the use of unconjugated anti-CD5 antibodies.

Thus, there exists a need for the successful antibody therapy of T cell-mediated diseases such as autoimmune disease, graft-versus-host disease, and transplant rejection. As demonstrated by the foregoing, there also exists a need in the art for methods for the preparation of humanized antibodies useful in the treatment of various human diseases and not subject to the foregoing drawbacks.

SUMMARY OF THE INVENTION

The present invention provides methods, termed human-engineering, for preparing a modified antibody variable domain useful for administration to humans by determining the amino acids of a subject antibody variable domain which may be modified without diminishing the native affinity of the domain for antigen, while reducing its immunogenicity with respect to a heterologous species. As used herein, the term "subject antibody variable domain" refers to the antibody upon which determinations are made. The method includes the following steps: determining the amino acid sequence of a subject light chain and a subject heavy chain of a subject antibody variable domain to be modified; aligning by homology the subject light and heavy chains with a plurality of human light and heavy chain amino acid sequences; identifying the amino acids in the subject light and heavy chain sequences which are least likely to diminish the native affinity of the subject variable domain for antigen while, at the same time, reducing its immunogenicity by selecting each amino acid which is not in an interface region of the subject antibody variable domain and which is not in a complementarity-determining region or in an antigen-binding region of the subject antibody variable domain, but which amino acid is in a position exposed to a solvent containing the antibody; changing each residue identified above which aligns with a highly or a moderately conserved residue in the plurality of human light and heavy chain amino acid sequences if said identified amino acid is different from the amino acid in the plurality.

Another group of sequences, such as those in FIGS. 1A and 1B may be used to determine an alignment from which the skilled artisan may determine appropriate changes to make.

The present invention provides a further method wherein the plurality of human light and heavy chain amino acid sequences is selected from the human consensus sequences in FIGS. 5A and 5B.

In general, human engineering according to the above methods may be used to generate antibodies useful in the treatment of various diseases against which monoclonal antibodies generally may be effective. However, humanized antibodies possess the additional advantage of reducing the immunogenic response in the treated patient in the same manner and potentially to a greater extent than observed for chimeric antibodies (see LoBuglio, et al, *Proc Natl. Acad. Sci. USA*, 86:4220–4224 (1989) and Brüggemann, et al., *J. Exp. Med.*, 170:2153–2157 (1989).

The present invention also discloses products and pharmaceutical compositions useful in the treatment of myriad human diseases which may be targeted by an antibody. In particular, products prepared by the foregoing methods include a modified H65 mouse monoclonal variable domain. Additionally, DNA sequences encoding the modified H65 variable domain are provided.

Modified antibody variable domains which are products of the methods of the present invention may be used, inter alia, as components of various immunoglobulin molecules such as Fab, Fab', and F(ab')$_2$ domains, single chain antibodies, and Fv or single variable domains.

The present invention provides novel proteins comprising a human-engineered antibody variable domain which are specifically reactive with a human CD5 cell differentiation marker. Preferred human-engineered anti-CD5 antibodies according to the present invention may have a binding affinity for CD5 of less than $2 \times 10^{-9}$M. In a preferred embodiment, the present invention provides proteins comprising the he3 light and heavy chain variable regions as shown in SEQ ID NOS: 73 and 74, respectively. DNA encoding certain he3 proteins is shown in SEQ ID NOS: 75 and 76.

In a preferred embodiment of the present invention, the protein comprising a human-engineered antibody variable region is an intact he3 immunoglobulin deposited with the American Type Culture Collection, 10801 University Boulevard, Manassas, Va. 20110-2209 as ATCC Accession No. HB 11206.

Also in a preferred embodiment of the invention, the protein comprising a human-engineered antibody variable region is a Fab, F(ab')$_2$ fragment, or a single-chain antibody.

Proteins according to the present invention may be made by methods taught herein and in co-pending, co-owned U.S. patent application no. 07/808,464 by Studnicka, incorporated by reference herein. Modified antibody variable domains made by such methods may be used in therapeutic administration to humans either alone or as part of an immunoconjugate or immunofusion as taught in co-owned, co-pending U.S. Patent Application Serial No. 07/787,567 filed November 4, 1991 by Bernhard, et al. and co-owned, co-pending U.S. Patent Application Serial No. , filed May 19, 1993 by Better, et al. (Attorney Docket No. 27129/31394). Proteins according to the present invention may also be applied to determine T cell levels in order to aid in the diagnosis of human autoimmune disease states. Proteins according to the present invention are useful in the treatment of human diseases and particularly useful in the treatment of autoimmune diseases. Additionally, other T cell- mediated diseases such as graft-versus-host disease or tissue transplant rejection may be treated with proteins according to the invention.

In a therapeutic treatment or diagnostic regimen, the whole protein may be used, a fragment of the protein, such as a Fab or F(ab')$_2$ region may be used, or a single-chain antibody may be used. Alternatively, an immunoconjugate or an immunofusion comprising the protein or fragment may be used. A fragment or single chain form of the presently-claimed antibodies are especially useful in applications in which no constant region is required.

The present invention also provides methods for treatment of autoimmune diseases, wherein animal models are predictive of the efficacy of treatment in humans. Finally, the present invention includes pharmaceutical compositions containing the humanized antibodies according to the invention.

Proteins, specifically he3 antibodies, according to the present invention are all useful in diagnostic procedures, wherein it is desirable to detect, identify, or isolate CD5 antigens. Such antibodies may be labelled for diagnostic identification of CD5 antigen.

Additional aspects and applications of the present invention will become apparent to the skilled artisan upon consideration of the detailed description of the invention which follows.

BRIEF DESCRIPTION OF THE DRAWING

FIGS. 1A and 1B are alignments of the amino acid sequences of the light and heavy chains, respectively, of two murine antibody variable domains [HYH (HYHEL-10 Fab-lysozyme complex), MCPC (IgA Fab MCPC603-phosphocholine complex), and two human antibody variable domains NEWM (Ig Fab' NEW) and KOL (IgG1 KOL)] by criteria of sequence and structural homology;

FIGS. 5A and 5B are alignments of the consensus amino acid sequences for light (FIG. 5A) the subgroups of light chains [hK1 (human kappa light chain subgroup 1), hK3 (human kappa light chain subgroup 3), hK2 (human kappa light chain subgroup 2), hL1 (human lambda light chain subgroup 1), hL2 (human lambda light chain subgroup 2), hL3 (human lambda light chain subgroup 3), hL6 (human lambda light chain subgroup 6), hK4 (human kappa light chain subgroup 4), hL4 (human lambda light chain subgroup 4) and hL5 (human lambda light chain subgroup 5] and heavy chains (FIG. 5B) [hH3 (human heavy chain subgroup 3), hH1 (human heavy chain subgroup 1) and hH2 (human heavy chain subgroup 2)], respectively, of human antibody variable domains;

FIGS. 6A and 6B are alignments of human light (FIG. 6A) chain consensus sequence hK1 with the actual (h65) and low-risk modified (prop) light chain sequences of the H65 mouse monoclonal antibody variable domain and of human heavy (FIG. 6B) chain consensus sequence hH3 with the actual (h65) and modified (prop) heavy chain sequences of the H65 mouse monoclonal antibody variable domain, respectively;

FIGS. 7A and 7B are listings of the nucleotide sequences of the oligonucleotides utilized in the construction of the genes encoding modified V/J-regions of the light (FIG. 7A) and heavy (FIG. 7B) chains of the H65 mouse monoclonal antibody variable domain;

FIGS. 8A and 8B are listings of the nucleotide sequences of the genes encoding modified V/J-regions of the heavy (FIG. 8B) and light (FIG. 8A) chains, respectively, of the H65 mouse monoclonal antibody variable domain;

FIGS. 10A and 10B are alignments of human light (FIG. 10A) chain consensus hK1 and heavy (FIG. 10B) chain consensus hH1 with the light and heavy chain sequences, respectively, of the variable domain of human antibody EU, unmodified murine antibody TAC, murine antibody TAC modified according to the present invention (prop) and murine antibody TAC modified according to a different method (Que);

FIGS. 13A and 13B are schematic depictions of human T cell recovery in spleen and blood, respectively from PBMC/SCID mice following treatment with H65 monoclonal antibody (hereinafter referred to as "MoAb");

FIGS. 16A and 16B are alignments of human light chain consensus sequence hK1 with the actual (h65) and low and moderate risk modified (prop) light chain sequences of the H65 mouse monoclonal antibody variable domain and of human heavy chain consensus sequence hH3 with the actual (h65) and modified (prop) heavy chain sequences of the H65 mouse monoclonal antibody variable domain, respectively;

DETAILED DESCRIPTION OF THE INVENTION

Figure 2:
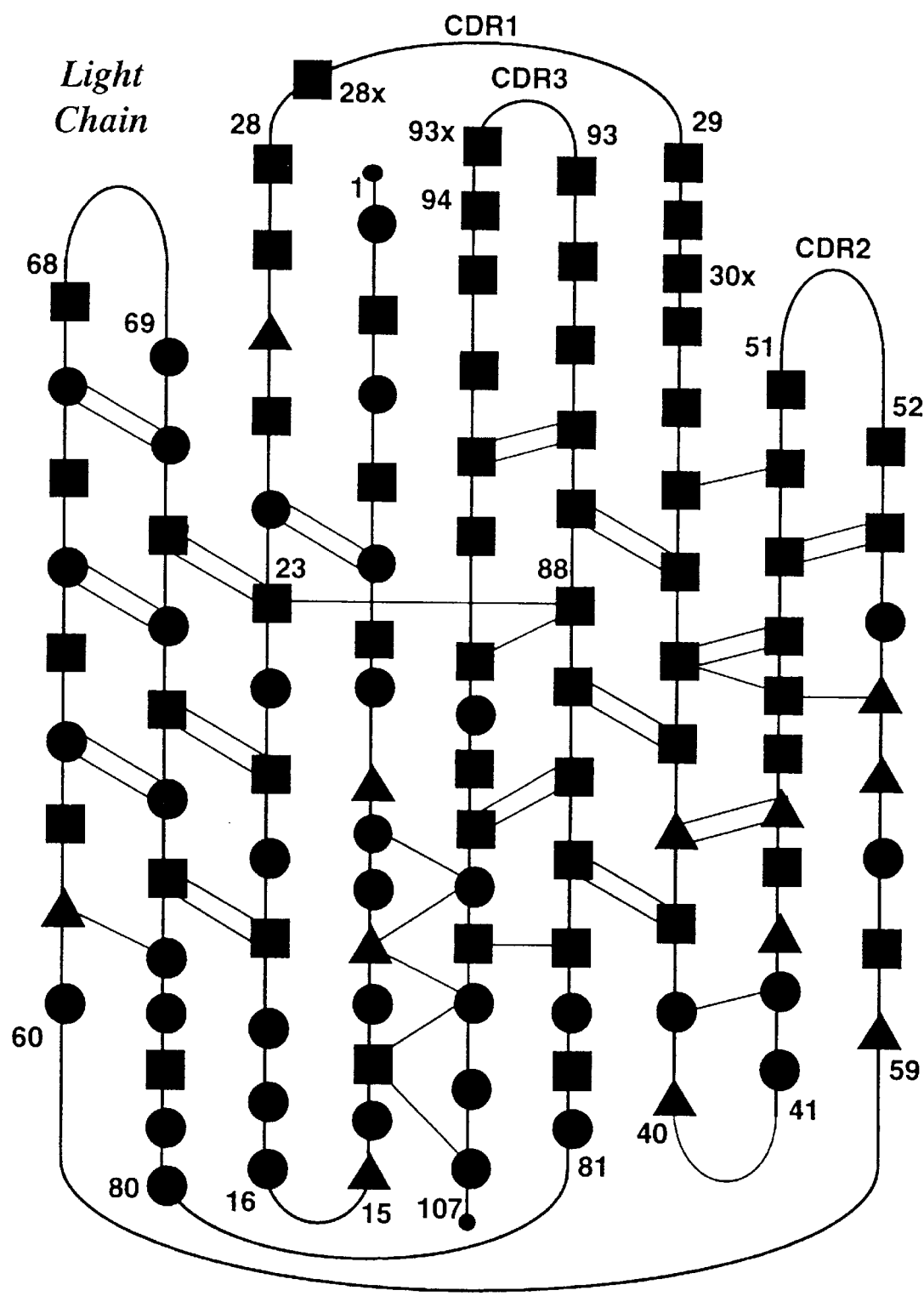
FIG. 2 is a schematic depiction of the structural relationships between the amino acid residues of the light chain of the variable domain.

Animal models of T cell-mediated autoimmune diseases were studied using therapeutic protocols with anti-T cell antibodies, especially anti-CD5 (Examples 1–3). Anti-CD5 antibodies were found to be particularly useful in several therapeutic regimens, as they were able to deplete the number of T cells in various lymphoid organs and also reduce the pathological effects of T cells. These studies provide an example of one therapeutic target (CD5) for the development of methods for the humanization of murine anti-T cell antibodies.

The present invention provides novel proteins and fragments comprising a humanized antibody variable region, and particularly an he3 variable region which is specifically reactive with a human CD5 cell differentiation marker. The invention also provides anti-CD5 antibodies with an affinity of less than about $2\times10^{-9}$M.

The terms "humanized," "human-like," or "human-engineered" refers to an immunoglobulin wherein the constant regions have at least about 80% or greater homology to human immunoglobulin, and wherein some of the nonhuman (i.e. murine) variable region amino acid residues may be modified to contain amino acid residues of human origin.

Humanized antibodies may be referred to as "reshaped" antibodies. Manipulation of the complementarity-determining regions (CDRs) is one means of manufacturing humanized antibodies. See, e.g., Jones, et al., Nature 321:522–525 (1988); Riechmann, et al., Nature 332:323–327 (1988). For a review article concerning chimeric and humanized antibodies, See Winter et al. Nature 349:293–299 (1991).

Construction of humanized antibody variable domains according to the present invention may be based on a method which includes the steps of: (1) identification of the amino acid residues of an antibody variable domain which may be modified without diminishing the native affinity of the domain for antigen while reducing its immunogenicity with respect to a heterologous species; (2) the preparation of antibody variable domains having modifications at the identified residues which are useful for administration to heterologous species; and (3) use of the humanized antibodies of the invention in the treatment of autoimmune diseases in humans. The methods of the invention are based on a model of the antibody variable domain described herein which predicts the involvement of each amino acid in the structure of the domain.

Unlike other methods for humanization of antibodies, which advocate replacement of the entire classical antibody framework regions with those from a human antibody, the methods described herein introduce human residues into the variable domain of an antibody only in positions which are not critical for antigen- binding activity and which are likely to be exposed to immunogenicity-stimulating factors. The present methods are designed to retain sufficient natural internal structure of the variable domain so that the antigen-binding capacity of the modified domain is not diminished in comparison to the natural domain.

Data obtained from the analysis of amino acid sequences of antibody variable domains using the MacImdad (Molecular Applications Group, Stanford, Calif.) three-dimensional molecular modeling program, in conjunction with data obtained from previous theoretical studies of hypervariable region structure and data obtained from the crystal structures of the HYH (HYHEL-10 Fab-lysosyme complex, Brookhaven structure "3HFM"), MCPC (IgA Fab MCPC603-phosphocholine complex, Brookhaven structure "2MCP"), NEWM (Ig Fab' NEW, Brookhaven structure "3FAB") and KOL (IgG1 KOL, Brookhaven structure "2IG2") antibody variable domains from the Brookhaven database (Brookhaven National Laboratory, Upton, N.Y.), are utilized to develop the antibody variable domain model.

FIGS. 1A and 1B provide the sequences of the four antibody variable domains which have been crystallized. The amino acid sequences of the light and heavy chains of HYH (SEQ ID NOS: 1 and 5, respectively), MCPC (SEQ ID NOS. 2 and 6, respectively), NEWM (SEQ ID NOS. 3 and 7, respectively) and KOL (SEQ ID NOS. 4 and 8, respectively) are shown, wherein the exclamation points "!" in the MCPC light chain sequence at position 30x, the MCPC heavy chain sequence at positions 52x and 98x, the NEWM light chain at position 30x, the KOL light chain at position 93x, and the KOL heavy chain sequence at position 98x, stand for the amino acid sequences NSGNQK (SEQ ID NO: 9), NKG (SEQ ID NO: 10), GST (SEQ ID NO: 11), AG, SL and HGFCSSASC (SEQ ID NO: 12), respectively which are variations in the length of hypervariable loop sequences among the various antibodies. The amino acid positions in FIGS. 1A and 1B, 2, and 3 are numbered according to Kabat et al., *Sequences of Proteins of Immunological Interest*, Fourth Edition, U.S. Department of Health and Human Services, Public Health Service, National Institutes of Health (1987) (hereinafter referred to as "Kabat"), with the exception of those designated with a lower-case "x", which are variations in length of hypervariable loops which Kabat has numbered as "a,b,c,d . . . ".

Figure 3:
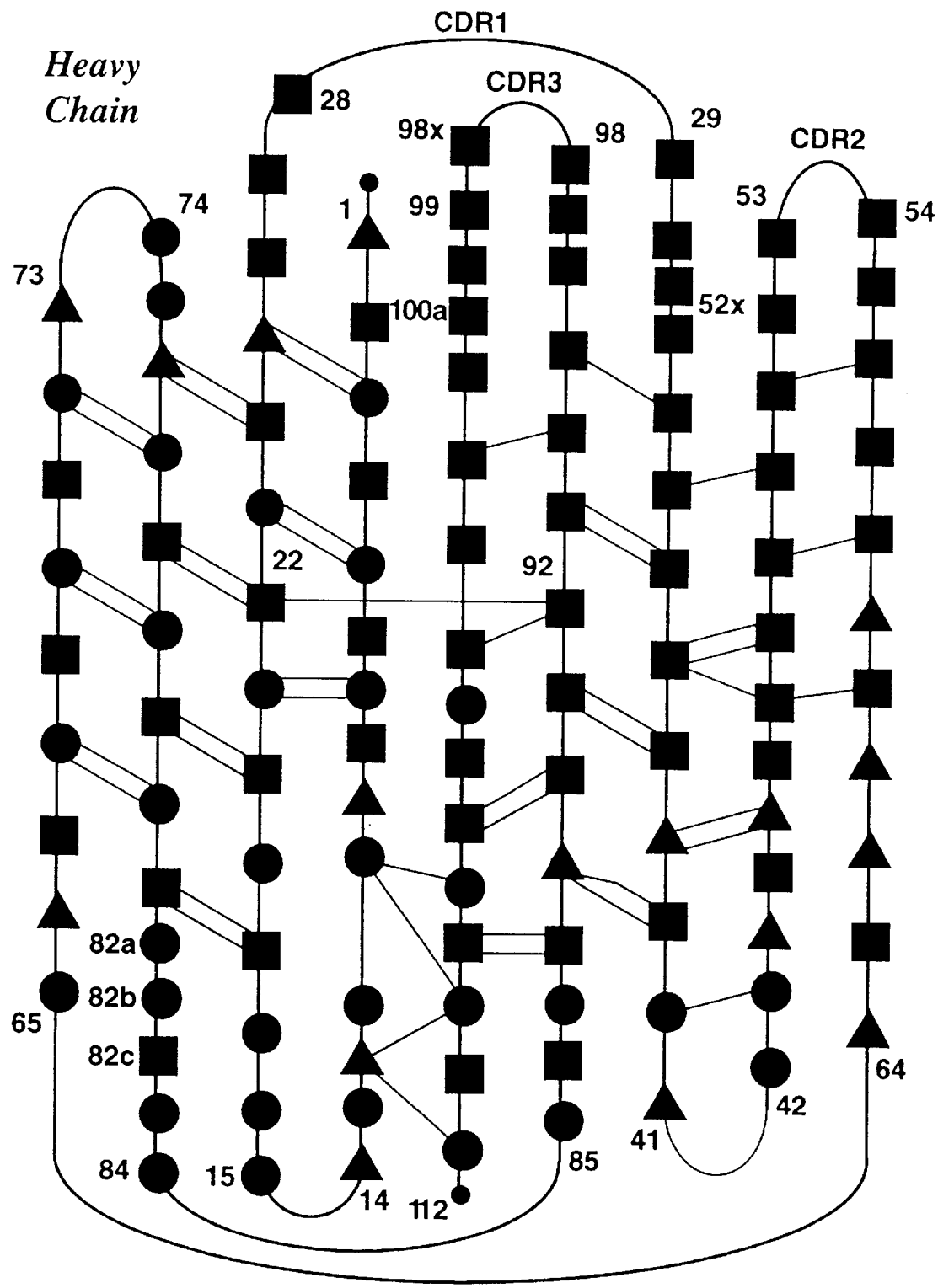
FIG. 3 is a schematic depiction of the structural relationships between the amino acid residues of the heavy chain of the variable domain.

FIGS. 2 and 3 comprise depictions of the structure of the light and heavy chains, respectively, wherein each chain is displayed "unfolded" into a flattened beta sheet structure so that interactions among the residues are easier to visualize. The strands of folded polypeptide chains are represented as thick vertical lines, connected by eight beta-turn loops. Three of the loops are identified as antigen-binding loops or CDRs, one is accessory to the loops, and the remaining four at the "bottom" of the variable domain are not involved in antigen binding. The amino and carboxy termini of the variable domain are symbolized by small black dots at the ends of the polypeptide chains. Each amino acid position is represented as either a circle, a triangle, or a square. The covalent disulfide bond between the two cysteines at positions 23 and 88 in the light chain and the covalent disulfide bond between positions 22 and 92 in the heavy chain are each shown as a thick horizontal line. All of the residues in each chain are shown on the map, including antigen-binding residues and framework residues. Solid slanted lines (either single or double) connecting pairs of residues which are adjacent in three-dimensional space but not in linear sequence, represent one or two hydrogen bonds between the mutually aligned amino nitrogens and carbonyl oxygens in the backbones of the residues.

The analysis of each amino acid position to determine whether the position influences antigen binding and/or is immunogenic was based upon the information in FIGS. 1A, 1B, 2 and 3, as well as the additional variable region structural information in the following paragraphs.

The basic structure of the antibody variable domain is strongly conserved. The variable domain is composed of a light chain (or subunit) and a heavy chain (or subunit), which are structurally homologous to each other and which are related by a pseudo-two-fold axis of rotational symmetry. At the "top" of the variable domain, the region farthest away from the constant domain, there are six antigen-binding loops which are built upon a larger structural framework region. The variable domain is functionally distinct from the constant domain, being connected only by two highly flexible chains and pivoting on both "ball-and-socket" joints formed by five amino acids in the heavy and light chains.

Each subunit, light or heavy, resembles a "sandwich" structure, composed of two layers of antiparallel beta sheets with a propeller twist in three- dimensional space. Each amino acid chain folds back on itself repeatedly to create nine distinct strands. Three-and-one-half of these strands form the "outside" beta-sheet layer of each subunit and the other five-and- one-half form the "inside" layer. The various strands in each layer are extensively hydrogen-bonded to each other. The two beta-sheet layers within the subunit are held together by a single covalent disulfide bond and by numerous internal hydrophobic interactions. The sequences involved in bonding the strands of the subunits together are called "framework" sequences.

Certain amino acids, either in antigen-binding sequences or in framework sequences, do not actually bind antigen but are critical for determining the spatial conformation of those residues which do bind. Each antigen-binding loop requires a properly formed "platform" of buried residues, which provides a surface upon which the loop folds. One or more of the loop residues often will be buried in the platform as an "anchor" which restricts the conformational entropy of the loop and which determines the precise orientation of antigen-contacting sidechains. Thus, the shapes of the residues which make up the platform contribute to the ultimate shape of the antigen-binding loop and its affinity for specific antigens.

Figure 4:
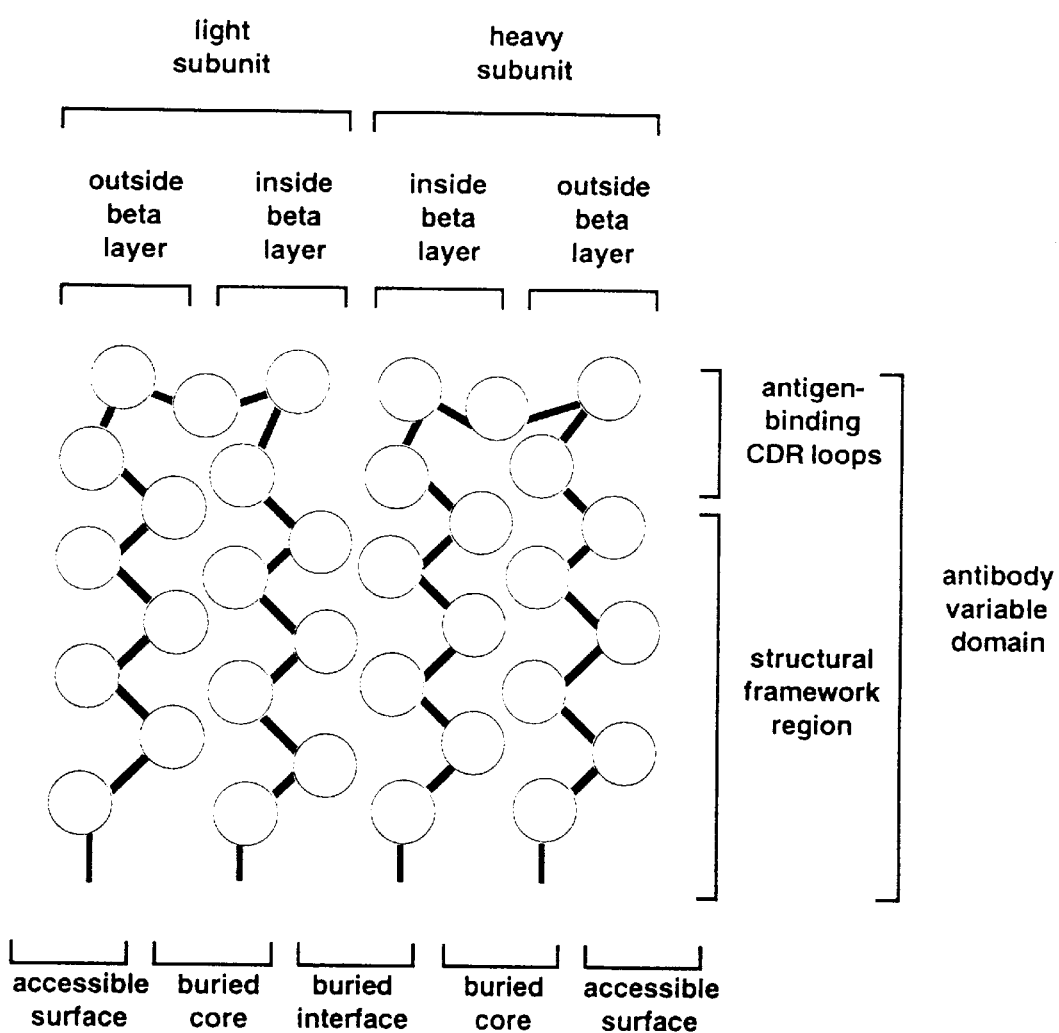
FIG. 4 is a schematic representation of an antibody variable domain.

Amino acid sidechains exist in various different chemical environments within the subunits. Some residues are exposed to the solvent on the outer accessible surface while other residues are buried in hydrophobic interactions within a subunit. Much of the immunoglobulin variable domain is constructed from antiparallel beta sheets which create amphipathic surfaces, such that the "inside" surface is hydrophobic and the "outside" surface is hydrophilic. The outside is exposed to solvent, and therefore is also exposed to the humoral environment when the domain is in the circulatory system of an animal. Amino acid sidechains which are completely exposed to the solvent and which do not physically interact with other residues in the variable domain are likely to be immunogenic and are unlikely to have any structural importance within the immunoglobulin molecule. A highly schematic representation of the variable domain is shown in FIG. 4, wherein thick lines represent peptide bonds and shaded circles denote amino acid sidechains.

The two subunits of antibody variable domains adhere to each other via a hydrophobic interface region which extends along the inside beta-sheet layer from the border of the variable domain with the constant domain to the antigen-binding loops. Amino acid sidechains from both subunits interact to form a three-layered "herringbone" structure. Some of these interfacial residues are components of the antigen-binding loops, and thus have a direct effect upon binding affinity. Every residue in the interface is structurally important because the conformation of the binding regions is strongly influenced by changes in the conformation of the interface.

The foregoing data and information on the structure of antibody variable domains aids in a determination of whether a particular amino acid of any variable domain is likely to influence antigen binding or immunogenicity. The determination for each amino acid position is represented by a pair of symbols (e.g., +and+, in the lines labelled "bind" and "bury", respectively) in FIGS. 1A, 1B, (and also in FIGS. 5A, 5B, 6A, 6B, 10A and 10B). In each of these pairs, the first symbol relates to antigen binding, while the second symbol relates to immunogenicity and framework structure. Tables 1, 2, and 3, below, set out the significance of the symbols and possible pairings.

TABLE 1

| First Symbol In Pair (Ligand Binding) | |
|---|---|
| + | Little or no direct influence on antigen-binding loops, low risk if substituted |
| o | Indirectly involved in antigen-binding loop structure, moderate risk if changed |
| – | Directly involved in antigen-binding loop conformation or antigen contact, great risk if modified |

TABLE 2

| Second Symbol In Pair (Immunogenicity And Structure) | |
|---|---|
| + | Highly accessible to the solvent, high immunogenicity, low risk if substituted |
| o | Partially buried, moderate immunogenicity, moderate risk if altered |
| – | Completely buried in subunit's hydrophobic core, low immunogenicity, high risk if changed |
| = | Completely buried in the interface between subunits, low immunogenicity, high risk if modified. |

TABLE 3

| Significance Of Pairs | |
|---|---|
| ++ Low risk | Highly accessible to the solvent and high immunogenicity, but little or no effect on specific antigen binding |
| o+, +o, oo Moderate Risk | Slight immunogenicity or indirect involvement with antigen binding |
| any - or = High risk | Buried within the subunit core/interface or strongly involved in antigen binding, but little immunogenic potential |

The pairings set out in Tables 1–3 indicate that making mouse-to-human modifications at positions which have a pair of low risk symbols (++) (i.e., a symbol in the "bind" line and a symbol in the "bury" line corresponding to one position) results in a major reduction in therapeutic immunogenicity with little chance of affecting binding affinity. At the opposite end of the spectrum, modifying positions which have a pair of high risk symbols (−−) may degrade or abolish binding activity with little or no actual reduction in therapeutic immunogenicity. There are 73 low risk positions in the variable domain (38 in the light chain and 35 in the heavy chain) which are indicated by circles in the lines labelled "risk" in FIGS. 1A, 1B, 5A, 5B, 6A, 6B, 10A and 10B. There are 29 moderate risk positions in the variable domain (12 in the light chain and 17 in the heavy chain) as indicated by the triangles in the lines labelled "risk" in FIGS., 1A, 1B, 5A, 5B, 6A, 6B, 10A, and 10B. 20 The results of the above analysis may be applied to consensus sequences for the different subgroups of antibody variable domains because the structural characteristics they represent are highly conserved, even among various species. FIGS. 5A and 5B thus set out and align the consensus sequences (derived from Kabat) of the subgroups of light (hK1, SEQ ID NO: 13; hK3, SEQ ID NO: 14; hK2, SEQ ID NO: 15; hL1 SEQ ID NO: 16; hL2, SEQ ID NO: 17; hL3, SEQ ID NO: 18; hL6, SEQ ID NO: 19; hK4, SEQ ID NO: 20; hL4, SEQ ID NO: 21; and hL5, SEQ ID NO: 22) and heavy chains (hH3, SEQ ID NO: 23;

hHl, SEQ ID NO: 24; and hH2, SEQ ID NO: 25) of antibody variable domains with the pairings representing the structural characteristics of each amino acid position, wherein the consensus sequences for the hL6, hK4, hL4, hL5 and hH2 subgroups were derived from less than twenty actual light or heavy chain sequences.

In the consensus sequences set out in FIGS. 5A and 5B, upper case amino acid designations indicate that the amino acid is present at that location in about 90% to about 100% of the known human sequences (excluding small incomplete fragments) of that subgroup (i.e., is "highly conserved"); whereas lower case amino acid designations indicate that the amino acid is present at that location in about 50% to about 90% of the known human sequences in that subgroup (i.e., is "moderately conserved"). A lower case "x" denotes conservation in less than about 50% of the known sequences in that subgroup (i.e., a "poorly conserved" position).

The information presented in FIGS. 5A and 5B on the relationship of a particular amino acid in a sequence of an antibody variable domain to the structure and antigen-binding capacity of the domain is sufficient to determine whether an amino acid is modifiable. Additional structural studies, such as those on which FIGS. 5A and 5B are based, are not required.

Thus, according to the present invention, FIGS. 5A and 5B may be used to prepare, for example, a modified mouse antibody variable domain that retains the affinity of the natural domain for antigen while exhibiting reduced immunogenicity in humans by the following steps. The amino acid sequences of both the light chain and the heavy chain from the mouse variable domain are first determined by techniques known in the art (e.g., by Edman degradation or by sequencing of a cDNA encoding the variable domain). Next, the consensus sequences set out in FIGS. 5A and 5B for human antibody variable domains are examined to identify both a light chain consensus and a heavy chain consensus sequence that are the most homologous to the particular mouse subunit sequences that are to be modified. The mouse sequences are aligned to the consensus human sequences based on homology either by sight or by using a commercially available computer program such as the PCGENE package (Intelligenetics, Mountain View, Calif.).

FIGS. 5A and 5B are then used again to identify all of the "low risk" or "moderate risk" positions at which the mouse sequence differs significantly from the chosen human consensus. The mouse amino acid residues at these low risk and moderate risk positions are candidates for modification. If the human consensus is strongly conserved at a given low risk or moderate risk position, the human residue may be substituted for the corresponding mouse residue. If the human consensus is poorly conserved at a given low risk or moderate risk position, the mouse residue is retained at that position. If the human consensus is moderately conserved at a specific position, the mouse residue is normally replaced with a human residue, unless the mouse residue occurs at that position in at least one of the sequences (e.g., in Kabat) on which the human consensus sequence is based. If the mouse residue does occur at that position in a human sequence then the mouse residue may be retained.

Other criteria may be important to the determination of which identified residues of a variable region are to be modified. For example, since the side chain of proline is connected to both its α-carbon and its peptide nitrogen, free rotation is restricted around the carbon-nitrogen bond (the Ramachandran ø angle).

Therefore, wherever there is a proline in a sequence, the shape of the backbone is distorted and that distortion can influence other residues involved in antigen binding. The presence or absence of a proline residue at any point in the amino acid sequence is a structurally important feature. If the mouse sequence contains a proline at a certain location, it is likely that its presence is necessary for a proper backbone and framework conformation and proline is preferably retained. If the mouse sequence does not contain a proline at a location where the human consensus sequence has one, it is likely that substituting a proline in the mouse sequence would affect proper conformation of the sequence, therefore the mouse residue is preferably retained. Where a proline at a particular position involving proline is changed from mouse to human, such a change is considered to be at least moderate risk even if that position would otherwise be low risk.

Similarly, insertions and deletions in a mouse sequence, relative to a human consensus framework, are normally preserved intact. If the mouse sequence has an alteration in the length and spacing of the variable region backbone, it is likely that the alteration is necessary to provide a surface for proper folding of the antigen-binding loops. The alteration is preferably retained in a modified version of the sequence.

Residues participating in the interface between the light and heavy chains of a variable domain are also preferably left intact in a modified version. They are all designated high risk, with=symbols on the "bury" lines in FIGS. 1, 5, 6, 10. The sidechains in the interface region are buried deep within the structure, so they are unlikely to elicit a therapeutic immunogenic response in a heterologous species.

Once a modified sequence has been designed, DNAs encoding the complete variable domain may be synthesized [via oligonucleotide synthesis as described, for example, in Sinha et al., *Nucleic Acids Res.,* 21:4539–4557 (1984)], assembled [via PCR as described, for example in Innis, Ed., *PCR Protocols,* Academic Press (1990) and also in Better et al. *J. Biol. Chem.* 267:16712–16118 (1992)], cloned and expressed [via standard procedures as described, for example, in Ausubel et al., Eds., *Current Protocols in Molecular Biology,* John Wiley & Sons, New York (1989) and also in Robinson et al., *Hum. Antibod. Hybridomas,* 2:84–93 (1991)], and finally tested for specific antigen binding activity [via competition assay as described, for example, in Harlow et al., Eds., *Antibodies: A Laboratory Manual,* Chapter 14, Cold Spring Harbor Laboratory, Cold Spring Harbor (1988) and Munson et al., *Anal. Biochem.,* 107:220–239 (1980)].

Humanized antibodies according to the present invention may be incorporated into an immunoconjugate for use in the treatment of various human diseases. For example, treatment of certain autoimmune diseases with immunotoxin conjugates is described in co-pending, co-owned U.S. patent application Ser. No. 07/759,297 filed Sep. 13, 1991, and U.S. patent application Ser. No. 07/988,430, filed Dec. 9, 1992, both of which are incorporated by reference herein. An immunoglobulin such as an anti-T-cell immunoglobulin may be conjugated to a cytotoxic molecule. The cytotoxic molecule to which the immunoglobulin is conjugated may be any of a number of toxins such as lectin A or a ricin A chain. The above-referenced '297 application also describes use of an anti-CD5 antibody conjugated to a ricin A chain providing an anti-T-cell immunotoxin. Humanized antibodies of the invention may also be used in immunofusions with, for example, gelonin toxin as taught in co-owned, co-pending U.S. patent application Ser. No. 08/064,691, filed May 12, 1993.

Humanized antibodies according to the present invention include he3 and fragments thereof which display increased content of human amino acids and a high affinity for human CD5 cell differentiation marker. The he3 antibody is a humanized form of the mouse H65 antibody in which the moderate risk changes described below were made in both variable regions. Such humanized antibodies have less immunogenicity and have therapeutic utility in the treatment of autoimmune diseases in humans. For example, because of their increased affinity over existing therapeutic monoclonal antibodies such as H65, he3 antibodies of the invention may be administered in lower doses than H65 anti-CD5 antibodies in order to obtain the same therapeutic effect. The he3 variable regions are also useful in increasing potency over H65 anti-CD5 antibodies when used as a portion of an immunoconjugate or immunofusion protein.

The he3 proteins according to the present invention may also be used in the treatment of graft-versus-host disease. Laurent et al. *Bone Marrow Transplantation,* 4:367–371 (1989), incorporated by reference herein, reports that administration of a murine anti-CD5 Fab-RTA conjugate may greatly reduce the likelihood of graft-versus-host disease by causing an ex 25 vivo purge of T cells from donor bone marrow prior to transplantation. See also, Antin et al., *Blood,* 78:2139–2149 (1991); Kernan et al., *J. Am. Med. Assoc.,* 259:3154–3157 (1988), both incorporated by reference herein.

Alternatively, anti-CD5 antibodies and 30 particularly human-engineered anti-CD5 antibodies of the present invention may be utilized in an unconjugated form for the therapy of autoimmune diseases. Such antibodies and uses are detailed below.

A general description of various autoimmune diseases is found in *The Autoimmune Diseases* (Rose & Mackey, eds 1985). Autoimmune diseases may be characterized, inter alia, by abnormal immunological regulation which results in excessive B cell activity and diminished, enhanced, or inappropriate T cell activity. Such altered T cell activity may result in excessive production of autoantibodies. Although the autoimmune diseases are complex and diverse in their manifestations, they possess the common feature of a malfunctioning immune system. Therapeutic depletion of circulating T cells through the administration of an anti-pan T cell immunoglobulin improves the clinical course of patients with autoimmune disease. For anti-CD5 antibody therapy, the additional depletion of CD5 B cells may have a further beneficial effect since CD5 B cells have been implicated in some autoimmune diseases.

An example of an anti-pan T cell immunoglobulin is a CD5 antibody which is primarily reactive with a surface antigen of mature T cells, but is also reactive with 10–20% of mature B cells. Clinical data obtained using an anti-pan T cell immunoglobulin in models of autoimmune diseases in non-human animals are predictive of the effects of using such immunoglobulins as therapy against human autoimmune diseases. Once prepared, humanized antibodies are then useful in the treatment of autoimmune disease. In this regard, an anti-CD5 monoclonal antibody is presented as an example of a preferred embodiment of the invention.

For the purpose of the present invention, an immunoglobulin, such as an antibody, is "reactive" with or "binds to" an antigen if it interacts with the antigen, forming an antigen-immunoglobulin complex. The antigen is generally a unique surface protein or marker. A most preferred marker is the CD5 antigen cluster.

An anti-pan T cell immunoglobulin may be obtained from a number of sources. It is reactive with most mature T cells or with both T cells and subsets of other lymphoid cells, such as B cells or natural killer (NK) cells. The immunoglobulin may be synthetic or recombinant, including genetically-engineered immunoglobulins such as chimeric immunoglobulins, humanized antibodies, hybrid antibodies, or derivatives of any of these.

Chimeric immunoglobulins, antibodies or peptides comprise fused portions from different species produced by chimeric DNA. Chimeric DNA is recombinant DNA containing genetic material from more than one mammalian species. Chimeric immunoglobulins include one portion having an amino acid sequence derived from, or homologous to, a corresponding sequence in an immunoglobulin, antibody or peptide derived from a first gene source while the remaining segment of the chain(s) is homologous to corresponding sequences from another gene source. For example, a chimeric antibody peptide may comprise an antibody heavy chain with a murine variable region and a human constant region. The two gene sources will typically involve two species, but will occasionally involve different sources from one species.

Chimeric immunoglobulins, antibodies, or peptides are typically produced using recombinant molecular and/or cellular techniques. Specifically, chimeric antibodies have variable domains of both light and heavy chains which mimic the variable domains of antibodies derived from one mammalian species, while the constant portions are homologous to the sequences in antibodies derived from a second, different mammalian species.

Immunoglobulins of the present invention may be monoclonal antibodies (hereinafter referred to as "MoAbs") of the IgM or IgG isotype of murine, human or other mammalian origin. Most preferably, such a MoAb is reactive with the CD5 antigen found on both T and B cells. MoAbs from other animal species may be prepared using analogous non-human mammalian markers.

In addition to the human-engineering methods of the current invention, a variety of methods for producing MoAbs are known in the art. See, e.g., Goding, *Monoclonal Antibodies; Principles and practice* (2d ed., Academic Press 1986), which is incorporated by reference herein. Less preferred forms of immunoglobulins may be produced by methods well-known to those skilled in the art, such as by chromatographic purification of polyclonal sera to produce substantially monospecific antibody populations.

Monoclonal antibodies specifically directed against human CD5 antigen may be obtained by using combinations of immunogens and screening antigens which have only the human CD5 antigen in common or by a screening assay designed to be specific for only anti-CD5 monoclonals. For example, production of monoclonal antibodies directed against CD5 may be accomplished by 1) immunization with human T cells expressing the CD5 antigen followed by screening of the resultant hybridomas for reactivity against a non-human cell line transfected with human CD5 (constructed in a manner similar to that described in Nishimura, et al., *Eur. J. Immunol.*, 18:747–753 (1988)); 2) immunization with a non-human cell line transfected with human CD5 followed by screening of the resultant hybridomas for reactivity against a human T cell line expressing the CD5 antigen; 3) immunization with human or non-human cell lines expressing human CD5 followed by screening of the resultant hybridomas for ability to block reactivity of existing anti-CD5 monoclonals with a human T cell line; 4) immunization with human or non-human cell lines expressing human CD5 followed by screening of the resultant hybridomas for reactivity with purified native or recombinant CD5 antigen; or 5) immunization with a recombinant derivative of the human CD5 antigen followed by screening of the resultant hybridomas for reactivity against a human T cell line expressing CD5.

A preferred monoclonal antibody for use in preparing humanized antibodies according to the present invention is produced by hybridoma cell line XMMLY-H65 (H65) deposited with the American Type Culture Collection, 12301 Parklawn Drive, Rockville, Md. 20852 on and given the Accession No. HB 9286. A preferred antibody is prepared as disclosed herein using the human-engineered forms of the murine H65 antibody.

The generation of human MoAbs to a human antigen is also known in the art. See, e.g., Koda et al. *Hum. Antibod. Hybridomas*, 1(1):15–22 (1990). Generation of such MoAbs may be difficult with conventional techniques. Thus, it may be desirable to modify the antigen binding regions of the non-human antibodies, e.g., the $F(ab')_2$ or hypervariable regions (CDRs), and fuse them to human constant regions (Fc) or framework regions by recombinant DNA techniques to produce substantially human molecules using general modification methods described in, for example, EP publications 173,494 and 239,400, which are incorporated by reference herein.

Alternatively, one may isolate DNA sequences which encode a human MoAb or portions thereof which specifically bind to the human T cell by screening a DNA library from human B cells according to the general protocols outlined by Huse et al., *Science* 246:1275–1281 (1989); Marks, et al., *J. Mol. Biol.* 222:581–597 (1991) which are incorporated by reference herein, and then cloning and amplifying the sequences which encode the antibody (or binding fragment) of the desired specificity.

In addition to the immunoglobulins specifically described herein, other "substantially homologous" modified immunoglobulins may be readily designed and manufactured utilizing various recombinant DNA techniques known to those skilled in the art. Modifications of the immunoglobulin genes may be readily accomplished by a variety of well-known techniques, such as site-directed mutagenesis. See, Gillman et al., *Gene* 8:81–97 (1979); Roberts, et al., *Nature* 328:731–734 (1987), both of which are incorporated by reference herein. Also, modifications which affect the binding affinity of the antibody may be selected using the general protocol outlined by Marks, et al., *J. Biol. Chem.*, 267:16007–16010 (1992), which is incorporated by reference herein.

In the present invention, an immunoglobulin, antibody, or peptide is specific for a T cell if it binds or is capable of binding T cells as determined by standard antibody-antigen or ligand-receptor assays. Examples of such assays include competitive assays, immunocytochemistry assays, saturation assays, or standard immunoassays such as ELISA, RIA, and flow cytometric assays. This definition of specificity also applies to single heavy and/or light chains, CDRs, fusion proteins, or fragments of heavy and/or light chains, which bind T cells alone or are capable of binding T cells if properly incorporated into immunoglobulin conformation with complementary variable regions and constant regions as appropriate.

In some competition assays, the ability of an immunoglobulin, antibody, or peptide fragment to bind an antigen is determined by detecting the ability of the immunoglobulin, antibody, or peptide to compete with a compound known to bind the antigen. Numerous types of competitive assays are known and are discussed herein. Alternatively, assays which measure binding of a test compound in the absence of an inhibitor may also be used. For instance, the ability of a molecule or other compound to bind T cells may be detected by labelling the molecule of interest directly, or it may be unlabelled and detected indirectly using various sandwich assay formats. Numerous types of binding assays such as competitive binding assays are known. See, e.g., U.S. Pat. Nos. 3,376,110, 4,016,043; Harlow et al., *Antibodies: A Laboratory Manual*, (Cold Spring Harbor Publications, N.Y. 1988), which are incorporated by reference herein.

Assays for measuring binding of a test compound to one component alone rather than using a competition assay are also available. For instance, immunoglobulins may be used to identify the presence of a T cell marker. Standard procedures for monoclonal antibody assays, such as ELISA, may be used. See, Harlow and Lane, supra. For a review of various signal producing systems which may be used, see U.S. Pat. No. 4,391,904, which is incorporated by reference herein.

Other assay formats may involve the detection of the presence or absence of various physiological or chemical changes which result from an antigen-antibody interaction. See *Receptor-Effector Coupling—A Practical Approach* (Hulme, ed., IRL Press, Oxford 1990), which is incorporated by reference herein.

Humanized antibodies of the present invention may be administered to patients with a disease having targetable cellular markers. Such diseases include, but are not limited to, autoimmune diseases such as lupus (including systemic lupus erythematosus and lupus nephritis), scleroderma diseases (including lichen sclerosis, morphea and lichen planus), rheumatoid arthritis and the spondylarthropathies, thyroiditis, pemphigus vulgaris, diabetes mellitus type 1, progressive systemic sclerosis, aplastic anemia, myasthenia gravis, myositis including polymyositis and dermatomyositis, Sjogren's disease, collagen vascular disease, polyarteritis, inflammatory bowel disease (including Crohn's disease and ulcerative colitis), multiple sclerosis, psoriasis and primary biliary cirrhosis; other diseases mediated by T cells, such as tissue transplant rejection and graft versus host disease; diseases caused by viral infections; diseases caused by fungal infections; diseases caused by parasites; and the like.

Immunoglobulins, antibodies or peptides according to the invention may be administered to a patient either singly or in a cocktail containing two or more antibodies, other therapeutic agents, compositions, or the like, including, but not limited to, immunosuppressive agents, potentiators and side-effect relieving agents. Of particular interest are immunosuppressive agents useful in suppressing allergic or other undesired reactions of a host. Immunosuppressive agents include prednisone, prednisolone, dexamethasone, cyclophosphamide, cyclosporine, 6-mercaptopurine, methotrexate, azathioprine, and gamma globulin. All of these agents are administered in generally accepted efficacious dose ranges such as those disclosed in the *Physician's Desk Reference*, 41st Ed. (1987). In addition to immunosuppressive agents, other compounds such as an angiogenesis inhibitor may be administered with the anti-pan T immunoglobin. See Peacock, et al., *Arthritis and Rheum.* 35 (Suppl.), Abstract, No. B141 (September 1992).

Anti-pan T cell immunoglobulins may be formulated into various preparations such as injectable and topical forms. Parenteral formulations are preferred for use in the invention, most preferred is intramuscular (i.m.) or intravenous (i.v.) administration. The formulations containing therapeutically effective amounts of anti-pan T cell antibodies are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of from about .01 mg/kg of host body weight to about 10 mg/kg or more of host body weight.

Typically, the pharmaceutical compositions containing anti-pan T cell immunoglobulins are administered in a therapeutically effective dose in a range of from about 0.01 mg/kg to about 5 mg/kg body weight of the treated animal. A preferred dose range of the anti-pan T cell antibody is from about 0.02 mg/kg to about 2 mg/kg body weight of the treated animal. The immunoglobulin dose is administered over either a single day or several days by daily intravenous infusion. For example, for a patient weighing 70 kg, about 0.7 mg to about 700 mg per day is a preferred dose. A more preferred dose is from about 1.4 mg to about 140 mg per day.

Anti-pan T cell immunoglobulin may be administered systemically by injection intramuscularly, subcutaneously, intrathecally, intraperitoneally, into vascular spaces, or into joints (e.g., intraarticular injection at a dosage of greater than about 1 $\mu$g/cc joint fluid/day). The dose will be dependent upon the properties of the anti-pan T cell immunoglobulin employed, e.g., its activity and biological half-life, the concentration of anti-pan T cell antibody in the formulation, the site and rate of dosage, the clinical tolerance of the patient involved, the autoimmune disease afflicting the patient and the like as is well within the knowledge of the skilled artisan.

The anti-pan T cell immunoglobulin of the present invention may be administered in solution. The pH of the solution should be in the range of about pH 5.0 to about 9.5, preferably pH 6.5 to 7.5. The anti-pan T cell immunoglobulin or derivatives thereof should be in a solution having a pharmaceutically acceptable buffer, such as phosphate, tris (hydroxymethyl) aminomethane-HCl, or citrate and the like. Buffer concentrations should be in the range from about 1 to about 100 mM. A solution containing anti-pan T cell immunoglobulin may also contain a salt, such as sodium chloride or potassium chloride in a concentration from about 50 mM to about 150 mM. An effective amount of a stabilizing agent such as albumin, a globulin, a detergent, a gelatin, a protamine, or a salt of protamine may also be included and may be added to a solution containing anti-pan T cell immunoglobulin or to the composition from which the solution is prepared. Systemic administration of anti-pan T cell immunoglobulin is typically made every two to three days or once a week if a chimeric or humanized form is used. Alternatively, daily administration is useful. Usually administration is by either intramuscular injection or intravascular infusion.

Alternatively, anti-pan T cell immunoglobulin is formulated into topical preparations for local therapy by including a therapeutically effective concentration of anti-pan T cell immunoglobulin in a dermatological vehicle. Topical preparations may be useful to treat skin lesions such as psoriasis and dermatitis associated with lupus. The amount of anti-pan T cell immunoglobulin to be administered, and the anti-pan T cell immunoglobulin concentration in the topical formulations, will depend upon the vehicle selected, the clinical condition of the patient, the systemic toxicity and the stability of the anti-pan T cell immunoglobulin in the formulation. Thus, the physician will necessarily employ the appropriate preparation containing the appropriate concentration of anti-pan T cell immunoglobulin in the formulation, as well as the amount of formulation administered depending upon clinical experience with the patient in question or with similar patients.

The concentration of anti-pan T cell immunoglobulin for topical formulations is in the range from about 0.1 mg/ml to about 25 mg/ml. Typically, the concentration of anti-pan T cell immunoglobulin for topical formulations is in the range from about 1 mg/ml to about 20 mg/ml. Solid dispersions of anti-pan T cell immunoglobulin as well as solubilized preparations may be used. Thus, the precise concentration to be used in the vehicle may be subject to modest experimental manipulation in order to optimize the therapeutic response. Greater than about 10 mg of anti-pan T cell immunoglobulin/100 grams of vehicle may be useful with 1% w/w hydrogel vehicles in the treatment of skin inflammation. Suitable vehicles, in addition to gels, are oil-in-water or water-in-oil emulsions using mineral oils, petrolatum, and the like.

Anti-pan T cell immunoglobulin may be optionally administered topically by the use of a transdermal therapeutic system (Barry, *Dermatological Formulations*, p. 181 (1983)). While such topical delivery systems have been designed largely for transdermal administration of low molecular weight drugs, by definition they are capable of percutaneous delivery. They may be readily adapted to administration of anti-pan T cell immunoglobulin or derivatives thereof and associated therapeutic proteins by appropriate selection of the rate-controlling microporous membrane.

Preparations of anti-pan T cell immunoglobulin either for systemic or local delivery may be employed and may contain excipients as described above for parenteral administration and other excipients used in a topical preparation such as cosolvents, surfactants, oils, humectants, emollients, preservatives, stabilizers and antioxidants. Any pharmacologically acceptable buffer may be used, e.g., Tris or phosphate buffers.

Administration may also be intranasal or by other non-parenteral routes. Anti-pan T cell immunoglobulin may also be administered via microspheres, liposomes or other microparticulate delivery systems placed in certain tissues including blood.

Anti-pan T cell immunoglobulin may also be administered by aerosol to achieve localized delivery to the lungs. This is accomplished by preparing an aqueous aerosol or liposomal preparation. A nonaqueous (e.g., fluorocarbon propellent) suspension may be used. Sonic nebulizers preferably are used in preparing aerosols. Sonic nebulizers minimize exposing the anti-pan T cell antibody or derivatives thereof to shear, which can result in degradation of anti-pan T cell immunoglobulin.

Ordinarily, an aqueous aerosol is made by formulating an aqueous solution or suspension of anti-pan T cell immunoglobulin together with conventional pharmaceutically acceptable carriers and stabilizers. The carriers and stabilizers will vary depending upon the requirements for the particular anti-pan T cell immunoglobulin, but typically include nonionic surfactants (Tweens, Pluronics, or polyethylene glycol), innocuous proteins such as serum albumin, sorbitan esters, oleic acid, lecithin, amino acids such as glycine, buffers, salts, sugars, or sugar alcohols. The formulations are sterile. Aerosols generally may be prepared from isotonic solutions.

Alternatively, administration may be by an oral route, such as the method described by Steiner, et al. (U.S. Pat. No. 4,925,673), where the protein is delivered after encapsulation with a proteinoid substance.

Each of the foregoing materials and methods are illustrated by way of the following examples, which are 20 not to be construed as limiting the invention. All references cited herein are incorporated by reference.

EXAMPLES

Example 1

A. The Use Of Anti-CD5 (Anti Lyt 1) In The Prophylactic Treatment Of Collagen Induced Arthritis In DBA/IJ Mice Collagen-induced arthritis ("CIA") is a widely utilized model of human rheumatoid arthritis. CIA is characterized by a chronic polyarticular arthritis which can be induced in rodents and in primates by immunization with homologous or heterologous, native Type II collagen. The resulting arthritis resembles rheumatoid arthritis because there are similar histopathologic sequelae, cellular and humoral immune responses and restricted association with specific major histocompatibility complex ("MHC") haplotypes.

Native, heterologous Type II collagen emulsified with complete Freund's adjuvant induces an arthritis-like autoimmune reaction in DBA/IJ mice after a single intradermal tail injection. The mice were obtained from Jackson Laboratories, Bar Harbor, Me. Initially, the arthritis is noticeable as a slight swelling of one or more digits in the fourth week post-immunization. The chronic phase of CIA continually worsens over the ensuing 8 weeks as the arthritis progresses from the digits into the remaining peripheral articulating joints and eventually ends with ankylosis of the involved joints. The histopathology of CIA is characterized by lymphocyte infiltration of the joint space, synovial MHC class II expression and pannus formation. Not all joints are involved on every mouse, so there is a spectrum of arthritic severity. In a group of ten or more mice, the overall arthritic severity develops in a linear fashion over the course of 10–12 weeks.

The CIA model was used to test the potential efficacy of a monoclonal antibody directed against the pan-T cell surface antigen, Lyt-1, the murine equivalent of CD5. The antibody was administered to the mice before the immunization with Type II collagen. Normal DBA/I mice were also treated with a single 0.4 mg/kg i.v. injection of anti-Lyt-1 and were sacrificed after 72 hours for FACS analysis and for in vitro proliferation assays on spleen and lymph node cells. Any efficacy of this antibody would indicate a beneficial T cell-directed approach in rheumatoid arthritis via the CD5 surface antigen.

B. Effects of Anti-CD5 (Anti-Lyt-1) on DBA/IJ Spleen Cells and Peripheral Lymph Nodes Antibody 53-7.313 is a rat $IgG_{2a}$ monoclonal antibody (ATCC Accession No. TIB 104) reactive with all alleles of the mouse lymphocyte differentiation antigen, Lyt-1. The IND1 antibody is a mouse $IgG_1$, anti-human melanoma antibody used as a negative control (XOMA Corp., Berkeley, Calif.) . All other antibodies were obtained from Pharmingen Inc. (San Diego, Calif.) as direct conjugates for quantitation on a Becton-Dickinson FACScan instrument.

Male DBA/IJ mice, age 6–8 weeks, were administered a single intravenous dose of either phosphate buffered saline, IND1 or anti-CD5 (anti-Lyt-1) via the tail vein at 0.4 mg/kg in 0.1 ml of phosphate buffered saline. Mice were sacrificed for analysis three days after dosing. Single cell suspensions of spleens and peripheral lymph nodes were prepared by standard procedures and $1 \times 10^6$ cells were stained with the respective antibodies for fluorescence activated cell sorter (FACS) analysis. Proliferation assays were also performed to provide a second measure of T cell depletion. Cells ($1 \times 10^5$/well) were stimulated with Concanavalin A, Interleukin-2 ("IL-2"), IL-2 and H57.597 (a pan $\alpha,\beta$ T cell receptor antibody) or the Staphylococcal enterotoxins A and B. Cells were cultured for a total of 72 hours and proliferation was quantitated by the addition of $^3H$-methylthymidine for the last 24 hours. After 72 hours, the cells were harvested with an Inotech INB-384 harvesting and counting system, which collects the cells onto glass fiber filters with subsequent gas proportional beta particle detection. Results are generally expressed as the mean of triplicate wells±SEM in Tables 4 and 5.

C. FACS Analysis Of Lymph Node And Spleen Cells

FACS analysis of lymph node cells ("LNC") and spleen cells ("SPC") from each treatment group (n=3/group) were analyzed for percent expression of $\alpha,\beta$ T cell receptor, CD3, CD4, CD5, and CD8. The results are presented in Table 4.

TABLE 4

FACS Analysis Of Anti-CD5 (Anti-Lyt-1) Treated DBA/1J Mice

| TREAT- MENT | CELL TYPE | $\alpha, \beta TCR$ | CD3 | CD4 | CD8 | CD5 |
|---|---|---|---|---|---|---|
| PBS | LNC | 80.2 ± 2.2% | 79.8 ± 1.6% | 58.7 ± 1.4% | 19.4 ± 2.6% | 80.0 ± 0.6% |
| IND1 | LNC | 82.5 ± 1.3% | 82.6 ± 1.9% | 60.9 ± 2.0% | 21.1 ± 1.5% | 78.5 ± 1.2% |
| αCD5 | LNC | *62.7 ± 5.8% | *62.4 ± 1.0% | *42.0 ± 1.9% | 21.1 ± 0.2% | *56.0 ± 2.6% |
| PBS | SPC | 18.0 ± 2.8% | 25.0 ± 0.1% | 16.5 ± 2.1% | 4.10 ± 0.5% | 23.1 ± 0.1% |
| INDI | SPC | 19.3 ± 1.6% | 22.8 ± 1.4% | 13.9 ± 0.8% | 4.20 ± 0.3% | 20.8 ± 1.5% |
| αCD5 | SPC | 14.0 ± 0.3% | *13.8 ± 0.4% | *8.07 ± 0.3% | *2.40 ± 0.1% | *11.0 ± 0.1% |

In Table 4, statistical significance was determined by Analysis of Variance followed by Duncan's New Multiple Range post-hoc test. These data indicate that administration of anti-CD5 (anti-Lyt-1) antibody results in a significant depletion of peripheral T lymphocytes at the 72 hour time point. The results could not be explained by residual circulating antibody as other T cell markers (CD3, etc.) are also depleted to a similar extent.

D. Effects Of Anti-CD5 (Anti Lyt-1) Administration On Proliferation Analysis In vitro proliferation assays were performed on mice from each treatment group (n=3/group) in response to Concanavalin A, IL-2, IL-2+H57, Staphylococcal enterotoxin A and B ("SEA" and "SEB"). The results are presented in Table 5.

Overall, these data indicate that there is an observable and functional depletion of DBA/IJ T peripheral lymphocytes 72 hours after a single (0.4 mg/kg) intravenous dose of anti-CD5 (anti-Lyt-1) antibody.

E. Effects Of Anti-CD-5 (Anti Lyt-1) On Collagen-Induced Arthritis in DBA/IJ Mice Male DBA/IJ mice, age 6–8 weeks, were administered the antibodies 53-7.313 anti-CD5 (anti-Lyt-1), IND1 (anti-melanoma) or phosphate buffered saline (PBS) in two intravenous (0.4 mg/kg) doses 48 hours apart starting four days prior to immunization with 100 µg of bovine type II collagen emulsified with an equal volume of Freund's complete adjuvant to a final injection volume of 100 µl. Each dose group was comprised of ten mice. Mice were monitored weekly starting on Day 21

TABLE 5

Proliferation Analysis Of Anti-CD5 (Anti-Lyt-1) Treated DBA/1J Mice

| TREAT-MENT | Concanavalin A | IL-2 | IL-2 + H57 | SEA | SEB |
|---|---|---|---|---|---|
| IND1 | 26547 ± 3501 | 1181 ± 234 | 11341 ± 1663 | 12324 ± 1968 | 8747 ± 2025 |
| αCD5 | *11561 ± 4375 | *593 ± 274 | *4090 ± 2383 | *5568 ± 2576 | *1138 ± 350 | after immunization. Individual mice were scored for arthritic severity by grading each paw on a scale from 0 to 2. A score of 1 indicated swelling in up to two digits and a score of 2 indicated swelling in more than two digits up to total paw involvement and ankylosis of the large joint in the later time points. An individual mouse could have a maximum arthritic severity score of 8. Mice were monitored until day 80 after collagen immunization and then were sacrificed by cervical dislocation. Results are expressed as the mean arthritic score for each dose group.

Statistical significance was determined by a Repeated Measures Analysis of Variance with one between subjects variable (antibody treatment). A Repeated Measures Analysis was necessary as each mouse was continually monitored for the duration of the study. Thus, the arthritic scores for consecutive days cannot be considered as independent observations contributing to the overall degrees of freedom in the F test for significant differences among groups. A Repeated Measures Analysis uses the degrees of freedom from the number of individuals per group instead of the number of observations. A typical between subjects Analysis of Variance may be inappropriate and may indicate false significance among the treatment groups. A comparison of means in the Treatment by Day after Immunization was done to determine the significance of anti-CD5 (anti-Lyt-1) treatment relative to PBS and IND1 control groups.

Figure 12:
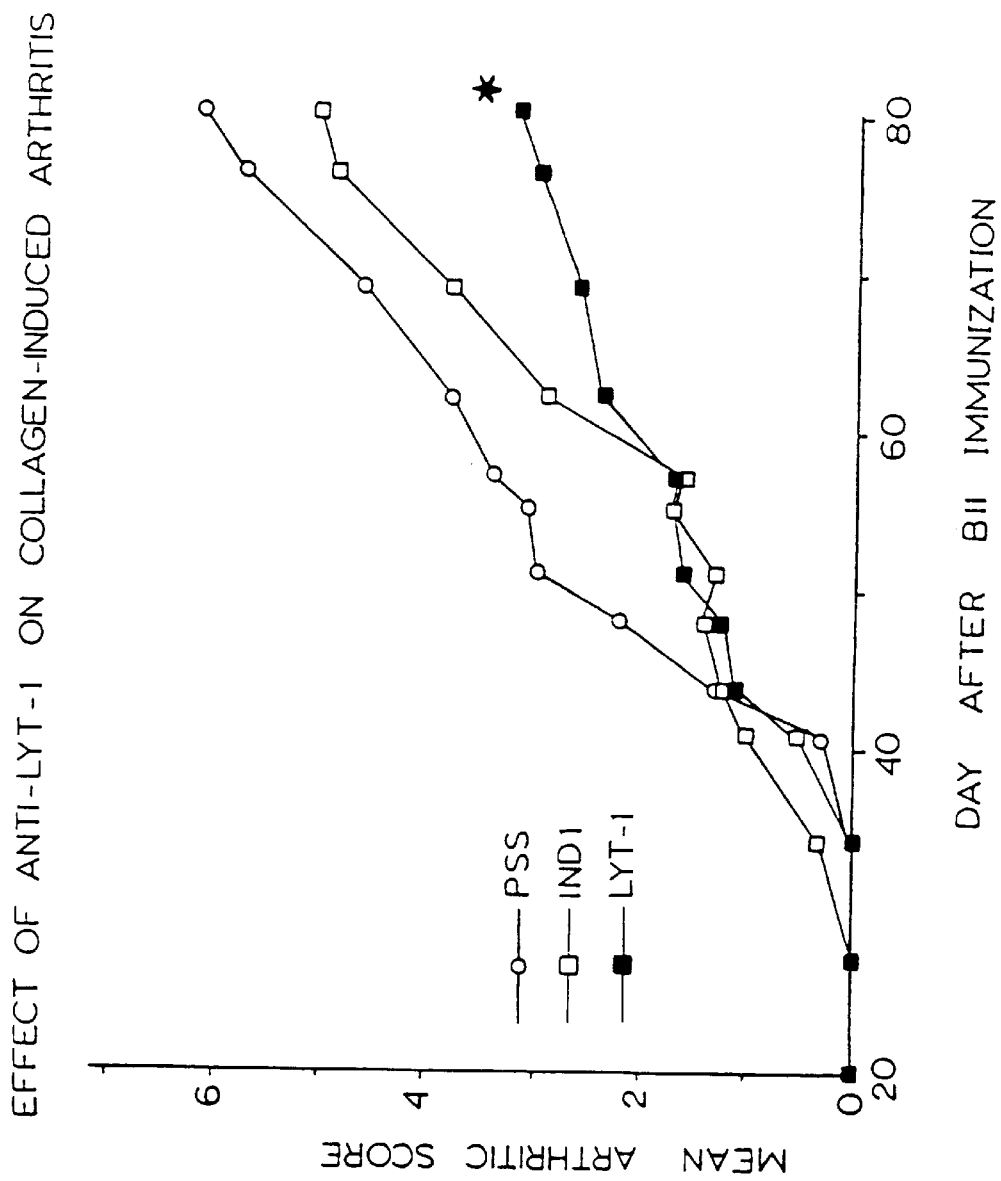
FIG. 12 is a graph showing the effects of anti-Lyt-1 (murine anti-CD5) administration on the severity of collagen-induced arthritis in DBA/1J mice.

The changes in arthritic score during the course of the study are shown in FIG. 12, where circles indicate PSS, open boxes represent Ind1, and closed boxes represent anti-CD5 (anti-Lyt-1). The overall conclusion in FIG. 12 is that administration of the anti-CD5 (anti-Lyt-1) antibody prior to collagen immunization caused a significant decrease in the resulting severity of arthritis. In all of the treatment groups, the appearance of visible symptoms initiated at approximately 30 days after immunization and progressed linearly until the end of the study. The anti-CD5 (anti-Lyt-1) treatment group began to show ameliorated arthritic symptoms at day 48 and never developed arthritis to the same extent as the other two groups. The onset of arthritis was not significantly delayed by the anti-CD5 (anti-Lyt-1) treatment.

In conclusion, the intravenous administration of a rat monoclonal antibody reactive to the mouse equivalent of CD5, Lyt-1, is able to significantly decrease T lymphocytes in the spleen and in peripheral lymph nodes after a single 0.4 mg/kg dose. This T cell decrease is the probable mechanism for the significant ($p<0.01$) decrease in arthritic severity seen with the same anti-CD5 (anti-Lyt-1) dose prior to type II collagen immunization and provides evidence for therapeutic efficacy of α-CD5 antibodies.

Example 2

The Use Of OX19 Monoclonal Antibody In The Prophylactic Treatment Of Collagen Induced Arthritis In Diabetes-Resistant BB Rats Collagen-induced arthritis (CIA) in the diabetes-resistant Biobreeding (DR BB) rat is a particularly relevant animal model of human rheumatoid arthritis, in that the DR BB rat RT1.Dβ gene encodes a nucleotide sequence homologous to the human HLA-DRβ gene reported to be associated with rheumatoid arthritis susceptibility. In this model, DR BB rats are administered a single intradermal tail injection of heterologous Type II collagen emulsified with incomplete Freund's adjuvant. Development of the arthritis is considerably faster than in the DBA/1J CIA model. Onset of clinical signs occurs 1.5 to 2 weeks after collagen immunization, with peak swelling observed a few days after onset. Incidence is generally quite high (>85% of animals immunized). The swelling is generally severe, involves the entire footpad and ankle joint, and is restricted to the hindlimbs. Histopathological examination has revealed that the arthritis begins as a proliferative synovitis with pannus formation at the joint margins that is followed by a bidirectional erosion of both the outer (unmineralized) and inner (mineralized) layers of cartilage.

This experiment uses the DR BB CIA rat model to assess the efficacy of a MoAb, OX19 directed against the equivalent of the CD5 antigen in the rat. The antibody was administered to the rats prior to immunization with Type II collagen. Normal Sprague-Dawley rats were also treated with a single 0.5 mg/kg i.v. injection and were sacrificed after 3 hours for evaluation of MoAb binding to T cells, or after 2 days for quantitation of T cells in lymphoid tissues using flow cytometry.

A. Effects Of OX19 MoAb On T Cells In Lymphoid Tissues Of Normal Sprague-Dawley Rats OX19 MoAb is a mouse IgG1 directed against the equivalent of rat CD5 antigen present on rat T cells. OX19 hybridoma is available from the European Collection of Animal Cell Cultures (ECACC) and has ECACC No. 84112012. H65 MoAb, a mouse IgG1 reactive against human CD5, was used as an isotype matched negative control. Fluorescein-conjugated antibodies directed against surface antigens on rat pan-T cells (W3/13), CD4 cells (W3/25) and CD8 cells (OX8) were obtained from Accurate Chemical and Scientific Corporation, Westbury, N.Y. for flow cytometric quantitation of T cells in rat lymphoid tissues. Phycoerythrin-conjugated goat anti-mouse IgG1 (Caltag Laboratories, South San Francisco, CA) was used to detect OX19 MoAb bound to rat T cells in a two-color analysis.

Male Sprague-Dawley rats (Simonsen Laboratories, Gilroy, Calif.), 100 to 150 grams, were divided into treatment groups, to which a single i.v. bolus injection of OX19 MoAb (0.5 mg/kg) or control MoAb (0.5 mg/kg) in phosphate buffered saline containing 0.1% Tween 80 (PBS/Tween) was administered. Animals were sacrificed at 3 hours (binding experiment) or 2 days (depletion experiment) after dosing. Single cell suspensions of blood, spleens and lymph nodes were prepared by standard procedures and $1\times10^6$ cells were stained with appropriate antibodies for FACS analysis.

B. Binding Of OX19 MoAb To Rat T Cells In Vivo

Blood, spleen and lymph node cells from one animal in each treatment group were analyzed for the percentages of CD4 and CD8 T cells, and percentage of CD4 and CD8 T cells that also stained positively for surface-bound mouse IgG1 (CD4, CD4/MIgG1, CD8, or CD8/MIgG, respectively). The results are presented in Table 6.

TABLE 6

Binding Of (Anti-CD5) OX19 MoAb To Rat T Cells In Vivo

| | | % Positive Cell | | | |
|---|---|---|---|---|---|
| Tissue | Treatment | CD4 | CD4/mIgG1* | CD8 | CD8/mIgG1* |
| Blood | H65 MoAb | 47.0 | 6.7 | 11.1 | 5.7 |
|  | OX19 | 8.7 | 96.2 | 4.1 | 70.2 |
| Spleen | H65 MoAb | 23.1 | 14.8 | 4.4 | 20.6 |
|  | OX19 MoAb | 16.4 | 84.8 | 3.4 | 73.6 |
| Lymph | H65 MoAb | 66.9 | 4.2 | 7.4 | 6.5 |
| Node | OX19 MoAb | 54.7 | 96.2 | 7.3 | 96.8 |

As shown in Table 6, T cells were depleted from the blood at 3 hours after OX19 MoAb administration. Almost all of the T cells that remained in the blood, and most of those present in the spleen and lymph nodes in the OX19 MoAb-treated rat also stained positively for surface-bound mouse IgG1, indicating that the dose of OX19 MoAb used was sufficient to saturate most of the T cells in these major lymphoid organs. These results provide doses useful in therapeutic applications.

C. Effect of OX19 MoAb Treatment On T Cell Subpopulations In Rat Lympohoid Tissues Blood, spleen and lymph node cells from two animals in each treatment group were analyzed for percentage of pan-T, CD4 and CD8 cells. The results are presented in Table 7 as the mean of the two animals.

TABLE 7

FACS Analysis Of Tissues From OX19 (Anti-CD5) MAb-Treated Rats

| | | % Positive Cells | | |
|---|---|---|---|---|
| Tissue | Treatment | Pan-T | CD4 | CD8 |
| Blood | H65 MoAb | 61.8 | 50.4 | 12.0 |
|  | OX19 MoAb | 47.0 | 37.3 | 8.8 |
| Spleen | H65 MoAb | 36.0 | 25.3 | 7.1 |
|  | OX19 MoAb | 21.5 | 9.9 | 5.0 |
| Lymph Node | H65 MoAb | 74.5 | 62.7 | 13.1 |
|  | OX19 MoAb | 33.8 | 24.9 | 4.3 |

As shown in Table 7, OX19 MoAb treatment resulted in depletion of T cells from all tissues examined as compared to treatment with the control MoAb. These results also provide appropriate doses to be used in therapeutic applications using antibodies according to the invention.

Example 3

Effect Of OX19 MoAb Treatment On Development Of Collagen-Induced Arthritis In DR BB Rats The ability of OX19 MoAb to prevent the development of collagen-induced arthritis was next measured in a manner similar to that described above in the mouse model. Male DR BB/Wor rats (obtained from the University of Massachusetts breeding facility; 8 per treatment group), age 6 weeks, were administered i.v. injections of OX19 MoAb (0.5 mg/kg), control MoAb (0.5 mg/kg) or buffer (PBS/Tween) on day 7 and day 4 prior to immunization at the base of the tail on day 0 with 0.3 mg of bovine Type II collagen emulsified in 0.15 ml of incomplete Freund's adjuvant. Rats were scored daily for arthritis beginning 8 days after collagen immunization. Severity was graded on a scale from 0 to 2, with a score of 1 indicating moderate swelling and a score of 2 indicating severe swelling. An individual animal could have a maximum arthritic severity score of 4 if there was bilateral hindlimb involvement.

Figure 15:
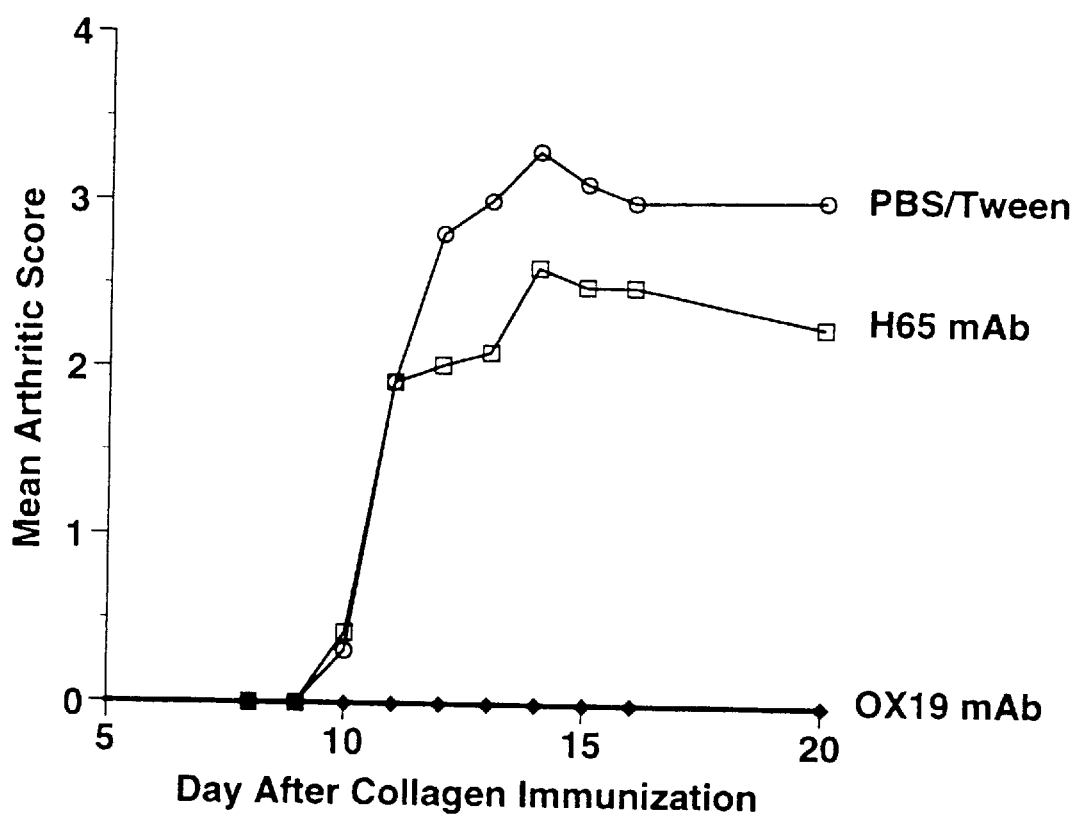
FIG. 15 is a graph of the effects of OX19 MoAb on the severity of DR BB rat collagen-induced arthritis.
Figure 17:
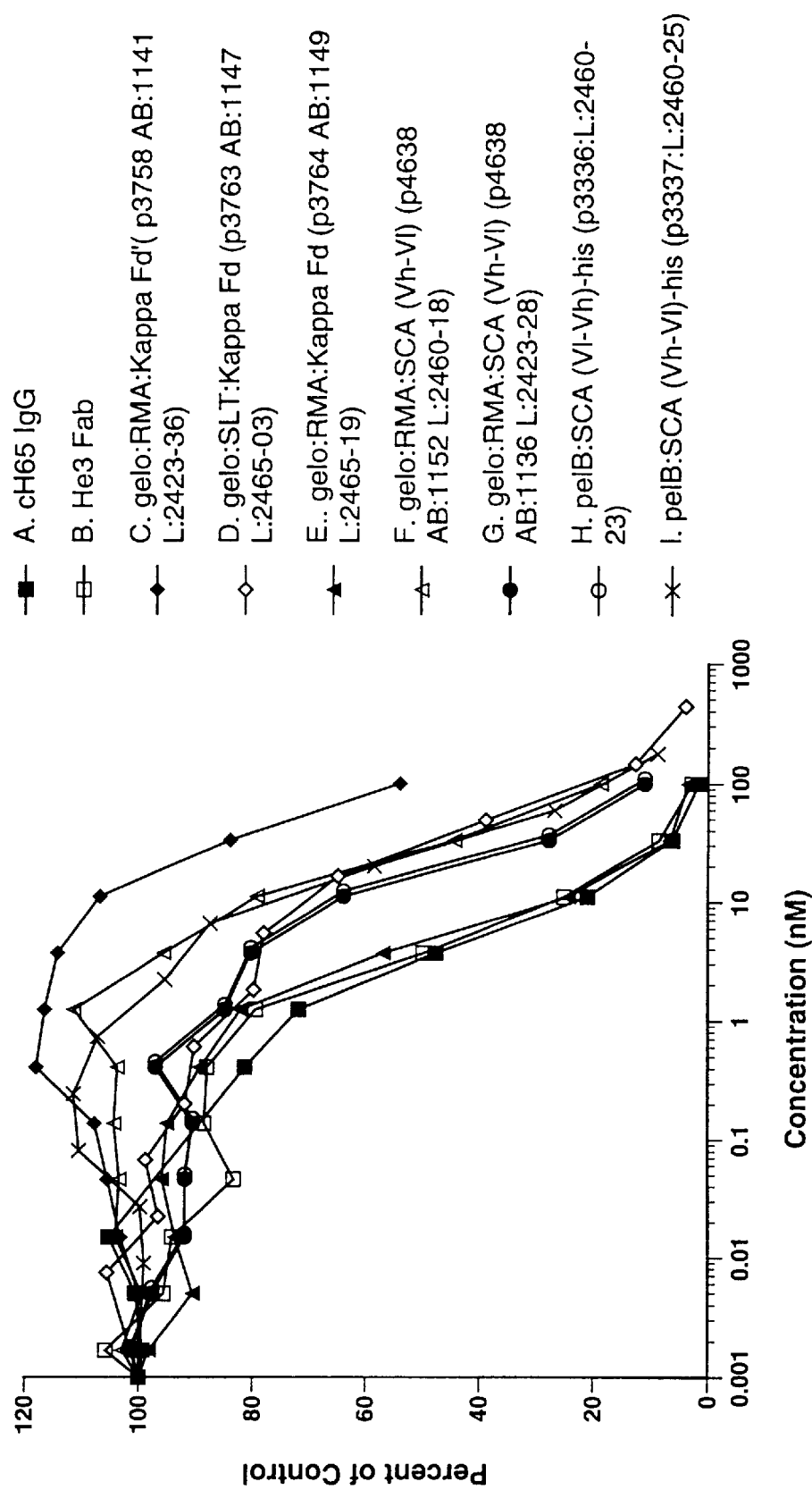
FIG. 17 is a graph showing results of competitive binding experiments using humanized single chain antibodies and he3 Fab to compete $^{123}$I-labeled cH65 IgG; open circles represent the pING3326 single chain antibody ($V_L$-$V_H$); open squares represent the pING3337 single chain antibody ($V_H$-$V_L$); and closed circles represent he3 Fab.
Figure 18:
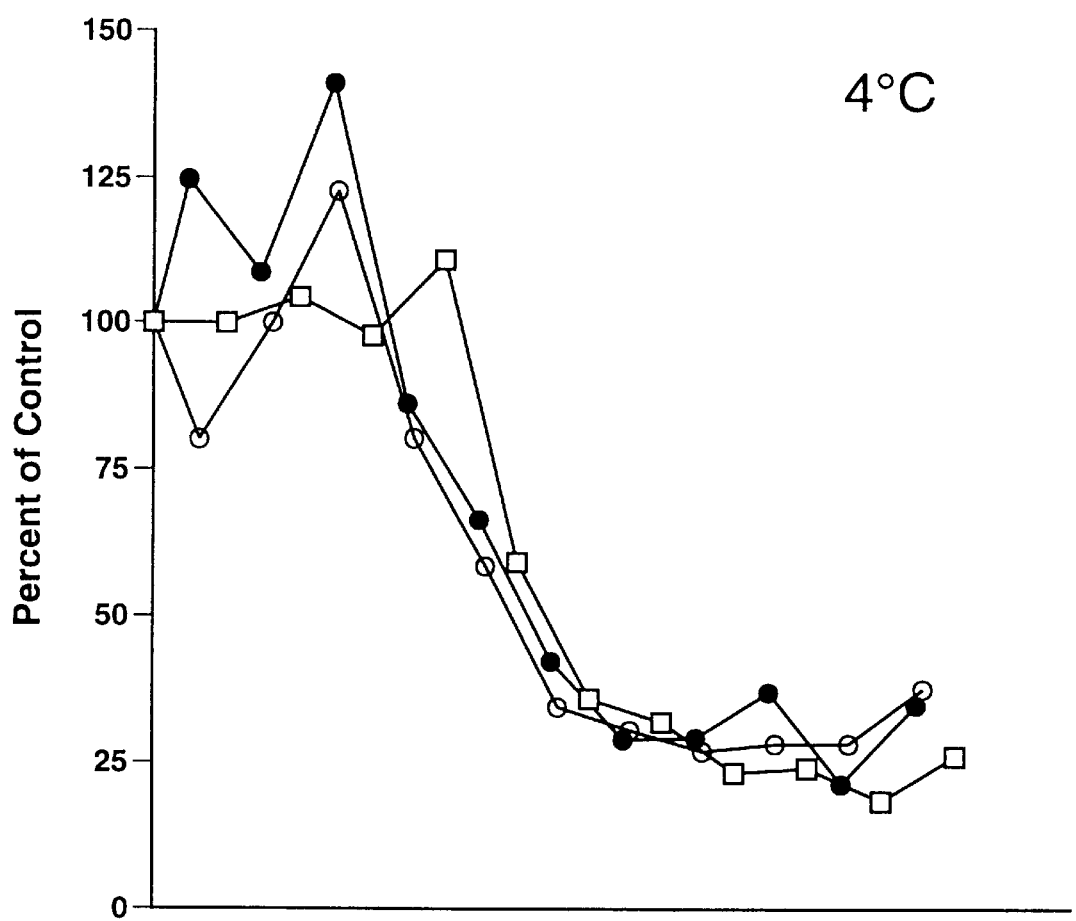
FIG. 18 is a graph showing results of a competitive binding experiment using single chain antibodies and single chain antibody fusion proteins.

The changes in arthritic score during the course of the study are shown in FIG. 15 and the arthritic incidence for each treatment group is presented in Table 8 and provides additional evidence of the therapeutic efficacy of anti-CD5 antibodies.

TABLE 8

Effect Of OX19 (Anti CD5) MoAb Treatment On Arthritis Incidence

| TREATMENT | Total arthritics (1 or both hind limbs) | Total Arthritics (Both hind limbs) | Score of "2" (1 or both hind limbs) | Score of "2" (Both hind Limbs) |
|---|---|---|---|---|
| PBS/Tween | 7/8 (88%) | 7/8 (88%) | 7/8 (88%) | 5/8 (63%) |
| Control MoAb | 7/8 (88%) | 4/8 (50%) | 6/8 (75%) | 4/8 (50%) |
| OX19 MoAb | 0/8 (0%) | 0/8 (0%) | 0/8 (0%) | 0/8 (0%) |

Control (buffer and control MoAb-treated) rats developed severe, predominantly bilateral hindlimb arthritis between days 10 and 14 with high incidence (88% for both groups). Treatment with OX19 MoAb completely prevented development of arthritis (0% incidence).

In conclusion, a 0.5 mg/kg intravenous dose of a mouse MoAb directed against the rat equivalent of CD5 was found to saturate and subsequently deplete T cells from lymphoid tissues of normal rats. This T cell depletion is the probable mechanism for the complete inhibition of arthritis development observed when the MoAb was administered prior to Type II collagen immunization in DR BB rats and provides additional evidence for the therapeutic efficacy of anti-CD5 antibodies.

Example 4

Preparation Of XMMLY-H65 Anti-Pan T Cell Immunoglobulin

The murine monoclonal antibody produced by cell line XMMLY-H65 (hereinafter referred to as "MoAbH65") is reactive with the human CD5 antigen. The cell line XMMLY-H65 was deposited with the American Type Culture Collection, 12301 Parklawn Drive, Rockville, Md., 20852 and designated as Accession No. HB9286.

MoAbH65 was produced after immunization of BALB/c mice with the human T-cell line HSB-2 originally isolated from a patient with T-cell acute lymphocytic leukemia. Adams, et al. *Can. Res.* 28:1121 (1968). The murine myeloma cell line P3 7 NS/1-Ag-1-4 of Kohler et al. *Eur. J. Immunol.* 6:292 (1976) was fused with spleen cells from an immunized mouse by the technique of Galfre et al., *Nature* 266:550 (1977). One of the resulting hybrid colonies was found to secrete a MoAb that recognizes a pan-T-lymphocyte antigen with a molecular weight of 67 kD, expressed on approximately 95% of peripheral T-lymphocytes [Knowles, *Leukocyte Typing II,* 1, (E.

Reinherz, et al. eds., Springer Verlag (1986)]. This antigen is not present on the surface of any other hematopoietic cells, and the antibody itself has been tested for binding to a large range of normal human tissues and found to be negative for all cells except for T-lymphocytes and a subpopulation of B lymphocytes.

The H65 antibody-producing hybrid cell line was cloned twice by limiting dilution and was grown as ascites tumors in BALB/c mice.

MoAbH65 was purified from mouse ascites by a modification of the method of Ey et al. *Immunochem.* 15:429 (1978). In brief, the thawed mouse ascites was filtered to remove lipid-like materials and was diluted with 2 to 3 volumes of 0.14M $NaPO_4$, pH 8.0, before application onto an immobilized protein A-Sepharose column of appropriate size. The unbound materials were removed from the column by washing with 0.14M $NaPO_4$, pH 8.0, until no further change in absorbance at 280 nm was seen. A series of column washes with 0.1M sodium citrate (pH 6.0, pH 5.0, pH 4.0, and pH 3.0) were then performed to elute bound antibody.

Peak fractions were pooled, adjusted to pH 7.0 with saturated Tris base, and concentrated by using a cell stirred with Amicon YM10 membrane (Amicon, Lexington, N.Y.). An antibody solution was then dialyzed against phosphate-buffered saline (PBS), pH 7.0, and was stored frozen at $-70°$ C.

MoAb H65 is of the $IgG_1$ subclass, as determined by double diffusion in agar with the use of subclass-specific antisera (Miles-Yeda, Ltd. Rehovot, Israel). The serologic characteristics of this antibody and the biochemical characteristics of the gp67 (i.e., CD5) antigen were examined during the First International Workshop on Human Leukocyte Differentiation Antigens (Paris, 1982). MoAb H65 (workshop number: T34), and nine other MoAbs were found to have the same serologic pattern and to immunoprecipitate the gp67 antigen. Knowles, in Reinherz, et al., *Leukocyte Typing II*, 2: 259–288 (Springer-Verlag, 1986). In other studies, MoAb H65 has been shown to block the binding of FITC-conjugated anti-Leu-1 (Becton Dickson, Mountain View, Calif.) on CD5+cells indicating that both antibodies recognize the same epitope on the CD5 molecule or determinants that are located in such a configuration as to result in blocking by steric hindrance.

Example 5

Depletion Of Human T Cells From SCID Mice By Treatment With H65 MoAb

Severe combined immunodeficient (CB.17 scid/scid; SCID) mice maintain human lymphoid cells for several months following transplantation of human peripheral blood mononuclear cells (PBMC). Such chimeric mice, referred to as PBMC/SCID mice, have functional human cells, as shown by the presence of human Ig in their serum. PBMC/SCID mice maintain human T cells in tissues such as spleen and blood. Human T cells present in PBMC/SCID mice are predominantly of a mature phenotype and express T cell antigens, including CD3, CD5, CD7, and CD4 or CD8. In addition, most T cells appear to be activated memory cells, as judged by the expression of HLA-DR and CD45RO. These engrafted T cells appear to be functional since (a) they may provide help to B cells to produce anti-tetanus toxoid antibodies, (b) they produce soluble interleukin-2 receptor (sIL-2R) which may be detected in plasma, and (c) they proliferate in response to mitogenic anti-human CD3 monoclonal antibodies supplemented with IL-2 in vitro.

Because of the presence of human T and B cells, PBMC/SCID mice offer an in vivo model system in which to evaluate the efficacy of anti-human T cell drugs, such as H65 MoAb, a mouse IgGI directed against human CD5. The therapeutic efficacy of such anti CD5 antibodies was demonstrated in Examples 1–3 above.

The SCID mice were obtained from Taconic, Germantown, N.Y., and at 6 to 7 weeks of age were injected with 200 mg/kg cyclophosphamide intraperitoneally (i.p.) to ensure engraftment of human PBMC. Two days later, 25 to $40 \times 10^6$ human PBMC, isolated by Ficoll-Hypaque density gradient centrifugation from lymphapheresis samples obtained from normal donors (HemaCare Corporation, Sherman Oaks, Calif.), were injected intraperitonealy.

At 2 to 3 weeks after PBMC injection, the mice were bled from the retro-orbital sinus and levels of human immunoglobulin (Ig) and human sIL-2R in plasma were quantified using sandwich ELISAs. Mice with low or undetectable levels of these human proteins were eliminated from the study and the remainder were divided into the various treatment groups (6 per group). The mice were then administered H65 MoAb (0.2 or 0.02 mg/kg/day), H65-based F(ab')$_2$ fragment (2 mg/kg/day) or vehicle (buffer) intravenously (i.v.) for 10 consecutive daily injections. One day after the last injection, the mice were bled and spleens were collected. Single cell suspensions of blood cells and splenocytes were prepared by standard methods. Recovered cells were then assayed for human T cell surface markers using flow cytometry.

Cells ($2 \times 10^5$) were stained with the following FITC- or PE-conjugated Abs (Becton-Dickinson, Mountain View, Calif.): HLe-1-FITC (anti-CD45), Leu-2-FITC (anti-CD8), and Leu-3-PE (anti-CD4). Samples were analyzed on a FACScan using log amplifiers. Regions to quantify positive cells were set based on staining of cells obtained from naive SCID mice. The absolute numbers of human antigen-positive cells recovered from SCID tissues were determined by multiplying the percent positive cells by the total number of cells recovered from each tissue sample. The total number of leukocytes in blood was calculated using a theoretical blood volume of 1.4 ml/mouse. Statistical comparisons between treatment groups were made using the Mann-Whitney U test.

The number of human T cells (CD4 plus CD8 cells) recovered from spleens and blood of PBMC/SCID mice following treatment with H65 MoAb or vehicle (control) is shown in FIGS. 13 A and 13 B, wherein the dash in the figures represents the median value. Significantly (pL 0.05) lower numbers of T cells were recovered from spleens and blood of mice treated with either 0.2 or 0.02 mg/kg/day H65 MoAb as compared to vehicle-treated mice.

Figures 14A, 14B:
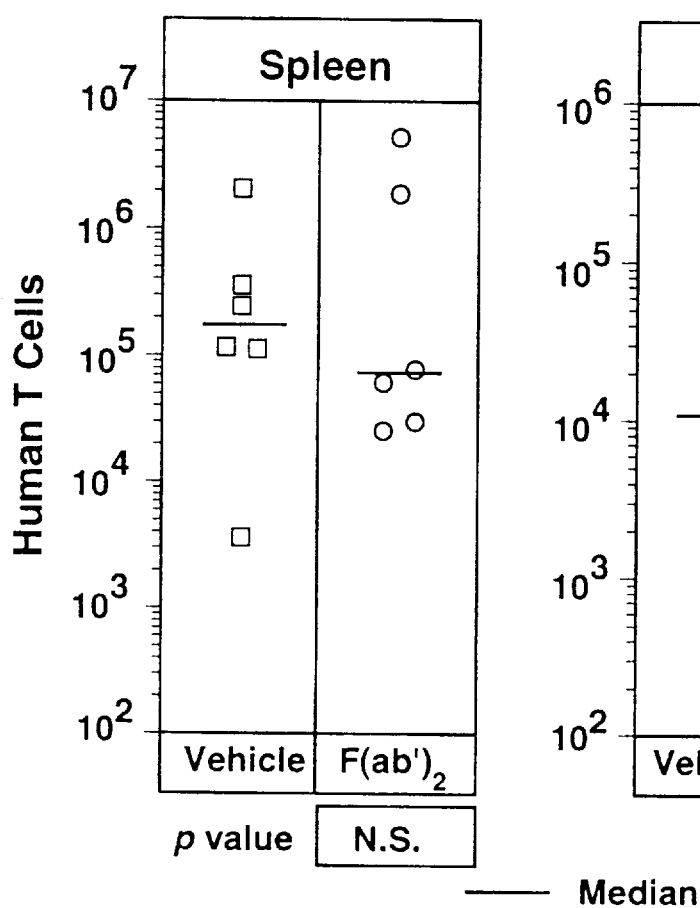
FIGS. 14A and 14B are schematic depictions of human T cell recovery in spleen and blood, respectively from PBMC/SCID mice following treatment with H65-based F(ab')$_2$ fragment.

In contrast, treatment with 2 mg/kg/day of an H65-based F(ab')$_2$ fragment did not significantly deplete human T cells from spleens or blood, even though a 10 to 100-fold higher dose was used (FIGS. 14A and 14B). Median values in FIGS. 14A and B are indicated by dashes.

These results indicate that an anti-human CD5 MoAb depletes human T cells in an experimental animal model in a manner similar to the depletion of T-cells, demonstrated in Examples 1–3 with anti-mouse as anti-rat CD5. Because anti-CD5 antibodies, including H65, were therapeutically effective, humanized anti-CD5 antibodies with comparable affinities but without significant immunogencity would be useful. The ability of this MoAb to deplete human T cells from SCID mice is apparently dependent on the Fc portion of the MoAb, as an F(ab')$_2$ fragment was ineffective.

Example 6

Identification Of Low Risk Residues in A Mouse Variable Domain

A method of the present invention was utilized to prepare modified antibody variable domains by identifying low risk residues in a mouse monoclonal antibody variable domain, designated H65, which may be modified without diminishing the native affinity of the domain for antigen while still reducing its immunogenicity with respect to humans.

The light and heavy chains of the variable domain of H65 were determined to most closely resemble the consensus sequences of subgroup 1 ("hK1") of the human kappa chains and subgroup 3 ("hH3") of the human heavy chains, respectively. The H65 V/J-segments of the light and heavy chain sequences are aligned with the two human subgroup consensus sequences in FIGS. 6A and 6B. The H65 sequences are also contained in SEQ ID NOS: 2G and 28.

In FIGS. 6A and 6B, upper and lower case letters denote the degree of conservation at any given position. For example, an "A" indicates that alanine is present at that position in about 90% to about 100% of the known human sequences of that subgroup (excluding small, incomplete fragments); whereas an "a" indicates that alanine is present only about 50% to about 90% of the time at that position in known human sequences of that subgroup. A lower case "x" indicates conservation of the amino acid at that position less than about 50% of the time.

The line labelled "bind" in FIGS. 6A and 6B shows which residues directly affect (−) or do not directly affect (+) antigen binding of CDR loops. The "bury" line indicates exposed (+), buried (−), or interfacial (=) residues. On either the "bind" or "bury" line, a "0" indicates a residue of intermediate significance in terms of antigen binding or placement of the residue, respectively.

FIGS. 6A and 6B reveal that the mouse H65 sequences differ from the human consensus sequences with which they are aligned at a total of 94 positions. Sixty-nine of these differences occur at moderate-risk (15 positions) or high risk (54 positions) positions suggesting that the mouse residue at that position may be important for the function of the antibody. The "M/H" line of FIGS. 6A and 6B specifically indicates which positions differ between the two pairs of aligned sequences. Based on the considerations of the level of risk and the degree of conservation of the human residue at each position presented in the foregoing paragraphs, those residues in the H65 sequences designated M or m in the M/H line are identified as residues to be kept "mouse" in a humanized sequence, while those designated H or h are identified as residues to be changed to "human."

Twenty-five differences occur at low risk positions at which the mouse and human sequences differ. At thirteen of those positions (designated "H" on the M/H lines of FIGS. 6A and 6B) the mouse residue aligns with a human consensus amino acid which is highly conserved. Therefore, the mouse residue at that position is identified as one to be changed to the conserved human residue.

At four low risk positions (designated "m") in which the mouse and the human sequences differ, the mouse residue aligns with a human consensus amino acid which is moderately conserved. However, since the mouse residue is found at that position in other actual sequences of human antibodies, the positions are identified as ones to be kept "mouse." At seven low risk positions (designated "h"), the mouse residue aligns with a human consensus amino acid which is moderately conserved but the mouse residue is not found at that position in an actual human antibody sequence in Kabat. Therefore, those positions are identified as ones to be changed to "human."

At one low risk position (designated "m") in which the mouse and human sequences differ, the mouse residue aligns with a human consensus amino acid which is poorly conserved. Therefore, that position is identified as one to be kept "mouse."

The "prop" lines of FIGS. 6A and 6B set out the sequences of the light and heavy chains of the H65 antibody variable domain in which the residues identified by the methods of the present invention as those which may be modified without diminishing the native affinity of the H65 variable domain for CD5 are changed to human residues. Thus, the "prop" lines of FIGS. 6A and 6B set out the amino acid sequences of humanized light (SEQ ID NO: 27) and heavy chains (SEQ ID NO: 29) of the H65 antibody variable domain.

Example 7

A. Synthesis Of Low Risk H65 V/J Segments Of Light And Heavy Chain

Based on the low risk humanized amino acid sequences of the V/J-segments of the light and heavy chains of the H65 antibody variable domain described in Example 6, synthetic genes for heavy and light chain V/J-segments of H65 were synthesized. The humanized amino acid sequences were reverse-translated with the PCGENE package (Intelligenetics, Mountain View, Calif.). Amino acid codons for each position were chosen which were identical to the mouse codon at positions where the mouse amino acid residue was maintained, or which matched as closely as possible a codon in a native antibody gene based on those gene sequences published in Kabat. For expression of humanized whole antibody in mammalian cells, polynucleotides encoding the native mouse leader sequences were included as part of the humanized genes. Each gene, heavy or light, was assembled from six overlapping oligonucleotides and amplified by PCR. Each oligonucleotide was synthesized with a Cyclone Model 8400 DNA Synthesizer (Milligen/Biosearch, Burlington, Mass.). Restriction sites were introduced into the amplified DNA segments for cloning into the final expression vectors for antibody genes (heavy or light). A SalI restriction site was introduced into each V-region upstream of the initiation codon, ATG. A BstEII restriction site was introduced into the 3'-end of the heavy chain J-region, while a HindIII site was introduced into the 3'-end of the light chain J-region.

B. Assembly Of Low Risk Heavy Chain Expression Vector

The humanized V- and J-segments of the heavy chain were assembled from six oligonucleotides, HUH-G1, HUH-G2, HUH-G3, HUH-G4, HUH-G5, and HUH-G6, the sequences of which are contained in FIGS. 7A and 7B and in SEQ ID NOS: 36 to 41, respectively. The oligonucleotides were amplified with PCR primers H65G-2S and H65-G2 (SEQ ID NOS: 42 and 43, respectively). Oligonucleotides greater than 50 bp in length were purified on a 15% polyacrylamide gel in the presence of 25% urea. DNA strand extension and DNA amplification was accomplished with a Taq polymerase and the GeneAmp Kit used according to the manufacturer's instructions (Perkin-Elmer Cetus, Germany). Oligonucleotides containing the synthetic humanized antibody gene were mixed in pairs (HUH-G1+

HUH-G2, HUH-G3+HUH-G4, and HUH-G5+HUH-G6) in 100 μl reactions with 1 μg of each DNA, 2.5 U Taq polymerase, 50 mM KCl, 10 mM TRIS-Cl pH 8.3, 1.5 mM MgCl$_2$, and 200 uM each dNTP. The tube was incubated in a Coy TempCycler for 1 minute at 94° C., 2 minutes at 55° C. and 20 minutes at 72° C. A portion of each reaction product (40 μl) was mixed in pairs (HUH-G1,2+HUH-G3,4; HUH-G3,4 +HUH-G5,6), 2.5 U Taq was added and the tubes were re-incubated at 94° C. for 1 minute, 55° C. for 2 minutes and 72° C. for 20 minutes. The heavy chain gene was then assembled by mixing an equal amount of the HUH-G1,2,3,4 reaction product with the HUH-G3,4,5,6 reaction product and bringing the volume to 100 μl of 2.5 U Taq, 50 mM KCl, 10 mM TRIS-Cl pH 8.3, 1.5 mM MgCl$_2$, 200 uM each dNTP, and 0.5 μg of each amplification primer H65G-2S and H65-G2. The reaction was overlaid with mineral oil, and the cycle profile used for amplification was: denaturation 94° C. for 1 minute, annealing 55° C. for 2 minutes, and primer extension at 72° C. for 3 minutes. Primer extension was carried out for 30 cycles. The DNA sequence of the assembled V/J-region is contained in FIG. 8A and in SEQ ID NO: 46. The assembled V/J-region was cut with SalI and BstEII, purified by electrophoresis on an agarose gel, and assembled into a heavy chain expression vector, pING4612, which is similar to that described for heavy chain expression in Robinson et al., *Hum. Antib. Hybridomas*, 2:84 (1991) and described in detail in co-pending, co-owned U.S. patent application Ser. No. 07/659,409 filed on Sep. 6, 1989, both of which are incorporated by reference herein.

C. Assembly Of Low Risk Light Chain Expression Vector

The humanized V- and J-segments of the light chain were also assembled from six oligonucleotides, $H65K-1, HUH-K1, HUH-K2, HUH-K3, HUH-K4 and HUH-K5, the sequences of which are contained in FIGS. 7A and 7B and in SEQ ID NOS: 30 to 35, respectively. The oligonucleotides were amplified with PCR primers H65K-2S and JK1-HindIII (SEQ ID NOS: 44 and 45, respectively). Oligonucleotides containing the synthetic humanized antibody gene were mixed in pairs ($H65K-1+HUH-K1, HUH-K2+HUH-K3, and HUH-K4+HUH-K5) and incubated as described above for the heavy chain. A portion of each reaction product (40 μl) was mixed in pairs ($H65K-1/HUH-K1+HUH-K2,3; HUH-K2,3+HUH-K4,5) and treated as above. The light chain gene was then assembled by amplifying the full length gene with PCR primers H65K-2S and JK1-HindIII as outlined above for the heavy chain. The DNA sequence of the assembled V/J-region is contained in FIG. 8B and in SEQ ID NO: 47. The assembled V/J-region was cut with SalI and HindIII, purified by electrophoresis on an agarose gel, and assembled into a light chain antibody expression vector, pING4614 similar to those described for light chain expression in Robinson et al., supra. and in U.S. patent application Ser. No. 07/659,409, supra.

D. Transient Expression Of Low Risk Humanized H65 he1 IgG

Expression vectors containing the low risk humanized H65 (he1) light chain and heavy chain sequences under the control of the Abelson Leukemia virus LTR promoter (described in Robinson et al., supra, and in U.S. patent application Ser. No. 07/659,409, supra) and 3' untranslated regions from human gamma-1 (for heavy chain) and mouse kappa (for light chain) were transfected by lipofection into a CHO-K1 strain which expresses the SV40 T antigen. Following treatment with lipofection reagent (Bethesda Research Labs, Gaithersburg, Md.) plus DNA for 5 hours at 37° C., Ham's F12 media containing fetal bovine serum (FBS, final FBS conc.=10%) was added and the cells were incubated for an additional 48 hours. Following this incubation period, the FBS-supplemented media was removed and replaced with serum-free media (HB-CHO) (Irvine Scientific, Irvine, Calif.) and the cells were incubated for an additional 7 days. As a control, the CHO-K1 cells were also transfected with chimeric H65 light chain and heavy chain (each consisting of unmodified mouse V/J-segments fused to a human C-segment) in expression vectors similar to those described above. Following incubation, the supernatants were collected and tested by ELISA for the presence of secreted IgG. All of the supernatants contained about 0.03–0.06 μg/ml IgG.

E. Competition Binding And Affinity Measurements Of Humanized IgG For CD5

The hel H65 antibody modified according to the foregoing methods was tested to determine whether it retained native affinity for antigen. Its binding capability was compared to that of a chimeric H65 IgG antibody which has the same affinity for CD5 as unmodified H65 mouse antibody.

The humanized H65 (he1) and chimeric H65 IgG (cH65) from transient transfections described above were concentrated from 4 ml to a final volume of 100 μl by centrifugation using a Centricon 30 (Amicon, Amicon Division of W.R. Grace and Co., Beverley, Mass.) at 4° C. Both he1 and cH65 IgG concentrates were then washed once with 1.0 ml of phosphate buffered saline (PBS), pH 7.2 and reconcentrated to approximately 100 μl. As a control, HB-CHO culture media alone (CM) or media supplemented with purified cH65 (CM+cH65) was concentrated in a similar manner. The final concentrations of he1 and cH65 IgG were determined by ELISA (anti-human Kappa pre-coat, peroxidase-labelled anti-human gamma for detection) using chimeric IgG as a standard.

20 μg of chimeric H65 IgG was iodinated by exposure to 100 μl lactoperoxidase-glucose oxidase immobilized beads (Enzymobeads, BioRad), 100 μl of PBS, 1.0 mCi $^{125}$I (Amersham, IMS30), 50 μl of 55 mM b-D-glucose for 45 minutes at 23° C. The reaction was quenched by the addition of 20 μl of 105 mM sodium metabisulfite and 120 mM potassium iodide followed by centrifugation for 1 minute to pellet the beads. $^{125}$I-cH65 IgG was purified by gel filtration using 7 mls of sephadex G25 using PBS (137 mM NaCl, 1.47 mM KH$_2$PO$_4$, 8.1 mM Na$_2$HPO$_4$, 2.68 mM KCl at pH 7.2–7.4) plus 0.1% BSA. $^{125}$I-cH65 IgG recovery and specific activity were determined by TCA precipitation.

F. Competitive Binding Of hel IgG and cH65 IgG

Molt4-M cells, which express CD5 on their surface, were plated on 96 well V-bottom plates at a density of 3×10$^5$ cells per well and pelleted by centrifugation. The medium was decanted, and 100 μl of purified cH65 IgG at final concentrations from 200 nM to 0.0017 nM (diluted in 3-fold steps) in "DHB" [DMEM (Dulbecco's Modified Eagle's Medium) +1% BSA+10 mM Hepes, pH 7.2] was added to each well, followed by 100 μl of $^{125}$I-cH65 IgG (final concentration= 0.1 nM) in DHB. For single point determinations, 50–100 μl of the Centricon® concentrates were added to the wells as follows: hH65 (final concentration=0.54 nM), cH65 (final concentration=0.22 nM), CM +purified cH65 IgG (final concentration=30 nM) and CM alone. These were followed by addition of $^{125}$I-cH65 IgG (final concentration=0.1 nM). Binding was allowed to proceed for 5 hours at 4° C. At the end of 5 hours, binding was terminated by three washes with ice cold DHB using centrifugation to pellet cells. Radioactivity was determined by solubilizing bound $^{125}$I-cH65 IgG with 1N NaOH and counting in a Beckman Gamma 8000 (Beckman Instruments, Fullerton, Calif.).

Figure 9:
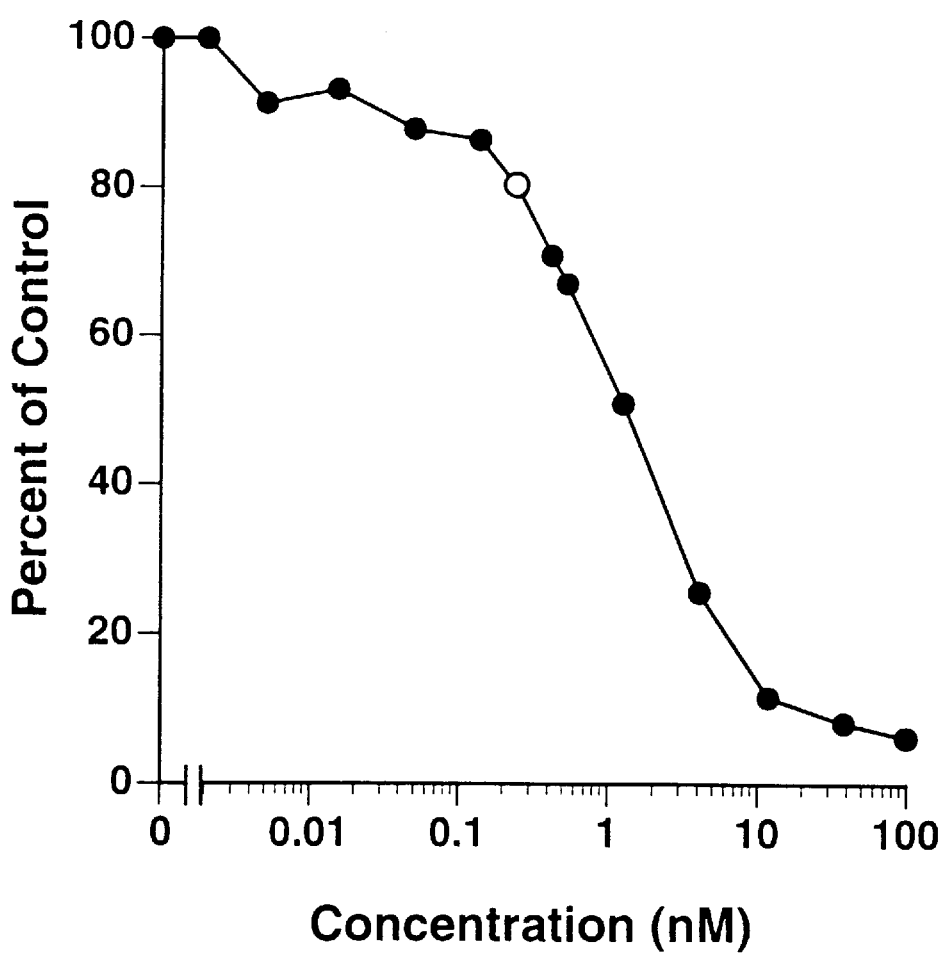
FIG. 9 is a graph of the results of a competitive binding assay showing that the H65 antibody variable domain modified by a method according to the present invention retains the antigen-binding capability of the natural H65 antibody variable region.

Purified cH65 IgG effectively displaced $^{125}$I-cH65 IgG binding with an $ED_{50}$ of approximately 1.0 nM as shown in FIG. 9, wherein open circles indicate cH65, shaded squares indicate hH65 and shaded triangles indicate CM+purified cH65. The he1 IgG was as effective in displacing $^{125}$I-cH65 IgG as were purified cH65 and CM+purified cH65 IgG, at their respective concentrations. No competition was observed with CM as expected. These results demonstrate that the low-risk changes made in the course of modification of he1 IgG did not diminish the binding affinity of this antibody for the CD5 antigen.

G. Fluorescence-Activated Cell Sorter-Based Competition Assay

Additionally a fluorescence-activated cell sorter based competitive assay described by Knebel et al., *Cytometry Supp.*, 1:68 (1987), incorporated by reference herein, was used to demonstrate that mouse H65 binds CD5 with the same affinity as cH65. The results of 3 such experiments are set forth in Table 9 below, wherein H65 affinity was set at 100% and the relative affinity of cH65 is expressed based on the 100% baseline.

TABLE 9

| Experiment No. | cH65 Affinity Relative to H65 (100%) |
| --- | --- |
| 1 | 113% |
| 2 | 106% |
| 3 | 96.3% |
| Mean of 3 Expts ± SD | 105% ± 8.2% |

Example 8

Identification Of Moderate Risk Residues In Mouse Variable Domain

The human consensus sequences in which moderate risk residues are converted from mouse residues to human residues are represented in FIGS. 16A and 16B as lines labelled hKl (i.e., subgroup 1 of the human kappa chain) and hH3 (i.e., subgroup 3 of the human heavy chain).

Symbols in this Figure, for conservation and for risk are used in accordance with FIGS. 6A and 6B.

In the line labelled "mod", a dot (.) represents a residue which may be mutated from "mouse" to "human" at moderate risk. There are 29 such moderate risk positions.

The mouse residue matches the human consensus residue more than 50% of the time at 131 positions (102 positions match 90%–100% and 29 positions match 50% to 90%). These positions were not changed.

The lines labelled M/H in FIGS. 16A and 16B indicate the 91 positions which differed significantly between the mouse and human sequences (i.e., where the human sequences have the mouse residue less than 50% of the time). Moderate risk positions, designated m in the M/H line, were kept "mouse"; whereas those designated H or h were changed to human. The 25 low risk positions which were already human-like or which were previously humanized (as described supra in Example 6) are designated "·" in the M/H line. Finally, the 54 high risk positions in which the mouse and human residues did not match are designated M and are kept "mouse".

Fifteen differences occur at moderate risk positions at which the mouse and human sequences differ. At ten of those positions (designated "H" on the M/H lines of FIG. 6) the mouse residue aligns with a human consensus amino acid which is highly conserved. Therefore, the mouse residue at that position is identified as one to be changed to the conserved human residue.

At moderate risk positions (designated "m") in which the mouse and the human sequences differ, the mouse residue aligns with a human consensus amino acid which is moderately conserved. However, since the mouse residue is found at that position in other actual sequences of human antibodies (e.g., in Kabat), the positions are identified as ones to be kept "mouse." Although there are no such positions in this particular sequence, such positions may occur in other antibodies.

At four moderate risk positions (designated "h"), the mouse residue aligns with a human consensus amino acid which is moderately conserved but the mouse residue is not found at that position in an actual human antibody sequence in Kabat. Therefore, that position is identified as ones to be changed to "human."

At one moderate risk position (designated "m") in which the mouse and human sequences differ, the mouse residue aligns with a human consensus amino acid which is poorly conserved. Therefore, that position is identified as one to be kept "mouse."

Example 9

A. Assembly Of Moderate Risk Heavy Chain Expression Vectors

The humanized H65 heavy chain containing the moderate risk residues was assembled by a strategy similar to that for the low risk residues. The moderate-risk expression vector was assembled from intermediate vectors. The six oligonucleotide sequences disclosed in FIG. 7B and labelled HUH-G11 (SEQ ID NO: 56), HUH-G12 (SEQ ID NO: 57), HUH-G3, HUH-G4, HUH-G5, and HUH-G6 were assembled by PCR. Oligonucleotides containing the synthetic humanized antibody gene were mixed in pairs (HUH-GII+HUH-G12, HUH-G3+HUH-G4, and HUH-G5+HUH-G6) in a 100 μl reaction with 1 μg of each DNA and filled in as described above. A portion of each reaction product was mixed in pairs (HUH-Gll, 12+HUH-G3, 4; HUH-G3, 4+HUH-G5, 6), 2.5 U Taq was added and samples were reincubated as described above. The V-J-region was assembled by mixing equal amounts of the HUH-G11, 12, 3, 4 reaction product with the HUH-G3, 4, 5, 6 product, followed by PCR with 0.5 ug of primers H65G-2S and H65-G2 as described above. The reaction product was cut with SalI and BstEII and cloned into the expression vector, similar to that described for heavy chain in Robinson et al., *Hum. Antibod. Hybridomas* 2:84 (1991), generating pING4617. That plasmid was sequenced with Sequenase (USB, Cleveland), revealing that two residues were altered (a G to A at position 288 and a A to T at position 312, numbered from the beginning of the leader sequence). The correct variable region was restored by substitution of this region from pING4612, generating the expected V-region sequence in pING4619.

An intermediate vector containing the other moderate-risk changes was constructed by PCR assembly of the oligos HUH-G13, HUH-G14, HUH-G15, and HUH-G16 (FIG. 7 and SEQ ID NOS: 58–61, respectively). Oligos HUH-G13+ HUH-G14 and HUH-G15+HUH-G16 were mixed and filled in with Vent polymerase (New England Biotabs) in a reaction containing 10 mM KCl, 20 mM TRIS pH 8.8, 10 mM $(NH_4)_2SO_2$, 2 mM $MgSO_4$, 0.1% Triton X-100, 100 ng/ml BSA, 200 uM of each dNTP, and 2 units of Vent polymerase in a total volume of 100 μl. The reaction mix was incubated at 94° C. for 1 minute, followed by 2 minutes at 50° C. and 20 minutes at 72° C. The reaction products (40 μl) were mixed and amplified with the oligonucleotides H65-G13 and H65-G2 with Vent polymerase in the same reaction buffer and amplified for 25 cycles with denaturation at 94° C. for 1 minute, annealing at 50° C. for 2 minutes and polymerization at 72° C. for 3 minutes. The reaction product was treated with T4 polymerase and then digested with AccI. The 274 base pair (bp) fragment was purified on an agarose gel and ligated along with the 141 bp SalI to AccI fragment from pING4619 into pUC18 cut with SalI and SmaI to generate pING4620. pING4620 contains the entire signal sequence, V-region, and J-region of the moderate-risk H65 heavy chain.

The final expression vector for the moderate-risk H65 heavy chain, pING4621, was assembled by cloning the SalI to BstEII fragment from pING4620 into the same expression vector described above.

B. Assembly Of Moderate-Risk Light Chain Expression Vector

The moderate-risk humanized V- and J-segments of the light chain were assembled from six oligonucleotides, $H65K-1, HUH-K7, HUH-K6, HUH-K8, HUH-K4 and HUH-K5. The sequences of HUH-K7, HUH-K6 and HUH-K8 are set out in SEQ ID NOS: 62–64, respectively and FIG. 7. The oligonucleotides were amplified with PCR primers H65K-2S and JK1-HindIII. Oligonucleotides containing the synthetic humanized antibody gene were mixed in pairs ($H65-K1+HUH-K7, HUH-K6+HUH-K8, and HUH-K4+ HUH-K5) and incubated with Vent polymerase as described for the moderate-risk heavy chain. A portion of each reaction product (40 ul) was mixed in pairs ($H65H-K1/HUH-K7+ HUH-K6, 8; HUH-K6, 8+HUH-K4, 5) and filled in as above. The light chain gene was then assembled by amplifying the full length gene with the PCR primers H65K-2S and JK1-HindIII with Vent polymerase for 25 cycles as outlined above. The assembled V/J region was cut with SalI and HindIII, purified by electrophoresis on an agarose gel, and assembled into a light chain antibody expression vector, pING4630.

C. Stable Transfection Of Mouse Lymphoid Cells For The Production Of Moderate Risk (he3) Antibody The cell line Sp2/0 (American Type Culture Collection Accession No. CRL1581) was grown in Dulbecco's Modified Eagle Medium plus 4.5 g/l glucose (DMEM, Gibco) plus 10% fetal bovine serum. Media were supplemented with glutamine/penicillin/streptomycin (Irvine Scientific, Irvine, Calif.).

The electroporation method of Potter, H., et al., *Proc. Natl. Acad. Sci., USA*, 81:7161 (1984) was used. After transfection, cells were allowed to recover in complete DMEM for 24–48 hours, and then seeded at 10,000 to 50,000 cells per well in 96-well culture plates in the presence of selective medium. Histidinol (Sigma) selection was at 1.71 μg/ml, and mycophenolic acid (Calbiochem) was at 6 μg/ml plus 0.25 mg/ml xanthine (Sigma). The electroporation technique gave a transfection frequency of $1-10\times10^{-5}$ for the Sp2/0 cells.

The he3 light chain expression plasmid pING4630 was linearized by digestion with PvuI restriction endonuclease and transfected into Sp2/0 cells, giving mycophenolic acid—resistant clones which were screened for light chain synthesis.

Four of the top-producing subclones, secreting 4.9–7.5 μg/ml were combined into two pools (2 clones/pool) and each pool was transfected with plasmid pING42621, containing the moderate-risk heavy chain. After selection with histidinol, the clones producing the most light plus heavy chain, Sp2/0-4630 and -4621 clones C1705 and C1718, respectively, secreted antibody at approximately 15 and 22 μg/ul, respectively in the presence of $10^{-7}M$ dexamethasone in an overgrown culture in a T25 flask. Clone C1718 was deposited with the American Type Culture Collection, 1230 Parklawn Drive, Rockville, Md., 20852 on Dec. 1, 1992 as ATCC HB 11206. It is expected that limiting dilution subcloning of C1718 may produce subclones which produce humanized antibody according to the invention with as high or greater affinity for CD5 than C1718.

D. Purification Of he3 Antibody Secreted In Tissue Culture

Sp2/0-4630 (Clone C1705) and -4621 (Clone C1718) cells were grown in culture medium HB101 (Hana Biologics)+1% Fetal Bovine Serum, supplemented with 10 mM HEPES, 1x Glutamine-Pen-Strep (Irvine Scientific #9316). The spent medium was centrifuged at about 5,000×g for 20 minutes. The antibody level was measured by ELISA. Approximately 200 ml of cell culture supernatant was loaded onto a 2 ml Protein A-column (Sigma Chemicals), equilibrated with PBS (buffer 0.15M NaCl, 5 mM sodium phosphate, 1 mM potassium phosphate, buffer pH 7.2). The he3 antibody was eluted with a step pH gradient (pH 5.5, 4.5 and 2.5). A fraction containing he3 antibody (9% yield) but not bovine antibody, was neutralized with 1M Tris pH 8.5, and then concentrated 10-fold by Centricon 30 (Amicon) diluted 10-fold with PBS, reconcentrated 10-fold by Centricon 30, diluted 10-fold with PBS, and finally reconcentrated 10-fold. The antibody was stored in 0.25 ml aliquots at –20° C.

E. Competition Binding And Affinity Measurements of he3 IgG For CD5

The affinity of he3 IgG for CD5 was determined using Molt-4M cells, which express CD5 on their surface, and $^{125}$I-labeled chimeric H65 IgG in a competitive binding assay. Culture supernatants from Clone C1705 and C1718 and purified IgG from C1705 were used as the sources of he3 IgG.

For this assay, 20 μg of chimeric H65 IgG (cH65 IgG) was iodinated by exposure to 100 μl lactoperoxidase-glucose oxidase immobilized beads (Enzymobeads, BioRad), 100 μl of PBS, 1.0 mCi $I^{125}$ (Amersham, IMS30), 50 μl of 55 mM b-D-glucose for 45 minutes at 23° C. The reaction was quenched by the addition of 20 μl of 105 mM sodium metabisulfite and 120 mM potassium iodine followed by centrifugation for 1 minute to pellet the beads. $^{125}$I-cH65 IgG was purified by gel filtration using 7 mls of sephadex G25, using PBS (137 mM NaCl, 1.47 mM $KH_2PO_4$, 8.1 mM $Na_2HPO_4$, 2.68 mM KCl at pH 7.2–7.4) plus 0.1% BSA. $^{125}$I-cH65 IgG recovery and specific activity were determined by TCA precipitation.

Competitive binding was performed as follows: 100 μl of Molt-4M cells were washed two times in ice-cold DHB binding buffer (Dubellco's modified Eagle's medium (Gibco, 320-1965PJ), 1.0% BSA and 10 mM Hepes at pH 7.2.–7.4). Cells were resuspended in the same buffer, plated into 96 v-bottomed wells (Costar) at $3 \times 10^5$ cells per well and pelleted at 4° C. by centrifugation for 5 min at 1,000 rpm using a Beckman JS 4.2 rotor; 50 μl of 2X-concentrated 0.1 nM $^{125}$I-cH65 IgG in DHB was then added to each well and competed with 50 μl of 2X -concentrated cH65 IgG or humanized antibody in DHB at final antibody concentrations from 100 nM to 0.0017 nM. Humanized antibody was obtained from culture supernatants of Sp2/0 clone C1718 which expresses he3 IgG. The concentration of the antibody in the supernatants was established by ELISA using a chimeric antibody as a standard. The concentration of the antibody in the purified preparation was determined by binding was allowed to proceed at 4° C. for 5 hrs and was terminated by washing cells three times with 200 μl of DHB binding buffer by centrifugation for 5 min at 1,000 rpm. All buffers and operations were at 4° C. Radioactivity was determined by solubilizing cells in 100 μl of 1.0M NaOH and counting in a Cobra II auto gamma counter (Packard). Data from binding experiments were analyzed by the weighted nonlinear least squares curve fitting program, MacLigand, a Macintosh version of the computer program "Ligand" from Munson, Analyt. Biochem., 107:220 (1980). Objective statistical criteria (F, test, extra sum squares principle) were used to evaluate goodness of fit and for discriminating between models. Nonspecific binding was treated as a parameter subject to error and was fitted simultaneously with other parameters.

Figure 11:
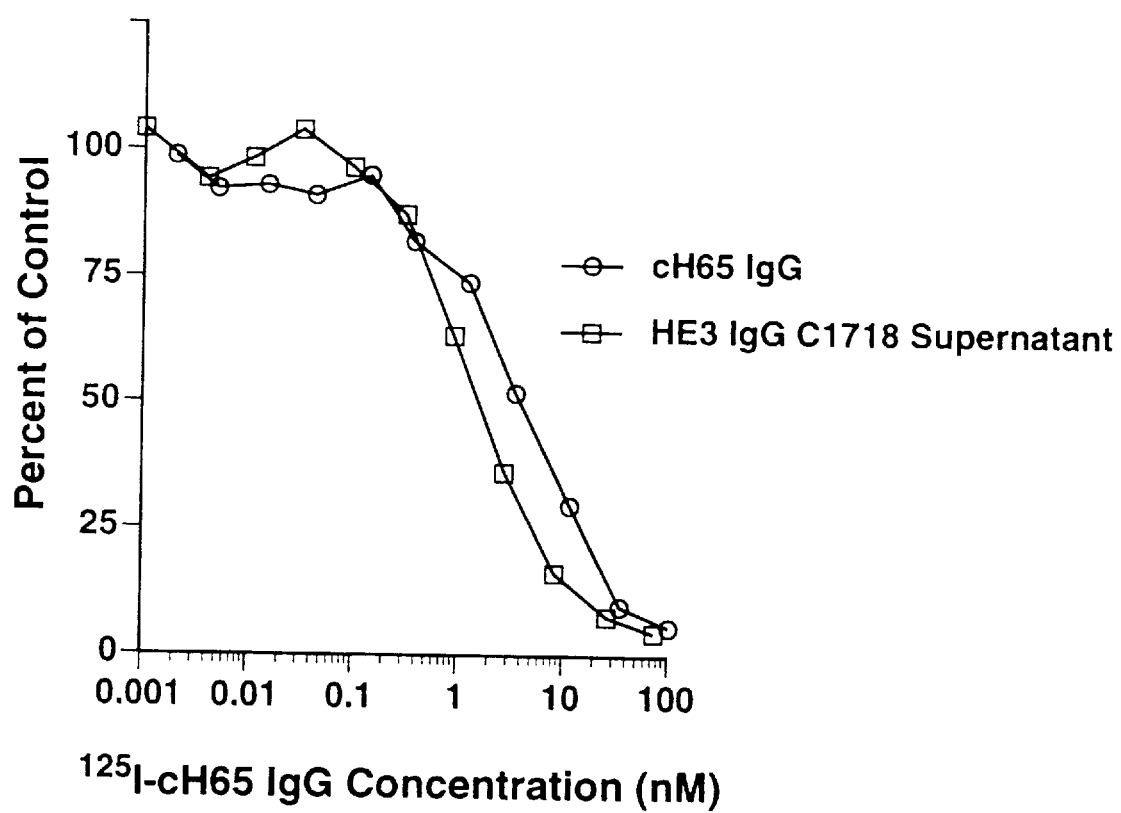
FIG. 11 is a graph of he3 IgG and he3 Fab binding to CD5 found on Molt-4M cells, demonstrating that such binding is improved over that of cH65 IgG and cH65 Fab.

Relative binding of he3 and cH65 to CD5 on Molt-4M cells in a competition binding assay are shown in Table 10 and in FIG. 11. These results demonstrate that the moderate-risk changes made in he3 IgG result in an antibody with a higher affinity than the chimeric mouse-human form of this antibody (cH65) for its target, CD5. In this particular case, moderate risk changes appear to increase affinity slightly, but a decrease may be expected in some cases.

|  | Chimeric | Low-Risk | Moderate-Risk |
|---|---|---|---|
| $F_{ab}$ | 18.4 ± 8.3 nM | 14.3 ± 0.7 nM | 2.2 ± 0.7 nM |
| IgG | 2.3 ± 1.0 nM | 2.1 ± 0.5 nM | 0.7 ± 0.4 nM |

Example 10

Antibodies May Be Further Modified Toward Human

If it is desirable to humanize an antibody variable domain beyond the changes identified above, further, higher-risk changes may be made to evolve the domain.

Higher-risk residues may be changed in a round of mutagenesis subsequent to the moderate risk changes, in smaller groups, so that deleterious mutations may be identified quickly and corrected before binding activity is abolished. (Low risk changes can be made all at once, with little fear of abolishing activity.)

For example, because in the three-dimensional model of each subunit, framework 1 and framework 3 (F1 and F3 in FIGS. 2 and 3) form semi-independent loops on the surface of the subunit, the moderate or high risk mutations may therefore be divided into four groups (consisting of F1 and F3 in the light subunit and F1 and F3 in the heavy subunit).

Four different constructs may be made, each containing higher-risk "human" mutations in only one framework region with the other three frameworks left completely "mouse," and assayed for activity. This technique avoids the dilemma raised by other humanization methods in which all higher-risk changes are made at once, making it difficult to determine which of the many amino acid changes is responsible for affecting antigen-binding activity. The creation of antibodies according to the invention which possess moderate risk changes are described below.

Example 11

Preparation Of he3 Fab

The sections below detail the construction of human-engineered he3 Fab.

A. he3-Fab Expression Plasmids

The he3 heavy chain V-region was PCR-amplified from plasmid pING4621 (pING4621 is described above in Example 9A above), with primers H65-G3, GAGATC-CAGTTGGTGCAGTCTG (SEQ ID NO: 55) and H65G2. Amplification was carried at using vent polymerase (New England Biolabs) for 25 cycles, including a 94° C. denaturation for 1 minute, annealing at 50° C. for 2 minutes, and polymerization for 3 minutes at 72° C. The PCR product was treated with polynucleotide kinase and digested with BstEII and the V-region DNA was purified. The purified DNA fragment was then ligated into pIC100, which had been digested with SstI, treated with T4 polymerase, and cut with BstEII. The resulting fragment was then ligated with the BstEII fragment from pING3218 (containing Fab' genes) to make pING4623 which contained the he3 Fd gene linked to the pelB leader sequence.

The he3 kappa V-region was next assembled using six oligonucleotide primers, $H65k-1, AGT CGT CGA CAC GAT GGA CAT GAG GAC CCC TGC TCA GTT TCT TGG CAT CCT CCT ACT CTG GTT TCC AGG TAT CAA ATG TGA CAT CCA GAT GAC TCA GT (SEQ ID NO: 30);

HUH-K6, TCA CTT GCC GGG CGA ATC AGG ACA TTA ATA GCT ATT TAA GCT GGT TCC AGC AGA AAC CAG GGA AAG CTC CTA AGA CCC T (SEQ ID NO: 49);

HUH-K7, TGA CTC GCC CGG CAA GTG ATA GTG ACT CTG TCT CCT ACA GAT GCA GAC AGG GAA GAT GGA GAC TGA GTC ATC TGG ATG TC (SEQ ID NO: 51);

HUH-K8, GAT CCA CTG CCA CTG AAC CTT GAT GGG ACC CCA GAT TCC AAT CTG TTT GCA CGA TAG ATC AGG GTC TTA GGA GCT TTC C (SEQ ID NO: 53);

HUH-K4, GGT TCA GTG GCA GTG GAT CTG GGA CAG ATT ATA CTC TCA CCA TCA GCA GCC TGC AAT ATG AAG ATT TTG GAA TTT ATT ATT G (SEQ ID NO: 34); and HUH-K5, GTT TGA TTT CAA GCT TGG TGC CTC CAC CGA ACG TCC ACG GAG ACT CAT CAT ACT GTT GAC AAT AAT AAA TTC CAA AAT CTT C (SEQ ID NO: 35)

and amplified with primers HUK-7 (SEQ ID NO: 66) and JK1-HindIII (SEQ ID NO: 45).

The resulting PCR product was treated with T4 polymerase, digested with HindIII, and purified. The purified fragment was then cloned into pIC100, which had first been cut with SstI, treated with T4 polymerase, and digested with XhoI, along with the 353 bp HindIII-XhoI fragment encoding the kappa constant region from pING3217. The resulting plasmid was pING4627 which contains the he3 kappa sequence linked in frame to the pelB leader.

Plasmid pING4628, containing the pelB-linked he3 kappa and Fd genes under transcriptional control of the araB promoter, was assembled from pING4623 and pING4627 as follows.

An expression vector for unrelated kappa and Fd genes, pNRX-2, was first cut with SauI and EcoRI, leaving a vector fragment which contains all the features relevant to plasmid replication, a tetracycline resistance marker, araB transcriptional control, and the 3' end of the Fd constant region. [Plasmid pNRX-2 comprises an EcoRI to XhoI DNA segment from pING3104 (described in WO 90/02569, incorporated by reference herein). That segment contains the replication, resistance and transcription control features of pING3104 and is joined to an XhoI to SauI DNA segment from pING1444 (Described in WO 89/00999, incorporated by reference herein) which contains the 3' end of an Fd constant region. Next pING4623 was cut with PstI, treated with T4 polymerase, digested with SauI and the pelB::Fd gene segment was then isolated. Plasmid pING4627 was cut with XhoI, treated with T4 polymerase, cut with EcoRI and ligated to the pelB::Fd gene segment and the pNRX-2 vector fragment to generate the he3-Fab expression vector pING4628. That plasmid contains two XhoI sites, one located between the kappa and Fd genes, and another 4 bp downstream of the termination codon for the Fd gene.

A vector, pING4633, which lacks the XhoI site between the kappa and Fd genes was constructed. To assemble pING4633, pING4623 was cut with EcoRI, treated with T4 polymerase, digested with SauI. The pelB::kappa gene segment was then isolated and purified. The pNRX-2 vector fragment and the pelB::Fd gene segment were then ligated to the purified pelB::kappa gene segment to form pING4633.

Both pING4633 and pING4628 are bacterial expression vectors for he3-Fab and each comprises the he3 Fd and Kappa genes which are expressed as a dicistronic message upon induction of the host cell with L-arabinose. Moreover, pING4628 contains two XhoI restriction sites, one located 4bp past the Fd termination codon and one in the intergenic region between the 3' end of the Kappa gene and the 5' end of the Fd gene. Plasmid pING4633 lacks the XhoI site in the intergenic region.

B. Purification Of he3Fab

Plasmids pING4628 was transformed into *E. coli* E104. A bacterial culture of pING4628 wasinduced with arabinose and cell-free supernatant comprising the he3Fab was concentrated and filtered into 20 mm HEPES, pH 6.8. The sample was then loaded onto a CM Spheradex column (2.5×3 cm), equilibrated in 20 mM HEPEs, 1.5 mM NaCl, pH 6.8. The column was washed with the same buffer and eluted with 20 mm HEPES, 27 mM NaCl, pH 6.8. The eluate was split into 2 aliquots and each was loaded onto and eluted from a protein G (Bioprocessing) column (2.5×2.5 cm) separately. The protein G column was equilibrated in 20 mM HEPES, 75 MM NaCl, pH 6.8 and the sample was eluted with 100 mM glycine, 100 mM NaCl, pH 3.0. The two eluates were combined and diluted two times with 20 mM HEPES, 3M ammonium sulfate, pH 6.8. The diluted eluates were loaded onto phenyl sepharose high substitution Fast Flow (Pharmacia) column (2.5×3.3 cm), equilibrated n 20 mM HEPES, 1.5M ammonium sulfate, pH 6.8. The column was then eluted with 20 mM HEPES, 0.6M ammonium sulfate, pH 6.8. Plasmid pING4633, also containing he3 Fab may be prepared and purified in a manner identical to pING4628.

The purified he3 Fab was tested for binding affinity as described for human-engineered IgG by the methods described in Example 7. The results of this experiment are shown in FIG. 11. FIG. 11 also shows results obtained with low-risk he1 Fab which was prepared by procedures similar to those used to prepare he3 Fab.

C. he3 F(ab')$_2$ Expression Plasmids

An expression vector for Fab' with the Fd' (2c) 3'-end (Better, et al., *Proc. Natl. Acad. Sci. USA*, 90:457–461 (1993), and references cited therein) was assembled as described above from pING4623 and pING4627. In this case, the PstI cut, T4 polymerase treated and SauI digested gene segment from pING4623 and the XhoI cut, T4 polymerase treated, and EcoRI digested gene segment from pING4627 were ligated into pING3197 previously digested with EcoRI and SauI. The vector portion of pING3197 is identical to pNRX2, described above, but contains the Fd' (2C) module rather than the Fd module (see Better, et al.). The resulting expression vector from which he3 F(ab')$_2$ may be produced is designated pING4629. Host cells containing pING4629 were deposited with the American Type Culture Collection, 10801 University Boulevard, Manassas, Va. 20110-2209 on Jun. 16, 1993 as ATCC Accession No. G284

Example 12 he3 Single Chain Antibody And Gelonin-Single Chain Antibody Fusions

A single chain form of the human engineered he3 antibody was expressed, as were single chain antibody fusions to a natural sequence gelonin toxin gene. The gelonin gene, described in co-owned, co-pending U.S. patent application Ser. No. 08/064,691, incorporated by reference herein, was positioned at either the N-terminus or the C-terminus of the fusion gene and a Shiga-Like Toxin (hereinafter referred to as "SLT") or a Rabbit Muscle Aldolase (hereinafter referred to as "RMA") linker peptide was positioned between the gelonin and antibody domains to allow intracellular processing of the fusion protein with subsequent cytosolic release of gelonin. Uses for single chain he3—gelonin fusion proteins are disclosed in co-owned, co-pending U.S. patent application Ser. No. 08/064,691, incorporated by reference herein.

A. Construction of Gel::RMA::SCA($V_L$-$V_H$), Gel::SLT::SCA ($V_L$-$V_H$), Gel::RMA::SCA($V_H$-$V_L$), and Gel::SLT::SCA ($V_H$-$V_L$)

A single chain antibody (SCA) form of the he3 H65 variable domain was assembled from previously constructed genes. This SCA segment consisted of the entire V and J region of the one chain (heavy or light) linked to the entire V and J segment of the other chain (heavy or light) via a 15 amino acid flexible peptide: [(Gly)$_4$ Ser]$_3$. This peptide is identical to that described in Huston et al., *Proc. Natl. Acad. Sci. USA*, 85:5879–5883 (1988); Glockshuber et al., *Biochemistry*, 29:1362–1367 (1990); and Cheadle et al., *Molecular Immunol.*, 29:21–30 (1992). The SCA was assembled in two orientations: V-J$_{kappa}$:: [(Gly)$_4$Ser]$_3$::V-J$_{Gamma}$ and V-J$_{Gamma}$:: [(Gly)$_4$Ser] $_3$: :V-J$_{kappa}$. Each SCA segment was assembled and subsequently fused to gelonin.

For assembly of the SCA segment V-J$_{kappa}$:: [(Gly)$_4$Ser] $_3$:: V-J$_{Gamma}$, primers HUK-7 and SCFV-1 were used to amplify a 352 bp DNA fragment containing the he3 V/J kappa sequences from pING4627 by PCR in a reaction containing 10 mM KCl, 20 mM TRIS pH 8.8, 10 mM ($NH_4$)$_2SO_2$, 2 mM $MgSO_4$, 0.1% Triton X-100., 100 ng/ml BSA, 200 uM of each dNTP, and 2 Units of Vent polymerase (New England Biolabs, Beverley, Mass.) in a total volume of 100 μl.

SCFV-1 (SEQ ID NO: 65)
  5' CGGACCCACCTCCACCAGATCCACCGC CAC-CTTTCATCTCAAGCTTGGTGC 3'
HUK-7 (SEQ ID NO: 66)
  5' GACATCCAGATGACTCAGT 3'

Concurrently, primers SCFV-2 and SCFV-3 were used to amplify a he3 heavy chain V/J gamma segment from pING4623, generating a 400 bp fragment.

SCFV-2 (SEQ ID NO: 67)
  5' GGTGGAGGTGGGTCCGGAGGTGGAG-GATCTGA GATCCAGTTGGTGCAGT 3'
SCFV-3 (SEQ ID NO: 68)
  5' TGTACTCGAGCCCATCATGAGGAGACG-GTGACCGT 3'

The products from these reactions were mixed and amplified with the outside primers HUK-7 and SCFV-3. The product of this reaction was treated with T4 polymerase and then cut with XhoI. The resulting 728 bp fragment was then purified by electrophoresis on an agarose gel. This fragment was ligated into the vectors pING3755 and pING3748 [pING3748 contains a gene encoding gelonin toxin linked in frame to DNA encoding a Shiga-like toxin linker and pING3755 contains DNA encoding gelonin toxin linked in frame to a Rabbit muscle aldolase linker. Both pING3748 and 3755 are described in co-owned, co-pending U.S. patent application Ser. No. 08/064,691] each digested with ScaI and XhoI. The resulting vectors pING4637 and pING4412 contain the Gelonin::RMA::SCA V-$J_{kappa}$:: [(Gly)$_4$Ser]$_3$::V-$J_{Gamma}$ and Gelonin::SLT::SCA V-$J_{kappa}$:: [(Gly)$_4$Ser]$_3$::V-$J_{Gamma}$ fusion genes, respectively. The 728 bp fragment was also ligated into pIC100 previously digested with SstI, treated with T4 polymerase and digested with XhoI, to generate pING4635. This plasmid contains the pelB leader sequence linked in-frame to the V-$J_{kappa}$:: [(Gly)$_4$Ser]$_3$:: V-$J_{gamma}$:: The pelB::SCA gene in pING4635 was excised as an EcoRI-XhoI restriction fragment and cloned into the bacterial expression vector to generate pING4640.

Similarly, the SCA V-$J_{Gamma}$:: [(Gly)$_4$Ser]$_3$:: V-$J_{kappa}$ was assembled by amplification of pING4627 with primers SCFV-5 and SCFV-6 generating a 367 bp fragment containing he3 V/J kappa sequences, SCFV-5 (SEQ ID NO: 69)
  5' GGTGGAGGTGGGTCCGGAGGTGGAGGATCT GACATCCAGATGACTCAGT 3'
SCFV-6 (SEQ ID NO: 70)
  5' TGTACTCGAGCCCATCATTTCATCT-CAAGCTTGGTGC 3' and pING4623 with primers H65-G3 and SCFV-4 generating a 385 bp fragment containing he3 gamma V/J sequences by PCR with Vent polymerase.

H65-G3 (SEQ ID NO: 71)
  5' GAGATCCAGTTGGTGCAGTCTG 3'
SCFV-4 (SEQ ID NO: 72)
  5' CGGACCCACCTCCACCAGATCC ACCGCCAC-CTGAGGAGACGGTGACCGT 3'

The products from these reactions were mixed and amplified with H65-G3 and SCFV-6. The 737 bp product was treated with T4 polymerase and cut with XhoI. Ligation into pING3755 and pING3748 (digested with ScaI and XhoI) resulted in assembly of the Gelonin::RMA::SCA V-$J_{Gamma}$:: [(Gly)$_4$Ser]$_3$::V-$J_{kappa}$ gene fusion in pING4638 and Gelonin::SLT::SCA V-$J_{Gamma}$:: [(Gly)$_4$Ser]$_3$::V-$J_{kappa}$ gene fusion in pING4639, respectively. An expression plasmid for SCA V-$J_{gamma}$:: [(Gly)$_4$Ser]$_3$: :V-$J_{kappa}$ was assembled from DNA segments in pING4623 and pING4638. The 459 bp fragment released from pING4623 by digestion with EcoRI and BstEII was ligated along with the 384 bp fragment released from pING4638 by digestion with BstEII and XhoI into the bacterial expression vector to generate pING4636.

The vectors pING4637, pING4412, pING4638 and pING4639 were each transformed into E. coli strain E104 and induced with arabinose. Protein products of the predicted molecular weight were identified by Western blot with gelonin-specific antibodies.

B. Construction of SCA($V_L$-$V_H$)::SLT::Gelonin Vectors

The expression vector containing SCA($V_L$-$V_H$) ::SLT::Gelonin fusions was assembled using restriction fragments from previously-constructed plasmids pING4640 (containing SCA($V_L$-$V_H$)) pING4407 (containing Kappa::SLT::Gelonin, Fd), and pING3197. Plasmid pING4640 was first cut with BspHI, filled in with T4 polymerase in the presence of only dCTP, treated with mung bean nuclease (MBN) to remove the overhang and to generate a blunt end, and cut with EcoRI. The resulting 849 bp fragment was purified. The SLT-containing fragment from pING4407 was excised by cutting with EagI, blunted with T4 polymerase, cut with XhoI, and the approximately 850 bp fragment which resulted was purified. The two fragments were ligated together into pING3197, which had been treated with EcoRI and XhoI to generate pING4642. The DNA sequence at the BspHI-T4-MBN/EagI junction revealed that two of the expected codons were missing but that the fusion protein was in frame.

C. Construction of SCA($V_H$-$V_L$)::SLT::Gelonin Vectors

The expression vector containing the SCA($V_H$-$V_L$) ::SLT::Gelonin fusions was assembled using DNA from plasmids pING4636, (the E. coli expression vector for SCA($V_H$-$V_L$)) and pING4407. Plasmid pING4636 was cut with BstEII and XhoI and the resulting vector fragment was purified. Concurrently, pING4636 was used as a template for PCR with primers SCFV-7, 5'TGATGCGGCCGACATCT-CAAGCTTGGTGC (SEQ ID NO: 77) and H65-G13, TGATGCGGCCGACATCTCAAGCTTGGTGC3' (SEQ ID NO: 78). The amplified product was digested with EagI and BstEII and the resulting approximately 380 bp fragment was purified. Plasmid pING4407 was then cut with EagI and XhoI, resulting in an approximately 850 bp fragment, which was purified. The three above fragments were ligated together to produce pING4643.

D. Construction of SCA($V_L$-$V_H$)::RMA::Gelonin Vectors

Expression vectors containing SCA($V_L$-$V_H$) ::RMA::Gelonin fusions were assembled using DNA from pING4640, pING4408, and pING3825. Plasmid pING4640 was cut with SalI and BstEII and the resulting approximately 700 bp vector fragment (containing the tetracycline resistance matter) was purified. Next, pING3825 was digested with NcoI and SalI, resulting in an approximately 1344 bp fragment containing the 3' end of the gelonin gene and adjacent vector sequences. That fragment was purified. Plasmid pING4408 was then PCR amplified with oligonucleotide primers, RMA-G3 5'TCTAGGTCACCGTCTC-CTCACCATCTGGACAGGCTGGA3' (SEQ ID NO: 79), and gelo-10. The resulting PCR product was cut with BstEII and NcoI to generate an approximately 180 bp fragment containing the 3' end of VH, RMA, and the 5' end of the Gelonin gene which was purified. The above three fragments were ligated to generate the final expression vector, pING4644. Host cells transformed with pING4644 were deposited with the American Type Culture Collection, 10801 University Boulevard, Manassas, Va. 20110-2209 on Jun. 16, 1993 as ATCC Accession No. 69332.

E. Construction of SCA($V_H$-$V_L$)::RMA::Gelonin Vectors

Expression vectors containing SCA($V_H$-$V_L$) ::RMA::Gelonin were constructed using DNA from pING4636, pING4410, and pING3825. Plasmid pING4636 was digested with SalI and HindIII and the resulting vector fragment was purified. Next, pING3825 was cut with NcoI and SalI and the 1344 bp fragment which resulted contained the 3' end of the gelonin gene and adjacent vector sequences encoding tetracycline resistance was purified. Finally, pING4410 was PCR amplified with primers RMA-G4, 5'TTCGAAGCTTGAGATGAAACCATCTGGA-CAGGCTGGA3' (SEQ ID NO: 80) and gelo-10. The PCR product was cut with HindIII and NcoI, resulting in a 180 bp fragment containing the 3'end of $V_L$, RMA, and the 5' end of Gelonin and was purified. The three above fragments were ligated together to generate the final expression vector, pING4645.

Gelonin::SCA fusions without a cleavable linker may be constructed by deletion of the SLT linker in pING4412 using the restriction enzymes EagI and FspI. Digestion at these sites and religation of the plasmid results in an in-frame deletion of the SLT sequence.

F. Construction Of he3 SCA Versions with A Poly-Histidine Tail

Six histidine residues were added on to the carboxyl terminus of the SCA genes (both VL-VH and VH-VL) by PCR mutagenesis. The mutagenic oligonucleotides SCA-his1, 5'-TGTACTCGAGCCCACTAGTCATGGTGGTGATGGTGTTTCATCTCAA GCTTGGTGC-3' (SEQ ID NO: 81) and SCA-his2, 5'-TGTACTCGAGCCCACTAGTGATGGTG GTGATGGTGTGAGGAGACGGTGACCGT-3' (SEQ ID NO: 82) were used along with HuK-7 (SEQ ID NO: 66) and H65-G3 (SEQ ID NO: 71). For the VL-VH-his6 clone, pING4640 was amplified with Huk-7 and SCA-His2. The resultant approximately 760 bp fragment was cut with BstEll and XhoI, and the approximately 50 bp fragment was purified. This was cloned into pING4640 that had been cut with BstEll and XhoI. The new product may be distinguished from pING4640 by an SpeI site introduced in SCA-his2. The DNA sequence of the new plasmid, pING3336, was verified. Host cells transformed with pING3336 were deposited with the American Type Culture Collection, 10801 University Boulevard, Manassas, Va. 20110-2209 on Jun. 16, 1993 as ATCC Accession No. 69331.

For the VH-VL-his6 clone, pING4636 was amplified with H65-G3 and SCA-hisl. The approximately 760 bp fragment was cut with BstEll and XhoI and the approximately 420 bp fragment was purified. This was cloned into pING4636 cut with BstEll and XhoI. Again the new product could be distinguished from pING4636 by an SpeI site introduced in SCA-his1. The DNA sequence of the new plasmid, pING3337, was verified.

Example 13

Affinity Of Single Chain Antibodies And Antibody Fusions

A. Competitive Binding Of Single Chain Antibodies And Fusion Proteins To Molt-4M Cells Molt-4M cells were used to determine the competitive binding characteristics of single chain humanized antibodies. The competitive binding assay involved the incubation of $3\times10^5$ Molt-4M cells in the presence of 0.1 nm $^{125}$I-cH65 and from 0.005 nM to 100 nM cH65 IgG or single chain antibody for 5 hours at 4° C. The cells were incubated in 96 v-well plates which were centrifuged 1000 g for 5 min. at 4° C. prior to the removal of medium and addition of the ligands. The results are shown in FIG. 17. In that experiment using CD5-expressing Molt-4M cells, the single chain antibodies (curves H and I) had slightly less affinity than did he3 Fab (curve B).

B. Competitive Binding Of Single Chain Antibodies To Soluble CD5

In a second experiment, recombinant soluble CD5 was used to again determine the competitive binding characteristics of single chain humanized antibodies. Recombinant soluble CD5 was prepared and bound to a microtiter plates according to commonly-known methods, such as those disclosed in Harlow et al., Eds., *Antibodies: A Laboratory Manual*, Cold Spring Harbor Laboratory, Cold Spring Harbor (1988). The assays were conducted as described in the preceding paragraph. Recombinant CD5 may be isolated as described in Jones, et al., *Nature,* 323:346–349 (1986), incorporated by reference herein, and expression of CD5 cDNA is reported in Mishimura, et al., *Eur. J. Immunol.,* 18:747–753 (1988), incorporated by reference herein. The results of the competition assay using soluble CD5 demonstrate that single chain antibodies have an affinity similar to that of he3 Fab (FIG. 18).

Example 14

Evidence Of Therapeutic Utility Of Modified Antibodies

As a demonstration of the therapeutic utility of he3 antibodies, a study was conducted to compare the potency of he3 Fab, chimeric H65 Fab, and H65 conjugates in killing lectin-activated T-lymphocytes from human peripheral blood mononuclear cells. A procedure for such assays is described in Fishwild et al., *Clin. Exp. Immunol.,* 86:506–513 (1991). CD5 Plus™, a murine H65 antibody linked to ricin toxin A using N-succinimydyl-3-(2-pyridylthio) propionate according to the procedure described in Byers et al., *Blood,* 75:1426–1432 (1990), was compared to chimeric H65 (chimeric H65) Fab and he3 Fab conjugates linked to Ricin Toxin A chain (RTA) using 5-methyl-2-iminothiolane, as described in Better et al., *Proc. Nat. Acad. Sci.* (USA), 90:457–461 (1993). The results are presented in Table 10.

TABLE 10

COMPARISON OF he3 AND H65: CYTOTOXICITY RESULTS

| | DONOR # | | | | | | |
|---|---|---|---|---|---|---|---|
| | #1 | #2 | #3 | #4 | #5 | Mean | SD |
| IC50 (pM TOXIN) (PL 0.0431) | | | | | | | |
| CD5 Plus | 209 | 847 | 6120 | >9520 | 1260 | 2,109 | 2,709 |
| cH65Fab-m-RTA30 | 837 | 684 | 1030 | 3090 | 2290 | 1,586 | 1,054 |
| he3Fab-m-RTA30 | 280 | 391 | 425 | 326 | 294 | 343 | 63 |
| % KILL AT HIGHEST CONCENTRATION (PL 0.0422) | | | | | | | |
| CD5 Plus | 74.3 | 58.2 | 53.4 | 47.1 | 60.3 | 58.7 | 10.1 |
| cH65Fab-m-RTA30 | 89.3 | 94.2 | 94.4 | 78.5 | 92.0 | 89.7 | 6.6 |
| he3Fab-m-RTA30 | 90.0 | 95.1 | 95.3 | 87.9 | 95.6 | 92.8 | 3.6 |

Example 15

Treatment Of Rheumatoid Arthritis

Patients having rheumatoid arthritis (RA) are selected for treatment using an anti-pan T cell antibody of this invention.

Anti-CD5 antibody prepared as described above is administered to patients at doses of about 0.005 to 2.0 mg/kg/day for a period of 1–5 days, preferably 1–2 days. Alternatively, the dose may be given every 2–30 days instead of daily if chimeric and humanized MoAbs are used due to their increased half-life. To determine optimum dose and schedule, patients are treated at each dose and schedule in a dose escalating regimen. Patients are monitored using several indicia, including joint swelling and tenderness scores.

Example 16

Treatment Of Systemic Lupus Erythematosus

Systemic Lupus Erythematosus ("SLE") is a multisystemic disease characterized by inflammation and autoimmunity. Some of the more frequent manifestations include fatigue, anemia, fever, rashes, photosensitivity, alopecia, arthritis, pericarditis, pleurisy, vasculitis, nephritis and central nervous system disease. Under the Revised Criteria for Classification of SLE, a person is said to have SLE for purposes of clinical studies if any four or more of the aforementioned specified criteria are present, serially or simultaneously, during any interval of observation.

Anti-CD5 antibody prepared as described above is administered to patients at doses of about 0.005 to 2.0 mg/kg/day for a period of 1–5 days, preferably 1–2 days. Alternatively, the dose may be given every 2–30 days instead of daily if chimeric and humanized MoAbs are used due to their increased half-life. To determine optimum dose and schedule, patients are treated at each dose and schedule in a dose escalating regimen.

Example 17

Treatment Of Psoriasis

Psoriasis is a disease of autoimmune etiology which Classically appears as plaques over the elbows and knees, although other areas of the skin are frequently afflicted. Abnormalities of the nails and the joints are also frequently observed. Particularly inflammatory joint disease can occur in an occasionally erosive and severe form.

Anti-CD5 antibody prepared as described above is administered to patients at doses of about 0.005 to 2.0 mg/kg/day for a period of 1–5 days, preferably 1–2 days. Alternatively, the dose may be given every 2-30 days instead of daily if chimeric and humanized MoAbs are used due to their increased half-life. To determine optimum dose and schedule, patients are treated at each dose and schedule in a dose escalating regimen.

Clinical observation includes evaluation of the patient's overall status as well as special attention to the psoriatic plaques. Additionally, monitoring of laboratory parameters such as white blood count and differential are recommended. Symptoms which may indicate poor tolerance to therapy or complications include nausea, vomiting, fatigue, rash, fever, chills and syncope. Any unexplained depletion in white blood cells other than lymphocytes is an indication to discontinue therapy. Preferably, differential analysis of lymphocytes is carried out. That is, analysis of the total number of T cells and B cells should be determined.

Example 18

Treatment Of Type I Diabetes

There are two major types of diabetes. Type I has classically been associated with a requirement for exogenous insulin. Type I typically occurs before the age of 40 and is associated with an absence of insulin secretion. The pancreas of patients with long-term Type I insulin-dependent diabetes are devoid of pancreatic islet cells. There is a large body of evidence that the etiology of Type I insulin-dependent diabetes (IDDM) is autoimmune.

Patients are diagnosed as having IDDM based on the criteria established by the American Diabetes Association. Anti-CD5 antibody prepared as described above is administered to patients at doses of about 0.005 to 2.0 mg/kg/day for a period of 1–5 days, preferably 1–2 days. Alternatively, the dose may be given every 2–30 days instead of daily if chimeric and humanized MoAbs are used due to their increased half-life. To determine optimum dose and schedule, patients are treated at each dose and schedule in a dose escalating regimen.

During the study, the patients were monitored by clinical and laboratory parameters. Clinical symptoms indicating poor tolerance to therapy or complications include fatigue, vomiting, rash, fever, chills, and syncope. Laboratory evaluation included white blood cell counts with differential analysis daily and blood glucose levels at least twice a day.

Using diagnostic criteria predictive of the onset of Type I diabetes, patients may be selected for prophylactic treatment. This treatment follows the dose and schedule noted above for treatment of clinical insulin-dependent diabetes.

We claim:

1. A protein comprising an he1 light chain variable region that comprises the amino acid sequence DIQMTQSPSSMSASLGDRVTITCRASQ-
DINSYLSWFQQKPGKSPKTLIYRANRL
VDGVPSRFSGSGSGTDYTLTISSLQYED-
FGIYYCQQYDESPWTFGGGTKLEIK (SEQ ID No 27), or fragment thereof that is capable of binding antigen when combined with a heavy chain variable region.

2. The protein of claim 1, wherein the amino acid residue at one or more moderate risk sites as shown on FIG. 6A in said light chain variable region is replaced by the amino acid residue in the corresponding position in the amino acid sequence of a selected antibody light chain variable region sequence or consensus sequence.

3. A protein comprising an he1 heavy chain variable region that comprises the amino acid sequence QIQLVQSGPGLKKPGGSVRISCAASGYTFTNYGMNWVKQAPGKGLRWMGWI NTHTGEPTYADDFKGRFTFSLDTSKSTAYLQINSLRAEDTATYFCTRRGYDWY FDVWGQGTTVTVSS (SEQ ID No 29) or fragment thereof that is capable of binding antigen when combined with a light chain variable region.

4. The protein of claim 3, wherein the amino acid residue at one or more moderate risk sites as shown on FIG. 6B in said heavy chain variable region is replaced by the amino acid residue in the corresponding position in the amino acid sequence of a selected antibody heavy chain variable region sequence or consensus sequence.

5. A protein comprising an he3 light chain variable region that comprises the amino acid sequence:

DIQMTQSPS SLSASVGDRVTITCRASQDINSYLSWFQQKPGKAPKTLIYRANRL ESGVPSRFSGSGSGTDYTLTIS SLQYEDFGIYYCQQYDESPWTFGGGTKLEIK (SEQ ID No 87) or fragment thereof that is capable of binding antigen when combined with a heavy chain variable region.

6. A protein comprising an he3 heavy chain variable region that comprises the amino acid sequence:

EIQLVQSGGGLVKPGGSVRISCAASGYTFTNYGMNWVRQAPGKGLEWMGWI NTHYGEPTYADSFKGTRTFSLDDSKNTAYLQINSLRAEDTAVYFCTRRGYDW YFDVWGQGGTTVTVSS (SEQ ID No 88) or fragment thereof that is capable of binding antigen when combined with a light chain variable region.

7. A protein comprising (1) an he1 light chain variable region that comprises the amino acid sequence:

DIQMTQSPSSMSASLGDRVTITCRASQDINSYLSWFQQKPGKSPKTLIYRANRL VDGVPSRFSGSGSGTDYTLTIS SLQYEDFGIYYCQQYDESPWTFGGGTKLEIK (SEQ ID No 27), and (2) an he1 heavy chain variable region that comprises the amino acid sequence:

QIQLVQSGPGLKKPGGSVRISCAASGYTFTNYGMNWVKQAPGKGLRWMGWI NTHTGEPTYADDFKGRFTFSLDTSKSTAYLQINSLRAEDTATYFCTRRGYDWY FDVWGQGTTVTVSS (SEQ ID No 29)

or fragment of said protein that is capable of binding antigen.

8. The protein of claim 7, wherein one or more amino acids that are at moderate risk sites as shown in FIG. 6A in said light chain variable region is replaced by the amino acid residue in the corresponding position in the amino acid sequence of a selected antibody light chain variable region sequence or consensus sequence, or one or more amino acids that are at moderate risk sites as shown in FIG. 6B in said heavy chain variable region is replaced by the amino acid residue in the corresponding position in the amino acid sequence of a selected antibody heavy chain variable region sequence or consensus sequence, or both.

9. A protein comprising an he3 light chain variable region that comprises the amino acid sequence:

DIQMTQSPSSLSASVGDRVTITCRASQDINSYLSWFQQKPGKAPKTLIYRANRL ESGVPSRFSGSGSGTDYTLTISSLQYEDFGIYYCQQYDESPWTFGGGTKLEIK (SEQ ID No 87), and (2) an he3 heavy chain variable region that comprises the amino acid sequence:

EIQLVQSGGGLVKPGGSVRISCAASGYTFTNYGMNWVRQAPGKGLEWMGWI NTHYGEPTYADSFKGTRTFSLDDSKNTAYLQINSLRAEDTAVYFCTRRGYDW YFDVWGQGGTTVTVSS (SEQ ID No 88)

or fragment of said protein that is capable of binding antigen.

10. The protein of any one of claims 1–9, wherein said protein is a F(ab)'$_2$.

11. The protein of any one of claims 1–9, wherein said protein is a Fab.

12. The protein of any one of claims 1–9, wherein said protein is a Fab'.

13. The protein of any one of claims 1–9, wherein said protein is a single chain antibody.

14. The protein of any one of claims 1–9, wherein said protein is Fv.

15. A composition comprising the protein of any one of claims and 1–9 and i) a detectable label or ii) a pharmaceutically acceptable carrier stabilizer buffer or excipient.

16. The protein of any one of claims 1–9, wherein said protein is a fusion protein.

17. A composition comprising the protein of claim 16 and i) a detectable label or ii) a pharmaceutically acceptable carrier stabilizer buffer or excipient.

* * * * *

SEQUENCE LISTING ( 1 ) GENERAL INFORMATION:

( i i i ) NUMBER OF SEQUENCES: 89

( 2 ) INFORMATION FOR SEQ ID NO:1:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Asp Ile Val Leu Thr Gln Ser Pro Ala Thr Leu Ser Val Thr Pro Gly
  1               5                  10                  15
Asn Ser Val Ser Leu Ser Cys Arg Ala Ser Gln Ser Ile Gly Asn Asn
             20                  25                  30
Leu His Trp Tyr Gln Gln Lys Ser His Glu Ser Pro Arg Leu Leu Ile
         35                  40                  45
Lys Tyr Ala Ser Gln Ser Ile Ser Gly Ile Pro Ser Arg Phe Ser Gly
     50                  55                  60
Ser Gly Ser Gly Thr Asp Phe Thr Leu Ser Ile Asn Ser Val Glu Thr
 65                  70                  75                  80
Glu Asp Phe Gly Met Tyr Phe Cys Gln Gln Ser Asn Ser Trp Pro Tyr
                 85                  90                  95
Thr Phe Gly Gly Gly Thr Lys Leu Asp Ile Lys
                100                 105
```

( 2 ) INFORMATION FOR SEQ ID NO:2:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asp Ile Val Met Thr Gln Ser Pro Ser Ser Leu Ser Val Ser Ala Gly
  1               5                  10                  15
Glu Arg Val Thr Met Ser Cys Lys Ser Ser Gln Ser Leu Leu Asn Ser
             20                  25                  30
Gly Asn Gln Lys Asn Phe Leu Ala Trp Tyr Gln Gln Lys Pro Gly Gln
         35                  40                  45
Pro Pro Lys Leu Leu Ile Tyr Gly Ala Ser Thr Arg Glu Ser Gly Val
     50                  55                  60
Pro Asp Arg Phe Thr Gly Ser Gly Ser Gly Thr Asp Phe Thr Leu Thr
 65                  70                  75                  80
Ile Ser Ser Val Gln Ala Glu Asp Leu Ala Val Tyr Tyr Cys Gln Asn
                 85                  90                  95
Asp His Ser Tyr Pro Leu Thr Phe Gly Ala Gly Thr Lys Leu Glu Ile
                100                 105                 110
Lys
```

( 2 ) INFORMATION FOR SEQ ID NO:3:

( i ) SEQUENCE CHARACTERISTICS:
    ( A ) LENGTH: 103 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

```
Xaa  Ser  Val  Leu  Thr  Gln  Pro  Pro  Ser  Val  Ser  Gly  Ala  Pro  Gly  Gln
 1                   5                        10                       15

Arg  Val  Thr  Ile  Ser  Cys  Thr  Gly  Ser  Ser  Asn  Ile  Gly  Ala  Gly
                20                  25                       30

Asn  His  Val  Lys  Trp  Tyr  Gln  Gln  Leu  Pro  Gly  Thr  Ala  Pro  Lys  Leu
           35                       40                       45

Leu  Ile  Phe  His  Asn  Asn  Ala  Arg  Phe  Ser  Val  Ser  Lys  Ser  Gly  Ser
          50                       55                       60

Ser  Ala  Thr  Leu  Ala  Ile  Thr  Gly  Leu  Gln  Ala  Glu  Asp  Glu  Ala  Asp
 65                       70                       75                       80

Tyr  Tyr  Cys  Gln  Ser  Tyr  Asp  Arg  Ser  Leu  Arg  Val  Phe  Gly  Gly  Gly
                85                       90                       95

Thr  Lys  Leu  Thr  Val  Leu  Arg
               100
```

( 2 ) INFORMATION FOR SEQ ID NO:4:

( i ) SEQUENCE CHARACTERISTICS:
    ( A ) LENGTH: 111 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Gln  Ser  Val  Leu  Thr  Gln  Pro  Pro  Ser  Ala  Ser  Gly  Thr  Pro  Gly  Gln
 1                   5                        10                       15

Arg  Val  Thr  Ile  Ser  Cys  Ser  Gly  Thr  Ser  Ser  Asn  Ile  Gly  Ser  Ser
                20                  25                       30

Thr  Val  Asn  Trp  Tyr  Gln  Gln  Leu  Pro  Gly  Met  Ala  Pro  Lys  Leu  Leu
           35                       40                       45

Ile  Tyr  Arg  Asp  Ala  Met  Arg  Pro  Ser  Gly  Val  Pro  Asp  Arg  Phe  Ser
          50                       55                       60

Gly  Ser  Lys  Ser  Gly  Ala  Ser  Ala  Ser  Leu  Ala  Ile  Gly  Gly  Leu  Gln
 65                       70                       75                       80

Ser  Glu  Asp  Glu  Thr  Asp  Tyr  Tyr  Cys  Ala  Ala  Trp  Asp  Val  Ser  Leu
                85                       90                       95

Asn  Ala  Tyr  Val  Phe  Gly  Thr  Gly  Thr  Lys  Val  Thr  Val  Leu  Gly
               100                      105                      110
```

( 2 ) INFORMATION FOR SEQ ID NO:5:

( i ) SEQUENCE CHARACTERISTICS:
    ( A ) LENGTH: 113 amino acids
    ( B ) TYPE: amino acid
    ( D ) TOPOLOGY: linear ( i i ) MOLECULE TYPE: protein ( x i ) SEQUENCE DESCRIPTION: SEQ ID NO:5:

```
Asp  Val  Gln  Leu  Gln  Glu  Ser  Gly  Pro  Ser  Leu  Val  Lys  Pro  Ser  Gln
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Thr | Leu | Ser | Leu<br>20 | Thr | Cys | Ser | Val | Thr<br>25 | Gly | Asp | Ser | Ile | Thr<br>30 | Ser | Asp |
| Tyr | Trp | Ser<br>35 | Trp | Ile | Arg | Lys | Phe<br>40 | Pro | Gly | Asn | Arg | Leu<br>45 | Glu | Tyr | Met |
| Gly | Tyr | Val | Ser<br>50 | Tyr | Ser | Gly<br>55 | Ser | Thr | Tyr | Tyr | Asn<br>60 | Pro | Ser | Leu | Lys |
| Ser<br>65 | Arg | Ile | Ser | Ile | Thr<br>70 | Arg | Asp | Thr | Ser | Lys<br>75 | Asn | Gln | Tyr | Tyr | Leu<br>80 |
| Asp | Leu | Asn | Ser | Val<br>85 | Thr | Thr | Glu | Asp | Thr<br>90 | Ala | Thr | Tyr | Tyr | Cys<br>95 | Ala |
| Asn | Trp | Asp | Gly<br>100 | Asp | Tyr | Trp | Gly | Gln<br>105 | Gly | Thr | Ser | Val | Thr<br>110 | Val | Ser |
| Ala |

(2) INFORMATION FOR SEQ ID NO:6:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO:6:

| Glu<br>1 | Val | Lys | Leu | Val<br>5 | Glu | Ser | Gly | Gly | Gly<br>10 | Leu | Val | Gln | Pro | Gly<br>15 | Gly |
|---|---|---|---|---|---|---|---|---|---|---|---|---|---|---|---|
| Ser | Leu | Arg | Leu<br>20 | Ser | Cys | Ala | Thr | Ser<br>25 | Gly | Phe | Thr | Phe | Ser<br>30 | Asp | Phe |
| Tyr | Met | Glu<br>35 | Trp | Val | Arg | Gln | Pro<br>40 | Pro | Gly | Lys | Arg | Leu<br>45 | Glu | Trp | Ile |
| Ala | Ala<br>50 | Ser | Arg | Asn | Lys | Gly<br>55 | Asn | Lys | Tyr | Thr | Thr<br>60 | Glu | Tyr | Ser | Ala |
| Ser<br>65 | Val | Lys | Gly | Arg | Phe<br>70 | Ile | Val | Ser | Arg | Asp<br>75 | Thr | Ser | Gln | Ser | Ile<br>80 |
| Leu | Tyr | Leu | Gln | Met<br>85 | Asn | Ala | Leu | Arg | Ala<br>90 | Glu | Asp | Thr | Ala | Ile<br>95 | Tyr |
| Tyr | Cys | Ala | Arg<br>100 | Asn | Tyr | Tyr | Gly | Ser<br>105 | Thr | Trp | Tyr | Phe | Asp<br>110 | Val | Trp |
| Gly | Ala | Gly | Thr<br>115 | Thr | Val | Thr | Val<br>120 | Ser | Ser |

(2) INFORMATION FOR SEQ ID NO:7:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:7:

| Gln<br>1 | Val | Gln | Leu | Glu<br>5 | Gln | Ser | Gly | Pro | Gly<br>10 | Leu | Val | Arg | Pro | Ser<br>15 | Gln |
|---|---|---|---|---|---|---|---|---|---|---|---|---|---|---|---|
| Thr | Leu | Ser | Leu<br>20 | Thr | Cys | Thr | Val | Ser<br>25 | Gly | Thr | Ser | Phe | Asp<br>30 | Asp | Tyr |
| Tyr | Ser | Thr<br>35 | Trp | Val | Arg | Gln | Pro<br>40 | Pro | Gly | Arg | Gly | Leu<br>45 | Glu | Trp | Ile |
| Gly | Tyr | Val | Phe | Tyr | His | Gly | Thr | Ser | Asp | Thr | Asp | Thr | Pro | Leu | Arg |

```
                    50                      55                        60
    Ser  Arg  Val  Thr  Met  Leu  Val  Asn  Thr  Ser  Lys  Asn  Gln  Phe  Ser  Leu
    65                       70                      75                           80

Arg  Leu  Ser  Ser  Val  Thr  Ala  Ala  Asp  Thr  Ala  Val  Tyr  Tyr  Cys  Ala
                        85                      90                      95

Arg  Asn  Leu  Ile  Ala  Gly  Cys  Ile  Asp  Val  Trp  Gly  Gln  Gly  Ser  Leu
                   100                     105                     110

Val  Thr  Val  Ser  Ser
                   115
```

(2) INFORMATION FOR SEQ ID NO:8:

(i) SEQUENCE CHARACTERISTICS:
    (A) LENGTH: 126 amino acids
    (B) TYPE: amino acid
    (D) TOPOLOGY: linear (ii) MOLECULE TYPE: protein (xi) SEQUENCE DESCRIPTION: SEQ ID NO:8:

```
    Glu  Val  Gln  Leu  Val  Gln  Ser  Gly  Gly  Val  Val  Gln  Pro  Gly  Arg
    1                   5                        10                      15

Ser  Leu  Arg  Leu  Ser  Cys  Ser  Ser  Gly  Phe  Ile  Phe  Ser  Ser  Tyr
                   20                      25                      30

Ala  Met  Tyr  Trp  Val  Arg  Gln  Ala  Pro  Gly  Lys  Gly  Leu  Glu  Trp  Val
              35                      40                      45

Ala  Ile  Ile  Trp  Asp  Asp  Gly  Ser  Asp  Gln  His  Tyr  Ala  Asp  Ser  Val
              50                      55                      60

Lys  Gly  Arg  Phe  Thr  Ile  Ser  Arg  Asn  Asp  Ser  Lys  Asn  Thr  Leu  Phe
    65                       70                      75                           80

Leu  Gln  Met  Asp  Ser  Leu  Arg  Pro  Glu  Asp  Thr  Gly  Val  Tyr  Phe  Cys
                        85                      90                      95

Ala  Arg  Asp  Gly  Gly  His  Gly  Phe  Cys  Ser  Ser  Ala  Ser  Cys  Phe  Gly
                   100                     105                     110

Pro  Asp  Tyr  Trp  Gly  Gln  Gly  Thr  Pro  Val  Thr  Val  Ser  Ser
                   115                     120                     125
```

(2) INFORMATION FOR SEQ ID NO:9:

(i) SEQUENCE CHARACTERISTICS:
    (A) LENGTH: 6 amino acids
    (B) TYPE: amino acid
    (D) TOPOLOGY: linear (ii) MOLECULE TYPE: protein (xi) SEQUENCE DESCRIPTION: SEQ ID NO:9:

```
    Asn  Ser  Gly  Asn  Gln  Lys
    1                   5
```

(2) INFORMATION FOR SEQ ID NO:10:

(i) SEQUENCE CHARACTERISTICS:
    (A) LENGTH: 3 amino acids
    (B) TYPE: amino acid
    (D) TOPOLOGY: linear (ii) MOLECULE TYPE: protein (xi) SEQUENCE DESCRIPTION: SEQ ID NO:10:

```
    Asn  Lys  Gly
    1
```

( 2 ) INFORMATION FOR SEQ ID NO:11:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Gly  Ser  Thr
1
```

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
His  Gly  Phe  Cys  Ser  Ser  Ala  Ser  Cys
1                   5
```

( 2 ) INFORMATION FOR SEQ ID NO:13:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Asp  Ile  Gln  Met  Thr  Gln  Ser  Pro  Ser  Ser  Leu  Ser  Ala  Ser  Val  Gly
1                   5                   10                  15

Asp  Arg  Val  Thr  Ile  Thr  Cys  Arg  Ala  Ser  Gln  Xaa  Ile  Ser  Xaa  Tyr
                20                  25                  30

Leu  Xaa  Trp  Tyr  Gln  Gln  Lys  Pro  Gly  Lys  Ala  Pro  Lys  Leu  Leu  Ile
            35                  40                  45

Tyr  Ala  Ala  Ser  Xaa  Leu  Xaa  Ser  Gly  Val  Pro  Ser  Arg  Phe  Ser  Gly
     50                  55                       60

Ser  Gly  Ser  Gly  Thr  Xaa  Phe  Thr  Leu  Thr  Ile  Ser  Ser  Leu  Gln  Pro
65                  70                  75                          80

Glu  Asp  Phe  Ala  Thr  Tyr  Tyr  Cys  Gln  Gln  Tyr  Xaa  Xaa  Xaa  Pro  Xaa
               85                  90                       95

Thr  Phe  Gly  Gln  Gly  Thr  Lys  Val  Glu  Ile  Lys
              100                 105
```

( 2 ) INFORMATION FOR SEQ ID NO:14:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Glu  Ile  Val  Leu  Thr  Gln  Ser  Pro  Gly  Thr  Leu  Ser  Leu  Ser  Pro  Gly
1                   5                   10                  15

Glu  Arg  Ala  Thr  Leu  Ser  Cys  Arg  Ala  Ser  Gln  Ser  Val  Ser  Ser  Tyr
                20                  25                  30
```

| | | | | | | | | | | | | | | | |
|---|---|---|---|---|---|---|---|---|---|---|---|---|---|---|---|
|Leu|Ala|Trp<br>35|Tyr|Gln|Gln|Lys|Pro|Gly<br>40|Gln|Ala|Pro|Arg<br>45|Leu|Leu|Ile|
|Tyr|Gly<br>50|Ala|Ser|Ser|Arg|Thr<br>55|Gly|Ile|Pro|Asp<br>60|Arg|Phe|Ser|Gly|
|Ser<br>65|Gly|Ser|Gly|Thr|Asp<br>70|Phe|Thr|Leu|Thr|Ile<br>75|Ser|Arg|Leu|Glu|Pro<br>80|
|Gly|Asp|Phe|Ala|Val<br>85|Tyr|Tyr|Cys|Gln|Gln<br>90|Tyr|Gly|Ser|Ser|Pro<br>95|Xaa|
|Thr|Phe|Gly|Gln|Gly<br>100|Thr|Asp|Val|Glu|Ile<br>105|Lys|

(2) INFORMATION FOR SEQ ID NO:15:

(i) SEQUENCE CHARACTERISTICS:
    (A) LENGTH: 108 amino acids
    (B) TYPE: amino acid
    (D) TOPOLOGY: linear (ii) MOLECULE TYPE: protein (xi) SEQUENCE DESCRIPTION: SEQ ID NO:15:

| | | | | | | | | | | | | | | | |
|---|---|---|---|---|---|---|---|---|---|---|---|---|---|---|---|
|Asp<br>1|Ile|Val|Met|Thr<br>5|Gln|Ser|Pro|Leu|Ser<br>10|Leu|Pro|Val|Thr|Pro<br>15|Gly|
|Glu|Pro|Ala|Ser<br>20|Ile|Ser|Cys|Arg|Ser<br>25|Ser|Gln|Ser|Leu|Leu<br>30|Asn|Asn|
|Tyr|Leu|Asn<br>35|Trp|Tyr|Leu|Gln|Lys<br>40|Pro|Gly|Gln|Ser|Pro<br>45|Gln|Leu|Leu|
|Ile|Tyr<br>50|Leu|Gly|Ser|Asn|Arg<br>55|Ala|Ser|Gly|Val<br>60|Pro|Asp|Arg|Phe|Ser|
|Gly<br>65|Ser|Gly|Ser|Gly|Thr<br>70|Asp|Phe|Thr|Leu|Lys<br>75|Ile|Ser|Arg|Val|Glu<br>80|
|Ala|Glu|Asp|Val|Gly<br>85|Val|Tyr|Tyr|Cys|Met<br>90|Gln|Ala|Leu|Gln|Xaa<br>95|Pro|
|Xaa|Thr|Phe|Gly|Gln<br>100|Gly|Thr|Lys|Xaa|Glu<br>105|Ile|Lys|

(2) INFORMATION FOR SEQ ID NO:16:

(i) SEQUENCE CHARACTERISTICS:
    (A) LENGTH: 106 amino acids
    (B) TYPE: amino acid
    (D) TOPOLOGY: linear (ii) MOLECULE TYPE: protein (xi) SEQUENCE DESCRIPTION: SEQ ID NO:16:

| | | | | | | | | | | | | | | | |
|---|---|---|---|---|---|---|---|---|---|---|---|---|---|---|---|
|Xaa<br>1|Ser|Val|Leu|Thr<br>5|Gln|Pro|Pro|Ser|Ala<br>10|Ser|Gly|Thr|Pro|Gly<br>15|Gln|
|Arg|Val|Thr|Ile<br>20|Ser|Cys|Ser|Gly|Ser<br>25|Ser|Ser|Ile|Gly|Xaa<br>30|Asn|Xaa|
|Val|Xaa|Trp<br>35|Tyr|Gln|Gln|Leu|Pro<br>40|Gly|Thr|Ala|Pro|Asp<br>45|Leu|Leu|Ile|
|Tyr|Asn<br>50|Asn|Arg|Pro|Ser|Gly<br>55|Val|Pro|Asp|Arg<br>60|Phe|Ser|Gly|Ser|Lys|
|Ser<br>65|Gly|Thr|Ser|Ala|Ser<br>70|Leu|Ala|Ile|Ser|Gly<br>75|Leu|Gln|Ser|Glu|Asp<br>80|
|Glu|Ala|Asp|Tyr|Tyr<br>85|Cys|Ala|Thr|Trp|Asp<br>90|Asp|Ser|Leu|Asp|Pro<br>95|Val|
|Phe|Gly|Gly|Gly|Thr<br>100|Lys|Thr|Val|Leu|Gly|

100          105

(2) INFORMATION FOR SEQ ID NO:17:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:17:

```
Xaa Ser Ala Leu Thr Gln Pro Ala Ser Val Ser Gly Ser Pro Gly Gln
  1               5                  10                 15

Ser Ile Thr Ile Ser Cys Thr Gly Thr Ser Ser Val Gly Tyr Asn Xaa
                 20                  25                 30

Val Ser Trp Tyr Gln Gln His Pro Gly Lys Ala Pro Lys Leu Ile Tyr
             35                  40              45

Asp Val Arg Pro Ser Gly Val Arg Phe Ser Gly Ser Lys Ser Gly Asn
         50                  55                  60

Thr Ala Ser Leu Thr Ile Ser Gly Leu Gln Ala Glu Asp Glu Ala Asp
 65                  70                  75                  80

Tyr Tyr Cys Ser Ser Tyr Xaa Gly Xaa Xaa Xaa Xaa Val Phe Gly Gly
                 85                  90                  95

Gly Thr Lys Leu Thr Val Leu Gly
                100
```

(2) INFORMATION FOR SEQ ID NO:18:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:18:

```
Ser Tyr Glu Leu Thr Gln Pro Pro Ser Val Ser Val Ser Pro Gly Gln
  1               5                  10                 15

Thr Ala Ile Thr Cys Ser Gly Asp Xaa Leu Xaa Xaa Xaa Tyr Val Xaa
                 20                  25                 30

Trp Tyr Gln Gln Lys Pro Gly Gln Ala Pro Val Leu Val Ile Tyr Asp
             35                  40              45

Arg Pro Ser Gly Ile Pro Gln Arg Phe Ser Gly Ser Ser Thr Thr Ala
         50                  55                  60

Thr Leu Thr Ile Ser Gly Val Gln Ala Asp Glu Ala Asp Tyr Tyr Cys
 65                  70                  75                  80

Gln Xaa Trp Asp Xaa Xaa Xaa Val Val Phe Gly Gly Gly Thr Lys Leu
                 85                  90                  95

Thr Val Leu Gly
             100
```

(2) INFORMATION FOR SEQ ID NO:19:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:19:

-continued

```
Asn  Phe  Met  Leu  Thr  Gln  Pro  His  Ser  Val  Ser  Glu  Ser  Pro  Gly  Lys
1              5                   10                      15

Thr  Val  Thr  Ile  Ser  Cys  Thr  Xaa  Ser  Xaa  Gly  Ile  Ala  Ser  Xaa  Tyr
               20                  25                      30

Val  Gln  Trp  Tyr  Gln  Gln  Arg  Pro  Gly  Ser  Ala  Pro  Thr  Thr  Val  Ile
          35                       40                      45

Tyr  Glu  Asp  Asn  Arg  Pro  Ser  Gly  Val  Pro  Asp  Arg  Phe  Ser  Gly  Ser
     50                       55                      60

Ser  Ser  Asn  Ser  Ala  Ser  Leu  Thr  Ile  Ser  Gly  Leu  Lys  Thr  Glu  Asp
65                       70                       75                      80

Glu  Ala  Asp  Tyr  Tyr  Cys  Gln  Ser  Tyr  Asp  Ser  Xaa  Xaa  Trp  Val  Phe
                85                      90                       95

Gly  Gly  Gly  Thr  Lys  Leu  Thr  Val  Leu  Gly
               100                      105
```

(2) INFORMATION FOR SEQ ID NO:20:

(i) SEQUENCE CHARACTERISTICS:
    (A) LENGTH: 107 amino acids
    (B) TYPE: amino acid
    (D) TOPOLOGY: linear (ii) MOLECULE TYPE: protein (xi) SEQUENCE DESCRIPTION: SEQ ID NO:20:

```
Asp  Ile  Val  Met  Thr  Gln  Ser  Pro  Asp  Ser  Leu  Ala  Val  Ser  Leu  Gly
1              5                   10                      15

Glu  Arg  Ala  Thr  Ile  Asn  Cys  Lys  Ser  Gln  Ser  Val  Leu  Lys  Asn
               20                  25                      30

Tyr  Leu  Ala  Trp  Tyr  Gln  Gln  Lys  Pro  Gly  Gln  Pro  Pro  Lys  Leu  Leu
          35                       40                      45

Ile  Tyr  Trp  Ala  Ser  Arg  Glu  Ser  Gly  Val  Pro  Asp  Arg  Phe  Ser  Gly
     50                       55                      60

Ser  Gly  Ser  Gly  Thr  Asp  Phe  Thr  Leu  Thr  Ile  Ser  Ser  Leu  Gln  Ala
65                       70                       75                      80

Gln  Asp  Val  Ala  Val  Tyr  Tyr  Cys  Gln  Gln  Tyr  Tyr  Ser  Thr  Pro  Xaa
                85                      90                       95

Thr  Phe  Gly  Gly  Gly  Thr  Lys  Xaa  Gly  Ile  Lys
               100                      105
```

(2) INFORMATION FOR SEQ ID NO:21:

(i) SEQUENCE CHARACTERISTICS:
    (A) LENGTH: 105 amino acids
    (B) TYPE: amino acid
    (D) TOPOLOGY: linear (ii) MOLECULE TYPE: protein (xi) SEQUENCE DESCRIPTION: SEQ ID NO:21:

```
Ser  Glu  Leu  Thr  Gln  Pro  Pro  Ser  Val  Ser  Val  Ala  Pro  Gly  Gln  Thr
1              5                   10                      15

Arg  Ile  Thr  Cys  Ser  Gly  Asp  Xaa  Leu  Gly  Xaa  Tyr  Asp  Ala  Xaa  Trp
               20                  25                      30

Tyr  Gln  Gln  Lys  Pro  Gly  Gln  Ala  Pro  Leu  Leu  Val  Ile  Tyr  Gly  Arg
          35                       40                      45

Asn  Arg  Pro  Ser  Gly  Ile  Pro  Asp  Arg  Phe  Ser  Gly  Ser  Ser  Ser  Gly
     50                       55                      60

His  Thr  Ala  Ser  Leu  Thr  Ile  Thr  Gly  Ala  Gln  Ala  Glu  Asp  Glu  Ala
65                       70                       75                      80
```

```
Asp Tyr Tyr Cys Asn Ser Arg Asp Ser Ser Gly Lys Val Leu Phe Gly
                 85                  90                  95

Gly Gly Thr Lys Leu Thr Val Leu Gly
            100             105
```

( 2 ) INFORMATION FOR SEQ ID NO:22:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Ser Ala Leu Thr Gln Pro Pro Ser Ala Ser Gly Ser Pro Gly Gln Ser
1               5                   10                  15

Val Thr Ile Ser Cys Thr Gly Thr Ser Ser Val Gly Xaa Xaa Tyr Val
            20                  25                  30

Ser Trp Tyr Gln Gln His Gly Ala Pro Lys Ile Glu Val Arg Pro Ser
            35                  40                  45

Gly Val Pro Asp Arg Phe Ser Gly Ser Lys Ser Asn Thr Ala Ser Leu
        50                  55                  60

Thr Val Ser Gly Leu Ala Glu Asp Glu Ala Asp Tyr Tyr Cys Ser Ser
65                  70                  75                  80

Tyr Xaa Xaa Xaa Xaa Xaa Phe Val Phe Gly Gly Thr Lys Thr Val Leu
                85                  90                  95
```

( 2 ) INFORMATION FOR SEQ ID NO:23:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Met Xaa Trp Val Arg Gln Ala Pro Gly Lys Gly Leu Glu Trp Val
            35                  40                  45

Xaa Xaa Ile Xaa Xaa Lys Xaa Xaa Gly Xaa Xaa Tyr Ala Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Xaa Xaa Trp Gly Gln Gly Thr
                100                 105                 110

Leu Val Thr Val Ser Ser
            115
```

( 2 ) INFORMATION FOR SEQ ID NO:24:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| Gln | Val | Gln | Leu | Val | Gln | Ser | Gly | Ala | Glu | Val | Lys | Lys | Pro | Gly | Xaa |
|-----|-----|-----|-----|-----|-----|-----|-----|-----|-----|-----|-----|-----|-----|-----|-----|
| 1   |     |     |     | 5   |     |     |     |     | 10  |     |     |     |     |     | 15  |
| Ser | Val | Xaa | Val | Ser | Cys | Lys | Xaa | Ser | Gly | Tyr | Tyr | Phe | Xaa | Xaa | Tyr |
|     |     |     | 20  |     |     |     |     | 25  |     |     |     |     | 30  |     |     |
| Xaa | Ile | Xaa | Trp | Val | Arg | Gln | Ala | Pro | Gly | Xaa | Gly | Leu | Glu | Trp | Val |
|     |     | 35  |     |     |     |     | 40  |     |     |     |     | 45  |     |     |     |
| Gly | Xaa | Ile | Xaa | Pro | Xaa | Xaa | Gly | Xaa | Thr | Xaa | Tyr | Ala | Pro | Xaa | Phe |
|     | 50  |     |     |     |     | 55  |     |     |     |     |     | 60  |     |     |     |
| Gln | Gly | Arg | Val | Thr | Xaa | Thr | Arg | Asp | Xaa | Ser | Xaa | Asn | Thr | Ala | Tyr |
| 65  |     |     |     |     | 70  |     |     |     |     | 75  |     |     |     |     | 80  |
| Met | Glu | Leu | Xaa | Ser | Leu | Arg | Ser | Glu | Asp | Thr | Ala | Val | Tyr | Tyr | Cys |
|     |     |     |     | 85  |     |     |     |     | 90  |     |     |     |     | 95  |     |
| Ala | Arg | Xaa | Xaa | Xaa | Xaa | Xaa | Xaa | Xaa | Xaa | Xaa | Trp | Gly | Gln | Gly |
|     |     |     |     | 100 |     |     |     |     |     | 105 |     |     |     |     | 110 |
| Thr | Leu | Val | Thr | Val | Ser | Ser |
|     |     | 115 |     |     |     |     |

( 2 ) INFORMATION FOR SEQ ID NO:25:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| Xaa | Val | Thr | Leu | Xaa | Glu | Ser | Gly | Pro | Xaa | Leu | Val | Leu | Pro | Thr | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     |     | 15  |
| Thr | Leu | Thr | Leu | Thr | Cys | Thr | Val | Ser | Gly | Xaa | Ser | Leu | Ser | Xaa | Xaa |
|     |     |     | 20  |     |     |     |     | 25  |     |     |     |     | 30  |     |     |
| Xaa | Val | Xaa | Trp | Ile | Arg | Gln | Pro | Pro | Gly | Lys | Xaa | Leu | Glu | Trp | Leu |
|     |     | 35  |     |     |     |     | 40  |     |     |     |     | 45  |     |     |     |
| Ala | Xaa | Ile | Xaa | Ile | Asp | Asp | Xaa | Tyr | Xaa | Thr | Ser | Leu | Arg | Ser |
|     | 50  |     |     |     |     | 55  |     |     |     |     | 60  |     |     |     |
| Arg | Leu | Thr | Ile | Ser | Lys | Asp | Thr | Ser | Lys | Asn | Gln | Val | Val | Leu | Xaa |
| 65  |     |     |     |     | 70  |     |     |     |     | 75  |     |     |     |     | 80  |
| Xaa | Xaa | Xaa | Xaa | Asp | Pro | Xaa | Asp | Thr | Ala | Thr | Tyr | Tyr | Cys | Ala | Arg |
|     |     |     |     | 85  |     |     |     |     | 90  |     |     |     |     | 95  |     |
| Xaa | Xaa | Xaa | Xaa | Xaa | Xaa | Xaa | Xaa | Asp | Val | Trp | Gly | Gln | Gly | Thr | Thr |
|     |     |     |     | 100 |     |     |     |     | 105 |     |     |     |     | 110 |     |
| Val | Thr | Val | Ser | Ser |
|     |     | 115 |     |     |

( 2 ) INFORMATION FOR SEQ ID NO:26:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| Asp | Ile | Lys | Met | Thr | Gln | Ser | Pro | Ser | Ser | Met | Tyr | Ala | Ser | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     |     | 15  |

-continued

```
Glu  Arg  Val  Thr  Ile  Thr  Cys  Lys  Ala  Ser  Gln  Asp  Ile  Asn  Ser  Tyr
               20                       25                       30

Leu  Ser  Trp  Phe  Gln  Gln  Lys  Pro  Gly  Lys  Ser  Pro  Lys  Thr  Leu  Ile
          35                       40                       45

Tyr  Arg  Ala  Asn  Arg  Leu  Val  Asp  Gly  Val  Pro  Ser  Arg  Phe  Ser  Gly
     50                       55                       60

Ser  Gly  Ser  Gly  Gln  Asp  Tyr  Ser  Leu  Thr  Ile  Ser  Ser  Leu  Asp  Tyr
65                       70                       75                       80

Glu  Asp  Met  Gly  Ile  Tyr  Tyr  Cys  Gln  Gln  Tyr  Asp  Glu  Ser  Pro  Trp
               85                       90                       95

Thr  Phe  Gly  Gly  Gly  Thr  Lys  Leu  Glu  Ile  Lys
               100                      105
```

( 2 ) INFORMATION FOR SEQ ID NO:27:

( i ) SEQUENCE CHARACTERISTICS:
      ( A ) LENGTH: 107 amino acids
      ( B ) TYPE: amino acid
      ( D ) TOPOLOGY: linear ( i i ) MOLECULE TYPE: protein ( x i ) SEQUENCE DESCRIPTION: SEQ ID NO:27:

```
Asp  Ile  Gln  Met  Thr  Gln  Ser  Pro  Ser  Ser  Met  Ser  Ala  Ser  Leu  Gly
1                        5                        10                       15

Asp  Arg  Val  Thr  Ile  Thr  Cys  Arg  Ala  Ser  Gln  Asp  Ile  Asn  Ser  Tyr
               20                       25                       30

Leu  Ser  Trp  Phe  Gln  Gln  Lys  Pro  Gly  Lys  Ser  Pro  Lys  Thr  Leu  Ile
          35                       40                       45

Tyr  Arg  Ala  Asn  Arg  Leu  Val  Asp  Gly  Val  Pro  Ser  Arg  Phe  Ser  Gly
     50                       55                       60

Ser  Gly  Ser  Gly  Thr  Asp  Tyr  Thr  Leu  Thr  Ile  Ser  Ser  Leu  Gln  Tyr
65                       70                       75                       80

Glu  Asp  Phe  Gly  Ile  Tyr  Tyr  Cys  Gln  Gln  Tyr  Asp  Glu  Ser  Pro  Trp
               85                       90                       95

Thr  Phe  Gly  Gly  Gly  Thr  Lys  Leu  Glu  Ile  Lys
               100                      105
```

( 2 ) INFORMATION FOR SEQ ID NO:28:

( i ) SEQUENCE CHARACTERISTICS:
      ( A ) LENGTH: 118 amino acids
      ( B ) TYPE: amino acid
      ( D ) TOPOLOGY: linear ( i i ) MOLECULE TYPE: protein ( x i ) SEQUENCE DESCRIPTION: SEQ ID NO:28:

```
Gln  Ile  Gln  Leu  Val  Gln  Ser  Gly  Pro  Glu  Leu  Lys  Lys  Pro  Gly  Glu
1                        5                        10                       15

Thr  Val  Lys  Ile  Ser  Cys  Lys  Ala  Ser  Gly  Tyr  Thr  Phe  Thr  Asn  Tyr
               20                       25                       30

Gly  Met  Asn  Trp  Val  Lys  Gln  Ala  Pro  Gly  Lys  Gly  Leu  Arg  Trp  Met
          35                       40                       45

Gly  Trp  Ile  Asn  Thr  His  Thr  Gly  Glu  Pro  Thr  Tyr  Ala  Asp  Asp  Phe
     50                       55                       60

Lys  Gly  Arg  Phe  Ala  Phe  Ser  Leu  Glu  Thr  Ser  Ala  Ser  Thr  Ala  Tyr
65                       70                       75                       80

Leu  Gln  Ile  Asn  Asn  Leu  Lys  Asn  Glu  Asp  Thr  Ala  Thr  Tyr  Phe  Cys
               85                       90                       95
```

Thr Arg Arg Gly Tyr Asp Trp Tyr Phe Asp Val Trp Gly Ala Gly Thr
              100                 105                 110

Thr Val Thr Val Ser Ser
            115

( 2 ) INFORMATION FOR SEQ ID NO:29:

( i ) SEQUENCE CHARACTERISTICS:
            ( A ) LENGTH: 118 amino acids
            ( B ) TYPE: amino acid
            ( D ) TOPOLOGY: linear ( i i ) MOLECULE TYPE: protein ( x i ) SEQUENCE DESCRIPTION: SEQ ID NO:29:

Gln Ile Gln Leu Val Gln Ser Gly Pro Gly Leu Lys Lys Pro Gly Gly
1                5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Arg Trp Met
            35                  40                  45

Gly Trp Ile Asn Thr His Thr Gly Glu Pro Thr Tyr Ala Asp Asp Phe
    50                  55                  60

Lys Gly Arg Phe Thr Phe Ser Leu Asp Thr Ser Lys Ser Thr Ala Tyr
65                      70                  75                  80

Leu Gln Ile Asn Ser Leu Arg Ala Glu Asp Thr Ala Thr Tyr Phe Cys
                85                  90                  95

Thr Arg Arg Gly Tyr Asp Trp Tyr Phe Asp Val Trp Gly Gln Gly Thr
              100                 105                 110

Thr Val Thr Val Ser Ser
            115

( 2 ) INFORMATION FOR SEQ ID NO:30:

( i ) SEQUENCE CHARACTERISTICS:
            ( A ) LENGTH: 98 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:30:

AGTCGTCGAC ACGATGGACA TGAGGACCCC TGCTCAGTTT CTTGGCATCC TCCTACTCTG     60

GTTTCCAGGT ATCAAATGTG ACATCCAGAT GACTCAGT                             98

( 2 ) INFORMATION FOR SEQ ID NO:31:

( i ) SEQUENCE CHARACTERISTICS:
            ( A ) LENGTH: 80 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:31:

TGACTCGCCC GGCAAGTGAT AGTGACTCTG TCTCCCAGAC ATGCAGACAT GGAAGATGAG     60

GACTGAGTCA TCTGGATGTC                                                 80

( 2 ) INFORMATION FOR SEQ ID NO:32:

( i ) SEQUENCE CHARACTERISTICS:
 ( A ) LENGTH: 79 base pairs
 ( B ) TYPE: nucleic acid
 ( C ) STRANDEDNESS: single
 ( D ) TOPOLOGY: linear ( i i ) MOLECULE TYPE: DNA ( x i ) SEQUENCE DESCRIPTION: SEQ ID NO:32:

TCACTTGCCG GGCGAGTCAG GACATTAATA GCTATTTAAG CTGGTTCCAG CAGAAACCAG      60

GGAAATCTCC TAAGACCCT      79

( 2 ) INFORMATION FOR SEQ ID NO:33:

( i ) SEQUENCE CHARACTERISTICS:
  ( A ) LENGTH: 79 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:33:

GATCCACTGC CACTGAACCT TGATGGGACC CCATCTACCA ATCTGTTTGC ACGATAGATC      60

AGGGTCTTAG GAGATTTCC      79

( 2 ) INFORMATION FOR SEQ ID NO:34:

( i ) SEQUENCE CHARACTERISTICS:
  ( A ) LENGTH: 82 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:34:

GGTTCAGTGG CAGTGGATCT GGGACAGATT ATACTCTCAC CATCAGCAGC CTGCAATATG      60

AAGATTTTGG AATTTATTAT TG      82

( 2 ) INFORMATION FOR SEQ ID NO:35:

( i ) SEQUENCE CHARACTERISTICS:
  ( A ) LENGTH: 82 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:35:

GTTTGATTTC AAGCTTGGTG CCTCCACCGA ACGTCCACGG AGACTCATCA TACTGTTGAC      60

AATAATAAAT TCCAAAATCT TC      82

( 2 ) INFORMATION FOR SEQ ID NO:36:

( i ) SEQUENCE CHARACTERISTICS:
  ( A ) LENGTH: 85 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:36:

TGTCGACATC ATGGCTTGGG TGTGGACCTT GCTATTCCTG ATGGCAGCTG CCCAAAGTGC      60

CCAAGCACAG ATCCAGTTGG TGCAG 85

(2) INFORMATION FOR SEQ ID NO:37:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

AAGGTATACC CAGAAGCTGC GCAGGAGATT CTGACGGACC CTCCAGGCTT CTTCAGGCCA 60

GGTCCAGACT GCACCAACTG GATCT 85

(2) INFORMATION FOR SEQ ID NO:38:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

GCAGCTTCTG GGTATACCTT CACAAACTAT GGAATGAACT GGGTGAAGCA GGCTCCAGGA 60

AAGGGTTTAA GGTGGATGGG CTGG 84

(2) INFORMATION FOR SEQ ID NO:39:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

AAAGAGAAGG TAAACCGTCC CTTGAAGTCA TCAGCATATG TTGGCTCTCC AGTGTGGGTG 60

TTTATCCAGC CCATCCACCT TAAAC 85

(2) INFORMATION FOR SEQ ID NO:40:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

GACGGTTTAC CTTCTCTTTG GACACGTCTA AGTGCACTGC CTATTTACAG ATCAACAGCC 60

TCAGAGCCGA GGACACGGCT ACAT 84

(2) INFORMATION FOR SEQ ID NO:41:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA ( x i ) SEQUENCE DESCRIPTION: SEQ ID NO:41:

AGGAGACGGT GACCGTGGTC CCTTGGCCCC AGACATCGAA GTACCAGTCG TAACCCCGTC  60

TTGTACAGAA ATATGTAGCC GTGTCCTCGG C  91

( 2 ) INFORMATION FOR SEQ ID NO:42:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

ACTAGTGTCG ACATCATGGC TTGGGT  26

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GAGGAGACGG TGACCGTGGT  20

( 2 ) INFORMATION FOR SEQ ID NO:44:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

AGTCGTCGAC ACGATGGACA TGAGGAC  27

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

GTTTGATTTC AAGCTTGGTG C  21

( 2 ) INFORMATION FOR SEQ ID NO:46:

( i ) SEQUENCE CHARACTERISTICS:
        ( A ) LENGTH: 425 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

```
ACTAGTGTCG ACATCATGGC TTGGGTGTGG ACCTTGCTAT TCCTGATGGC AGCTGCCCAA        60

AGTGCCCAAG CACAGATCCA GTTGGTGCAG TCTGGACCTG GCCTGAAGAA GCCTGGAGGG       120

TCCGTCAGAA TCTCCTGCGC AGCTTCTGGG TATACCTTCA CAAACTATGG AATGAACTGG       180

GTGAAGCAGG CTCCAGGAAA GGGTTTAAGG TGGATGGGCT GGATAAACAC CCACACTGGA       240

GAGCCAACAT ATGCTGATGA CTTCAAGGGA CGGTTTACCT TCTCTTTGGA CACGTCTAAG       300

AGCACTGCCT ATTTACAGAT CAACAGCCTC AGAGCCGAGG ACACGGCTAC ATATTTCTGT       360

ACAAGACGGG GTTACGACTG GTACTTCGAT GTCTGGGGCC AAGGGACCAC GGTCACCGTC       420

TCCTC                                                                   425
```

( 2 ) INFORMATION FOR SEQ ID NO:47:

( i ) SEQUENCE CHARACTERISTICS:
        ( A ) LENGTH: 401 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

```
AGTCGTCGAC ACGATGGACA TGAGGACCCC TGCTCAGTTT CTTGGCATCC TCCTACTCTG        60

GTTTCCAGGT ATCAAATGTG ACATCCAGAT GACTCAGTCT CCATCTTCCA TGTCTGCATC       120

TCTGGGAGAC AGAGTCACTA TCACTTGCCG GGCGAGTCAG GACATTAATA GCTATTTAAG       180

CTGGTTCCAG CAGAAACCAG GGAAATCTCC TAAGACCCTG ATCTATCGTG CAAACAGATT       240

GGTAGATGGG GTCCCATCAA GGTTCAGTGG CAGTGGATCT GGGACAGATT ATACTCTCAC       300

CATCAGCAGC CTGCAATATG AAGATTTTGG AATTTATTAT TGTCAACAGT ATGATGAGTC       360

TCCGTGGACG TTCGGTGGAG GCACCAAGCT TGAAATCAAA C                           401
```

( 2 ) INFORMATION FOR SEQ ID NO:48:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Thr Trp
             20                  25                  30

Leu Ala Trp Tyr Gln Gln Lys Pro Gly Lys Ala Pro Lys Leu Leu Met
         35                  40                  45

Tyr Lys Ala Ser Ser Leu Glu Ser Gly Val Pro Ser Arg Phe Ile Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Asp Ser Lys
                 85                  90                  95

Met Phe Gly Gln Gly Thr Lys Val Glu Val Lys
                100                 105
```

( 2 ) INFORMATION FOR SEQ ID NO:49:

( i ) SEQUENCE CHARACTERISTICS:

( A ) LENGTH: 79 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:49:

TCACTTGCCG GGCGAATCAG GACATTAATA GCTATTTAAG CTGGTTCCAG CAGAAACCAG    60

GGAAAGCTCC TAAGACCCT    79

( 2 ) INFORMATION FOR SEQ ID NO:50:

( i ) SEQUENCE CHARACTERISTICS:
( A ) LENGTH: 106 amino acids
( B ) TYPE: amino acid
( D ) TOPOLOGY: linear ( i i ) MOLECULE TYPE: protein ( x i ) SEQUENCE DESCRIPTION: SEQ ID NO:50:

```
Asp Ile Gln Leu Thr Gln Ser Pro Ser Ser Met Ser Ala Ser Pro Gly
1               5                  10                  15

Asp Arg Val Thr Ile Thr Cys Arg Ala Ser Ser Ser Ile Ser Tyr Met
            20                  25                  30

His Trp Phe Gln Gln Lys Pro Gly Lys Ser Pro Lys Leu Trp Ile Tyr
        35                  40                  45

Thr Thr Ser Asn Leu Ala Ser Gly Val Pro Ser Arg Phe Ser Gly Ser
    50                  55                  60

Gly Ser Gly Thr Ser Tyr Thr Leu Thr Ile Ser Ser Met Gln Ala Glu
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Leu Glu Leu Lys
                100                 105
```

( 2 ) INFORMATION FOR SEQ ID NO:51:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:51:

TGACTCGCCC GGCAAGTGAT AGTGACTCTG TCTCCTACAG ATGCAGACAG GGAAGATGGA    60

GACTGAGTCA TCTGGATGTC    80

( 2 ) INFORMATION FOR SEQ ID NO:52:

( i ) SEQUENCE CHARACTERISTICS:
( A ) LENGTH: 117 amino acids
( B ) TYPE: amino acid
( D ) TOPOLOGY: linear ( i i ) MOLECULE TYPE: protein ( x i ) SEQUENCE DESCRIPTION: SEQ ID NO:52:

```
Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Arg Ser
            20                  25                  30
```

|     |     |     |     |     |     |     |     |     |     |     |     |     |     |     |
|-----|-----|-----|-----|-----|-----|-----|-----|-----|-----|-----|-----|-----|-----|-----|
| Ala | Ile | Ile | Trp | Val | Arg | Gln | Ala | Pro | Gly | Gln | Gly | Leu | Glu | Trp | Met |
|     |     | 35  |     |     |     | 40  |     |     |     |     | 45  |     |     |     |
| Gly | Gly | Ile | Val | Pro | Met | Phe | Gly | Pro | Pro | Asn | Tyr | Ala | Gln | Lys | Phe |
|     | 50  |     |     |     |     | 55  |     |     |     | 60  |     |     |     |     |
| Gln | Gly | Arg | Val | Thr | Ile | Thr | Ala | Asp | Glu | Ser | Thr | Asn | Thr | Ala | Tyr |
| 65  |     |     |     |     | 70  |     |     |     | 75  |     |     |     |     |     | 80 |
| Met | Glu | Leu | Ser | Ser | Leu | Arg | Ser | Glu | Asp | Thr | Ala | Phe | Tyr | Phe | Cys |
|     |     |     |     | 85  |     |     |     |     | 90  |     |     |     |     | 95  |     |
| Ala | Gly | Gly | Tyr | Gly | Ile | Tyr | Ser | Pro | Glu | Glu | Tyr | Asn | Gly | Gly | Leu |
|     |     |     | 100 |     |     |     |     |     | 105 |     |     |     | 110 |     |     |
| Val | Thr | Val | Ser | Ser |     |     |     |     |     |     |     |     |     |     |
|     |     | 115 |     |     |     |     |     |     |     |     |     |     |     |     |

( 2 ) INFORMATION FOR SEQ ID NO:53:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

GATCCACTGC CACTGAACCT TGATGGGACC CCAGATTCCA ATCTGTTTGC ACGATAGATC    60

AGGGTCTTAG GAGCTTTCC    79

( 2 ) INFORMATION FOR SEQ ID NO:54:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

|     |     |     |     |     |     |     |     |     |     |     |     |     |     |     |     |
|-----|-----|-----|-----|-----|-----|-----|-----|-----|-----|-----|-----|-----|-----|-----|-----|
| Gln | Val | Gln | Leu | Gln | Gln | Ser | Gly | Ala | Glu | Val | Ala | Lys | Pro | Gly | Ala |
| 1   |     |     |     | 5   |     |     |     |     | 10  |     |     |     |     | 15  |     |
| Ser | Val | Lys | Met | Ser | Cys | Lys | Ala | Ser | Gly | Tyr | Thr | Phe | Thr | Ser | Tyr |
|     |     |     | 20  |     |     |     |     | 25  |     |     |     |     | 30  |     |     |
| Arg | Met | His | Trp | Val | Lys | Gln | Ala | Pro | Gly | Gln | Gly | Leu | Glu | Trp | Ile |
|     |     | 35  |     |     |     | 40  |     |     |     |     | 45  |     |     |     |     |
| Gly | Tyr | Ile | Asn | Pro | Ser | Thr | Gly | Tyr | Thr | Glu | Tyr | Asn | Gln | Lys | Phe |
|     | 50  |     |     |     |     | 55  |     |     |     | 60  |     |     |     |     |     |
| Lys | Gly | Lys | Ala | Thr | Leu | Thr | Ala | Asp | Lys | Ser | Ser | Ser | Thr | Ala | Tyr |
| 65  |     |     |     |     | 70  |     |     |     | 75  |     |     |     |     |     | 80 |
| Met | Glu | Leu | Ser | Ser | Leu | Arg | Ser | Glu | Asp | Thr | Ala | Val | Tyr | Tyr | Cys |
|     |     |     |     | 85  |     |     |     |     | 90  |     |     |     |     | 95  |     |
| Ala | Arg | Gly | Gly | Gly | Val | Phe | Asp | Tyr | Trp | Gly | Gln | Gly | Thr | Thr | Leu |
|     |     |     | 100 |     |     |     |     | 105 |     |     |     |     | 110 |     |     |
| Thr | Val | Ser | Ser |     |     |     |     |     |     |     |     |     |     |     |
|     |     | 115 |     |     |     |     |     |     |     |     |     |     |     |     |

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

GAGATCCAGT TGGTGCAGTC TG                                                    22

( 2 ) INFORMATION FOR SEQ ID NO:56:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

TGTCGACATC ATGGCTTGGG TGTGGACCTT GCTATTCCTG ATGGCAGCTG CCCAAAGTGC            60

CCAAGCAGAG ATCCAGTTGG TGCAG                                                 85

( 2 ) INFORMATION FOR SEQ ID NO:57:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AAGGTATACC CAGAAGCTGC GCAGGAGATT CTGACGGACC CTCCAGGCTT CACCAGGCCT            60

CCTCCAGACT GCACCAACTG GATCTC                                                86

( 2 ) INFORMATION FOR SEQ ID NO:58:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GCAGCTTCTG GGTATACCTT CACAAACTAT GGAATGAACT GGGTGCGCCA GGCTCCAGGA            60

AAGAATTTAG AGTGGATGGG CTGG                                                  84

( 2 ) INFORMATION FOR SEQ ID NO:59:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

AAAGAGAAGG TAAACCGTCC CTTGAAAGAA TCAGCATATG TTGGCTCTCC AGTGTGGGTG            60

TTTATCCAGC CCATCCACTC TAAAC                                                 85

( 2 ) INFORMATION FOR SEQ ID NO:60:

( i ) SEQUENCE CHARACTERISTICS:
        ( A ) LENGTH: 87 base pairs (B) TYPE: nucleic acid
              (C) STRANDEDNESS: single
              (D) TOPOLOGY: linear (i i) MOLECULE TYPE: DNA (x i) SEQUENCE DESCRIPTION: SEQ ID NO:60:

GACGGTTTAC CTTCTCTTTG GACGATTCTA AGAACACTGC CTATTTACAG ATCAACAGCC      60

TCAGAGCCGA GGACACGGCT GTGTATT      87

(2) INFORMATION FOR SEQ ID NO:61:

(i) SEQUENCE CHARACTERISTICS:
              (A) LENGTH: 92 base pairs
              (B) TYPE: nucleic acid
              (C) STRANDEDNESS: single
              (D) TOPOLOGY: linear (i i) MOLECULE TYPE: DNA (x i) SEQUENCE DESCRIPTION: SEQ ID NO:61:

GAGGAGACGG TGACCGTGGT CCCTTGGCCC CAGACATCGA AGTACCAGTC GTAACCCCGT      60

CTTGTACAGA AATACACAGC CGTGTCCTCG GC      92

(2) INFORMATION FOR SEQ ID NO:62:

(i) SEQUENCE CHARACTERISTICS:
              (A) LENGTH: 80 base pairs
              (B) TYPE: nucleic acid
              (C) STRANDEDNESS: single
              (D) TOPOLOGY: linear (i i) MOLECULE TYPE: DNA (x i) SEQUENCE DESCRIPTION: SEQ ID NO:62:

TGACTCGCCC GGCAAGTGAT AGTGACTCTG TCTCCTACAG ATGCAGACAG GGAAGATGGA      60

GACTGAGTCA TCTGGATGTC      80

(2) INFORMATION FOR SEQ ID NO:63:

(i) SEQUENCE CHARACTERISTICS:
              (A) LENGTH: 79 base pairs
              (B) TYPE: nucleic acid
              (C) STRANDEDNESS: single
              (D) TOPOLOGY: linear (i i) MOLECULE TYPE: DNA (x i) SEQUENCE DESCRIPTION: SEQ ID NO:63:

TCACTTGCCG GGCGAATCAG GACATTAATA GCTATTTAAG CTGGTTCCAG CAGAAACCAG      60

GGAAAGCTCC TAAGACCCT      79

(2) INFORMATION FOR SEQ ID NO:64:

(i) SEQUENCE CHARACTERISTICS:
              (A) LENGTH: 79 base pairs
              (B) TYPE: nucleic acid
              (C) STRANDEDNESS: single
              (D) TOPOLOGY: linear (i i) MOLECULE TYPE: DNA (x i) SEQUENCE DESCRIPTION: SEQ ID NO:64:

GATCCACTGC CACTGAACCT TGATGGGACC CCAGATTCCA ATCTGTTTGC ACGATAGATC      60

AGGGTATTAG GAGCTTTCC      79

(2) INFORMATION FOR SEQ ID NO:65:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:65:

CGGACCCACC TCCACCAGAT ACCACCGC               28

(2) INFORMATION FOR SEQ ID NO:66:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:66:

GACATCCAGA TGACTCAGT                   19

(2) INFORMATION FOR SEQ ID NO:67:

(i) SEQUENCE CHARACTERISTICS:
  (A) LENGTH: 49 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:67:

GGTGGAGGTG GGTCCGGAGG TGGAGGATCT GAGATCCAGT TGGTGCAGT     49

(2) INFORMATION FOR SEQ ID NO:68:

(i) SEQUENCE CHARACTERISTICS:
  (A) LENGTH: 35 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:68:

TGTACTCGAG CCCATCATGA GGAGACGGTG ACCGT            35

(2) INFORMATION FOR SEQ ID NO:69:

(i) SEQUENCE CHARACTERISTICS:
  (A) LENGTH: 49 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:69:

GGTGGAGGTG GGTCCGGAGG TGGAGGATCT GACATCCAGA TGACTCAGT     49

(2) INFORMATION FOR SEQ ID NO:70:

(i) SEQUENCE CHARACTERISTICS:
  (A) LENGTH: 37 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:70:

TGTACTCGAG CCCATCATTT CATCTCAAGC TTGGTGC 37

( 2 ) INFORMATION FOR SEQ ID NO:71:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:71:

GAGATCCAGT TGGTGCAGTC TG 22

( 2 ) INFORMATION FOR SEQ ID NO:72:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:72:

CGGACCCACC TCCACCAGAT CCACCGCCAC CTTTCATCTC AAGCTTGGTG C 51

( 2 ) INFORMATION FOR SEQ ID NO:73:

( i ) SEQUENCE CHARACTERISTICS:
( A ) LENGTH: 51 amino acids
( B ) TYPE: amino acid
( D ) TOPOLOGY: linear ( i i ) MOLECULE TYPE: protein ( x i ) SEQUENCE DESCRIPTION: SEQ ID NO:73:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
            35                  40                  45

Tyr Arg Ala
        50

( 2 ) INFORMATION FOR SEQ ID NO:74:

( i ) SEQUENCE CHARACTERISTICS:
( A ) LENGTH: 51 amino acids
( B ) TYPE: amino acid
( D ) TOPOLOGY: linear ( i i ) MOLECULE TYPE: protein ( x i ) SEQUENCE DESCRIPTION: SEQ ID NO:74:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr

|  |  | 20 |  |  | 25 |  |  | 30 |  |
|---|---|---|---|---|---|---|---|---|---|

Leu Ser Trp Phe Gln Gln Lys Pro Gly Lys Ala Pro Lys Thr Leu Met
        35                      40                 45

Tyr Arg Ala
    50

( 2 ) INFORMATION FOR SEQ ID NO:75:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

| GAGATCCAGT | TGGTGCAGTC | TGGAGGAGGC | CTGGTGAAGC | CTGGAGGGTC | CGTCAGAATC | 60 |
|---|---|---|---|---|---|---|
| TCCTGCGCAG | CTTCTGGGTA | TACCTTCACA | AACTATGGAA | TGAACTGGGT | GCGCCAGGCT | 120 |
| CCAGGAAAGG | GTTTAGAGTG | GATGGGCTGG | ATAAACACCC | ACACTGGAGA | GCCAACATAT | 180 |
| GCTGATTCTT | TCAAGGGACG | GTTTACCTTC | TCTTTGGACG | ATTCTAAGAA | CACTGCCTAT | 240 |
| TTACAGATCA | ACAGCCTCAG | AGCCGAGGAC | ACGGCTGTGT | ATTTCTGTAC | AAGACGGGGT | 300 |
| TACGACTGGT | ACTTCGATGT | CTGGGGCCAA | GGGACCACGG | TCACCGTCTC | CTCC | 354 |

( 2 ) INFORMATION FOR SEQ ID NO:76:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

| GACATCCAGA | TGACTCAGTC | TCCATCTTCC | CTGTCTGCAT | CTGTAGGAGA | CAGAGTCACT | 60 |
|---|---|---|---|---|---|---|
| ATCACTTGCC | GGGCGAGTCA | GGACATTAAT | AGCTATTTAA | GCTGGTTCCA | GCAGAAACCA | 120 |
| GGGAAAGCTC | CTAAGACCCT | GATCTATCGT | GCAAACAGAT | TGGAATCTGG | GGTCCCATCA | 180 |
| AGGTTCAGTG | GCAGTGGATC | TGGGACAGAT | TATACTCTCA | CCATCAGCAG | CCTGCAATAT | 240 |
| GAAGATTTTG | GAATTTATTA | TTGTCAACAG | TATGATGAGT | CTCCGTGGAC | GTTCGGTGGA | 300 |
| GGCACCAAGC | TTGAAATCAA | A |  |  |  | 321 |

( 2 ) INFORMATION FOR SEQ ID NO:77:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

TGATGCGGCC  GACATCTCAA  GCTTGGTGC                                    29

( 2 ) INFORMATION FOR SEQ ID NO:78:

( i ) SEQUENCE CHARACTERISTICS:
        ( A ) LENGTH: 29 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:78:

TGATGCGGCC GACATCTCAA GCTTGGTGC 29

( 2 ) INFORMATION FOR SEQ ID NO:79:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:79:

TCTAGGTCAC CGTCTCCTCA CCATCTGGAC AGGCTGGA 38

( 2 ) INFORMATION FOR SEQ ID NO:80:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:80:

TTCGAAGCTT GAGATGAAAC CATCTGGACA GGCTGGA 37

( 2 ) INFORMATION FOR SEQ ID NO:81:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:81:

TGTACTCGAG CCCACTAGTC ATGGTGGTGA TGGTGTTTCA TCTCAAGCTT GGTGC 55

( 2 ) INFORMATION FOR SEQ ID NO:82:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:82:

TGTACTCGAG CCCACTAGTG ATGGTGGTGA TGGTGTGAGG AGACGGTGAC CGT 53

( 2 ) INFORMATION FOR SEQ ID NO:83:

( i ) SEQUENCE CHARACTERISTICS:
( A ) LENGTH: 106 amino acids
( B ) TYPE: amino acid
( D ) TOPOLOGY: linear ( i i ) MOLECULE TYPE: protein ( x i ) SEQUENCE DESCRIPTION: SEQ ID NO:83:

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Ile Ser Tyr Met
                20                  25                  30

His Trp Phe Gln Gln Lys Pro Gly Thr Ser Pro Lys Leu Trp Ile Tyr
            35                  40                  45

Thr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Ser Gly Thr Lys Leu Glu Leu Lys
            100                 105

( 2 ) INFORMATION FOR SEQ ID NO:84:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:84:

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
            35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Val Glu Val Lys
            100                 105

( 2 ) INFORMATION FOR SEQ ID NO:85:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:85:

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
                20                  25                  30

Arg Met His Trp Val Lys Gln Arg Pro Gly Gln Gly Leu Glu Trp Ile
            35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

```
              Met   Gln   Leu   Ser   Ser   Leu   Thr   Phe   Glu   Asp   Ser   Ala   Val   Tyr   Tyr   Cys
                                      85                            90                            95

Ala   Arg   Gly   Gly   Gly   Val   Phe   Asp   Tyr   Trp   Gly   Gln   Gly   Thr   Thr   Leu
                                      100                           105                           110

Thr   Val   Ser   Ser
                                115
```

( 2 ) INFORMATION FOR SEQ ID NO:86:

( i ) SEQUENCE CHARACTERISTICS:
      ( A ) LENGTH: 116 amino acids
      ( B ) TYPE: amino acid
      ( D ) TOPOLOGY: linear ( i i ) MOLECULE TYPE: protein ( x i ) SEQUENCE DESCRIPTION: SEQ ID NO:86:

```
              Gln   Val   Gln   Leu   Val   Gln   Ser   Gly   Ala   Glu   Val   Lys   Lys   Pro   Gly   Ser
              1                       5                             10                            15

Ser   Val   Lys   Val   Ser   Cys   Lys   Ala   Ser   Gly   Tyr   Thr   Phe   Thr   Ser   Tyr
                                      20                            25                            30

Arg   Met   His   Trp   Val   Arg   Gln   Ala   Pro   Gly   Gln   Gly   Leu   Glu   Trp   Ile
                                      35                            40                            45

Gly   Tyr   Ile   Asn   Pro   Ser   Gly   Tyr   Thr   Glu   Tyr   Asn   Gln   Lys   Phe
                          50                            55                            60

Lys   Asp   Lys   Ala   Thr   Ile   Thr   Ala   Asp   Glu   Ser   Thr   Asn   Thr   Ala   Tyr
              65                                70                            75                            80

Met   Glu   Leu   Ser   Ser   Leu   Arg   Ser   Glu   Asp   Thr   Ala   Val   Tyr   Tyr   Cys
                                      85                            90                            95

Ala   Arg   Gly   Gly   Gly   Val   Phe   Asp   Tyr   Trp   Gly   Gln   Gly   Thr   Leu   Val
                                      100                           105                           110

Thr   Val   Ser   Ser
                                115
```

( 2 ) INFORMATION FOR SEQ ID NO:87:

( i ) SEQUENCE CHARACTERISTICS:
      ( A ) LENGTH: 107 amino acids
      ( B ) TYPE: amino acid
      ( D ) TOPOLOGY: linear ( i i ) MOLECULE TYPE: protein ( x i ) SEQUENCE DESCRIPTION: SEQ ID NO:87:

```
              Asp   Ile   Gln   Met   Thr   Gln   Ser   Pro   Ser   Ser   Leu   Ser   Ala   Ser   Val   Gly
              1                       5                             10                            15

Asp   Arg   Val   Thr   Ile   Thr   Cys   Arg   Ala   Ser   Gln   Asp   Ile   Asn   Ser   Tyr
                                      20                            25                            30

Leu   Ser   Trp   Phe   Gln   Gln   Lys   Pro   Gly   Lys   Ala   Pro   Lys   Thr   Leu   Ile
                                      35                            40                            45

Tyr   Arg   Ala   Asn   Arg   Leu   Glu   Ser   Gly   Val   Pro   Ser   Arg   Phe   Ser   Gly
                          50                            55                            60

Ser   Gly   Ser   Gly   Thr   Asp   Tyr   Thr   Leu   Thr   Ile   Ser   Ser   Leu   Gln   Tyr
              65                                70                            75                            80

Glu   Asp   Phe   Gly   Ile   Tyr   Tyr   Cys   Gln   Gln   Tyr   Asp   Glu   Ser   Pro   Trp
                                      85                            90                            95

Thr   Phe   Gly   Gly   Gly   Thr   Lys   Leu   Glu   Ile   Lys
                                      100                           105
```

(2) INFORMATION FOR SEQ ID NO:88:

(i) SEQUENCE CHARACTERISTICS:
(A) LENGTH: 118 amino acids
(B) TYPE: amino acid
(D) TOPOLOGY: linear (ii) MOLECULE TYPE: protein (xi) SEQUENCE DESCRIPTION: SEQ ID NO:88:

```
Gln Ile Gly Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
                20                  25                  30
Gly Met Asn Trp Val Lys Gln Ala Pro Gly Lys Gly Leu Arg Trp Met
            35                  40                  45
Gly Trp Ile Asn Thr His Thr Gly Glu Pro Thr Tyr Ala Asp Asp Phe
        50                  55                  60
Lys Gly Arg Phe Ala Phe Ser Leu Glu Thr Ser Ala Ser Thr Ala Tyr
65                  70                  75                  80
Leu Gln Ile Asn Asn Leu Lys Asn Glu Asp Thr Ala Thr Tyr Phe Cys
                85                  90                  95
Thr Arg Arg Gly Tyr Asp Trp Tyr Phe Asp Val Trp Gly Ala Gly Thr
            100                 105                 110
Thr Val Thr Val Ser Ser
            115
```

(2) INFORMATION FOR SEQ ID NO:89:

(i) SEQUENCE CHARACTERISTICS:
(A) LENGTH: 118 amino acids
(B) TYPE: amino acid
(D) TOPOLOGY: linear (ii) MOLECULE TYPE: protein (xi) SEQUENCE DESCRIPTION: SEQ ID NO:89:

```
Glu Ile Gln Leu Val Gln Ser Gly Gly Gly Leu Val Lys Pro Gly Gly
1               5                   10                  15
Ser Val Arg Ile Ser Cys Ala Ala Ser Gly Tyr Thr Phe Thr Asn Tyr
                20                  25                  30
Gly Met Asn Trp Val Arg Gln Ala Pro Gly Lys Gly Leu Glu Trp Met
            35                  40                  45
Gly Trp Ile Asn Thr His Thr Gly Glu Pro Thr Tyr Ala Asp Ser Phe
        50                  55                  60
Lys Gly Thr Arg Thr Phe Ser Leu Asp Asp Ser Lys Asn Thr Ala Tyr
65                  70                  75                  80
Leu Gln Ile Asn Ser Leu Arg Ala Glu Asp Thr Ala Val Tyr Phe Cys
                85                  90                  95
Thr Arg Arg Gly Tyr Asp Trp Tyr Phe Asp Val Trp Gly Gln Gly Thr
            100                 105                 110
Thr Val Thr Val Ser Ser
            115
```